(12) United States Patent
David et al.

(10) Patent No.: US 7,410,506 B2
(45) Date of Patent: Aug. 12, 2008

(54) DICATIONIC BIS-HYDRAZONE COMPOUND, DYE COMPOSITION COMPRISING AT LEAST ONE SUCH COMPOUND, IMPLEMENTATION PROCESS THEREFOR AND USES THEREOF

(75) Inventors: Hervé David, La Varenne Saint Hilaire (FR); Andrew Greaves, Montevrain (FR); Leïla Hercouet, Neuilly-Plaisance (FR); Alain Lagrange, Coupvray (FR)

(73) Assignee: L'Oreal S.A., Paris (FR)

( * ) Notice: Subject to any disclaimer, the term of this patent is extended or adjusted under 35 U.S.C. 154(b) by 298 days.

(21) Appl. No.: 11/249,370

(22) Filed: Oct. 14, 2005

(65) Prior Publication Data
US 2006/0096043 A1    May 11, 2006

Related U.S. Application Data

(60) Provisional application No. 60/627,158, filed on Nov. 15, 2004.

(30) Foreign Application Priority Data
Oct. 14, 2004    (FR)    .................... 04 10870

(51) Int. Cl.
A61Q 5/10 (2006.01)
C07D 211/02 (2006.01)
C07D 233/00 (2006.01)

(52) U.S. Cl. .................. 8/405; 8/406; 8/408; 8/410; 8/435; 8/568; 8/570; 8/574; 546/249; 548/300.1; 548/400

(58) Field of Classification Search ........... 8/405, 8/406, 408, 410, 435, 568, 570, 574; 546/249; 548/300, 400
See application file for complete search history.

(56) References Cited

U.S. PATENT DOCUMENTS

| | | | |
|---|---|---|---|
| 4,003,699 A | 1/1977 | Rose et al. | |
| 5,061,289 A | 10/1991 | Clausen et al. | |
| 5,380,340 A | 1/1995 | Neunhoeffer et al. | |
| 5,534,267 A | 7/1996 | Neunhoeffer et al. | |
| 5,663,366 A | 9/1997 | Neunhoeffer et al. | |
| 5,708,151 A | 1/1998 | Möckli | |
| 5,766,576 A | 6/1998 | Löwe et al. | |
| 6,001,135 A | 12/1999 | Rondeau et al. | |
| 6,284,003 B1 | 9/2001 | Rose et al. | |
| 6,338,741 B1 | 1/2002 | Vidal et al. | |
| 6,730,789 B1 | 5/2004 | Birault et al. | |
| 2004/0143911 A1 | 7/2004 | Vidal | |
| 2004/0244123 A1 | 12/2004 | Vidal et al. | |
| 2004/0244124 A1 | 12/2004 | Pios et al. | |

FOREIGN PATENT DOCUMENTS

| | | |
|---|---|---|
| DE | 2 359 399 | 6/1975 |
| DE | 3 843 892 | 6/1990 |
| DE | 4 133 957 | 4/1993 |
| DE | 195 43 988 | 5/1997 |
| EP | 0 714 954 | 6/1996 |
| EP | 0 770 375 | 5/1997 |
| FR | 2 733 749 | 11/1996 |
| FR | 2 757 388 | 6/1998 |
| FR | 2 801 308 | 5/2001 |
| FR | 2 825 623 | 12/2002 |
| FR | 2 825 702 | 12/2002 |
| FR | 2 825 703 | 12/2002 |
| GB | 1 026 978 | 4/1966 |
| GB | 1 153 196 | 5/1969 |
| JP | 2-19576 | 1/1990 |
| JP | 5-163124 | 6/1993 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |
| WO | WO 01/74950 | 10/2001 |
| WO | WO 03/029359 | 4/2003 |
| WO | WO 2004/083312 | 9/2004 |
| WO | WO 2004/083312 A2 * | 9/2004 |

OTHER PUBLICATIONS

STIC Search Report dated Jun. 14, 2007.*
English language Derwent Abstract of EP 0 770 375, May 2, 1997.
English language Derwent Abstract of JP 20-19576, Jan. 23, 1990.
English language Derwent Abstract of 5-163124, Mar. 12, 1993.
French Search Report for priority application No. FR 0410870, filed Oct. 14, 2004.
Ribes et al., *Bulletin de la Société Chimique de France*, 143-147 (1972).
English Language abstract of Ribes et al., *Bulletin de la Société Chimique de France*, 143-147 (1972).

* cited by examiner

*Primary Examiner*—Eisa B Elhilo
(74) *Attorney, Agent, or Firm*—Finnegan Henderson Farabow Garrett & Dunner LLP

(57) ABSTRACT

The present disclosure relates to a novel family of dicationic bis-hydrazone compounds that may be used as direct dyes, and to a dye composition for dyeing keratin fibers, for example, human keratin fibers such as the hair, comprising, in a suitable dyeing medium, at least one such compound. Also disclosed are dyeing processes implementing this composition and uses thereof.

33 Claims, No Drawings

DICATIONIC BIS-HYDRAZONE COMPOUND, DYE COMPOSITION COMPRISING AT LEAST ONE SUCH COMPOUND, IMPLEMENTATION PROCESS THEREFOR AND USES THEREOF

CROSS-REFERENCE TO RELATED APPLICATION

This application claims benefit of U.S. Provisional Application No. 60/627,158, filed Nov. 15, 2004, the contents of which are incorporated herein by reference. This application also claims benefit of priority under 35 U.S.C. § 119 to French Patent Application No. 04 10870, filed Oct. 14, 2004, the contents of which are also incorporated by reference.

FIELD OF THE INVENTION

The present disclosure relates to a novel family of particular compounds of dicationic bis-hydrazone type, to their use as direct dyes for dyeing keratin fibers and also to dye compositions for dyeing keratin fibers comprising, in a suitable dyeing medium, at least one such dicationic bis-hydrazone compound.

BACKGROUND OF THE INVENTION

It is known practice to dye keratin fibers, such as human hair, with dye compositions containing oxidation dye precursors, which are generally known as oxidation bases, such as ortho- or para-phenylenediamines, ortho- or para-aminophenols and heterocyclic compounds. These oxidation bases are colorless or weakly colored compounds, which, when combined with oxidizing products, may give rise to colored compounds by a process of oxidative condensation.

It is also known that the shades obtained with these oxidation bases may be varied by combining them with couplers or coloration modifiers, the latter being chosen, for instance, from aromatic meta-diamines, meta-aminophenols, meta-diphenols and certain heterocyclic compounds such as indole compounds.

The variety of molecules used as oxidation bases and couplers allows a rich palette of colors to be obtained.

The process of oxidation dyeing comprises applying to the keratin fibers oxidation bases or a mixture of oxidation bases and of couplers with an oxidizing agent, for example aqueous hydrogen peroxide solution, leaving the mixture to act and then rinsing the fibers. The colorations resulting therefrom are typically permanent, strong and resistant to external agents, such as to light, bad weather, washing, perspiration and/or rubbing. The compositions, which are generally applied at basic pH, allow dyeing and simultaneous lightening of the fiber to be obtained, which is reflected in practice by the possibility of obtaining a final coloration that is lighter than the original color. In addition, lightening of the fiber has the advantageous effect of generating a unified color in the case of grey hair, and, in the case of naturally pigmented hair, of bringing out the color, i.e., of making it more visible.

It is also known practice to dye keratin fibers by direct dyeing. The process conventionally used in direct dyeing comprises applying to the keratin fibers direct dyes, which are colored and coloring molecules that have affinity for the fibers, leaving the dyes to act and then rinsing the fibers.

It is known practice, for example, to use direct dyes of the nitrobenzene, anthraquinone or nitropyridine type, dyes of the azo, xanthene, acridine or azine type or triarylmethane dyes, for example.

The colorations resulting therefrom are colorations that are particularly chromatic, but which are, however, temporary or semi-permanent. Specifically, the nature of the interactions that bind the direct dyes to the keratin fiber, and their desorption from the surface and/or from the core of the fiber, are such that the dyeing power and the wash-fastness or perspiration-fastness of the colorations may still be considered insufficient. Certain direct dyes may also be light-sensitive due to the low resistance of the chromophore to photochemical attack, and may lead to fading of the coloration of the hair over time.

It is known practice to use direct dyes in combination with oxidizing agents. However, direct dyes may be sensitive to the action of oxidizing agents such as aqueous hydrogen peroxide solution, and reducing agents such as sodium bisulfite, which makes them generally difficult to use under these conditions.

There is thus a real need to find chromatic direct dyes which can dye keratin fibers just as strongly as oxidation dyes, which are just as stable as oxidation dyes to light, which are also resistant to bad weather, washing and perspiration, and/or which are also sufficiently stable in the presence of oxidizing agents and reducing agents to be able to simultaneously obtain lightening of the fiber either by using lightening direct compositions containing them, or by using oxidation dye compositions containing them. There is also a real need to find direct dyes which can dye keratin fibers to obtain a very wide range of colors, in particular very chromatic colors, without forgetting the "fundamental" shades such as blacks and browns and shades with glints.

DETAILED DESCRIPTION OF THE INVENTION

The present inventors have discovered, surprisingly, a novel family of dicationic bis-hydrazone compounds that may be used as direct dyes for dyeing keratin fibers, e.g., human keratin fibers such as the hair. Dye compositions comprising at least one such dicationic bis-hydrazone compound may solve one or more of the problems listed above.

More specifically, the compositions according to the present disclosure make it possible to obtain dyeing results that are resistant to external agents (light and weather) and/or also to shampoo and perspiration. In addition, these compositions may show improved uptake.

Also disclosed herein is a process for dyeing keratin fibers using the disclosed dicationic bis-hydrazone compounds and also the use of these compounds for obtaining dyeing results that show good resistance to external agents and/or to shampoo.

For the purposes of the present disclosure, and unless otherwise indicated:

an alkyl or alkylene radical is linear or branched;

the alkyl or alkylene radicals or the alkyl part of a radical may be substituted with at least one substituent chosen from the following groups:

hydroxyl, $C_1$-$C_4$ alkoxy or $C_2$-$C_4$ (poly)hydroxyalkoxy, amino, amino substituted with one or more identical or different $C_1$-$C_4$ alkyl groups optionally bearing at least one hydroxyl group, the alkyl radicals possibly forming, with the nitrogen atom to which they are attached, a saturated or unsaturated, optionally substituted 5- or 6-membered heterocycle optionally comprising at least one other nitrogen or non-nitrogen hetero atom;

the aryl or heteroaryl radicals or the aryl or heteroaryl part of a radical may be substituted with at least one substituent borne by a carbon atom, chosen from:
- a $C_1$-$C_{16}$, for example $C_1$-$C_8$, alkyl radical optionally substituted with one or more radicals chosen from hydroxyl, $C_1$-$C_2$ alkoxy, $C_2$-$C_4$ (poly)hydroxyalkoxy, acylamino, amino substituted with two $C_1$-$C_4$ alkyl radicals, which may be identical or different, optionally bearing at least one hydroxyl group, or the two radicals possibly forming, with the nitrogen atom to which they are attached, a saturated or unsaturated, optionally substituted 5- to 7-membered, such as 5- or 6-membered heterocycle optionally comprising another nitrogen or non-nitrogen hetero atom;
- a halogen atom such as chlorine, fluorine or bromine;
- a hydroxyl group;
- a $C_1$-$C_2$ alkoxy radical; a $C_2$-$C_4$ (poly)hydroxyalkoxy radical;
- an amino radical; an amino radical substituted with one or two $C_1$-$C_4$ alkyl radicals, which may be identical or different, optionally bearing at least one hydroxyl or amino group, with two optionally substituted $C_1$-$C_3$ alkyl radicals, the alkyl radicals possibly forming, with the nitrogen atom to which they are attached, a saturated or unsaturated, optionally substituted 5- to 7-membered heterocycle optionally comprising at least one other nitrogen or non-nitrogen hetero atom;
- an acylamino radical (—NR—COR') in which the radical R is chosen from a hydrogen atom and a $C_1$-$C_4$ alkyl radical optionally bearing at least one hydroxyl group and the radical R' is a $C_1$-$C_2$ alkyl radical;
- a carbamoyl radical ((R)$_2$N—CO—) in which the radicals R, which may be identical or different, are chosen from a hydrogen atom and a $C_1$-$C_4$ alkyl radical optionally bearing at least one hydroxyl group;
- an alkylsulfonylamino radical (R'SO$_2$—NR—) in which the radical R is chosen from a hydrogen atom and a $C_1$-$C_4$ alkyl radical optionally bearing at least one hydroxyl group and the radical R' is chosen from a $C_1$-$C_4$ alkyl radical and a phenyl radical;
- an aminosulfonyl radical ((R)$_2$N—SO$_2$—) in which the radicals R, which may be identical or different, are chosen from a hydrogen atom and a $C_1$-$C_4$ alkyl radical optionally bearing at least one hydroxyl group,
- a thiol radical;
- a linear or branched, substituted or unsubstituted $C_1$-$C_8$, such as a $C_1$-$C_4$, alkylthio radical;
- a carboxylic radical in acid form or salified (e.g., with an alkali metal or a substituted or unsubstituted ammonium);
- a nitro radical;
- a nitrile group (CN);
- a trifluoromethyl group (CF$_3$);
- the cyclic or heterocyclic part of a non-aromatic radical may be substituted with at least one substituent borne by a carbon atom chosen from the following groups:
- hydroxyl,
- $C_1$-$C_4$ alkoxy or $C_2$-$C_4$ (poly)hydroxyalkoxy,
- alkylcarbonylamino ((RCO—NR'—) in which the radical R' is chosen from a hydrogen atom and a $C_1$-$C_4$ alkyl radical optionally bearing at least one hydroxyl group, and the radical R is chosen from a $C_1$-$C_2$ alkyl radical and an amino radical substituted with two $C_1$-$C_4$ alkyl groups, which may be identical or different, optionally bearing at least one hydroxyl group, the alkyl radicals possibly forming, with the nitrogen atom to which they are attached a saturated or unsaturated, optionally substituted 5- to 7-membered heterocycle optionally comprising at least one other nitrogen or non-nitrogen hetero atom;
- a hydrocarbon-based chain is unsaturated when it comprises one or more double bonds and/or one or more triple bonds;
- a heteroaromatic or heteroaryl radical corresponds to an aromatic radical in which at least one of the carbon atoms is replaced with a hetero atom chosen from nitrogen, oxygen and sulfur.

In addition, two chromophores DYE are said to be different when the chemical structure of the chromophores is different, or, if the chromophores have the same chemical structure, then the substituents are different from one chromophore to another, or alternatively, if the chromophores have the same chemical structure and identical radicals, the respective positions of the radicals are different from one chromophore to another.

Furthermore, unless otherwise indicated, the limits delimiting the extent of a range of values (i.e., the endpoints) are included in this range of values.

The compounds of the present disclosure are dicationic bis-hydrazone compounds of formula (I):

DYE-L-DYE in which each of the chromophores DYE, which may be identical or different, is chosen from chromophores of formulae (Ia), (Ib), (Ic), (Id), (Ie), (If) and (Ig) below:

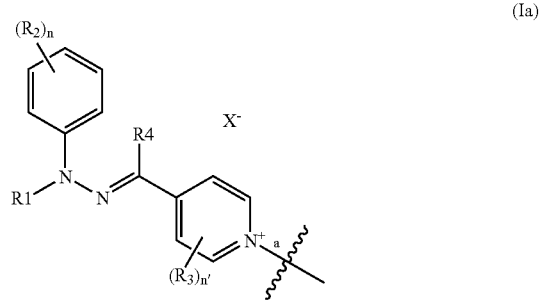
(Ia)

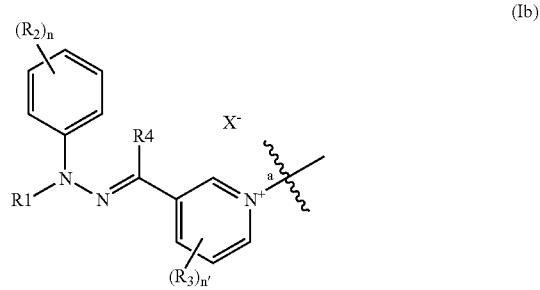
(Ib)

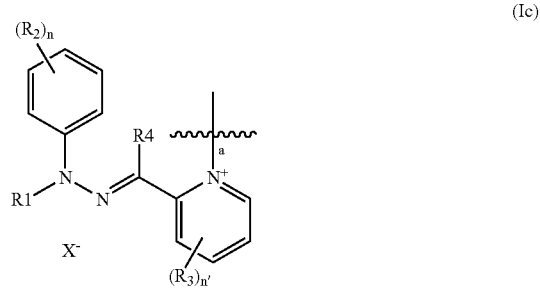
(Ic)

-continued

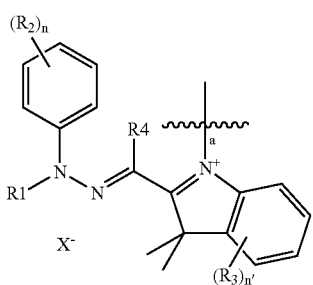
(Id)

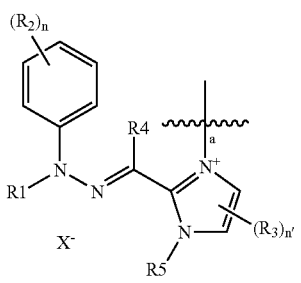
(Ie)

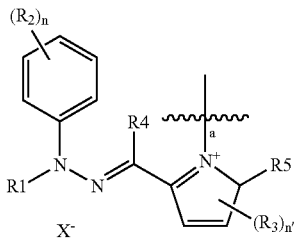
(If)

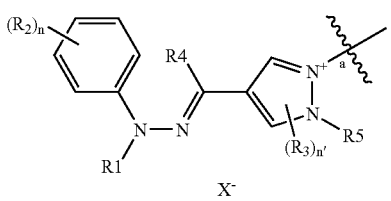
(Ig)

in which:

the groups $R_1$ and $R_5$, independently of each other, are chosen from linear or branched, saturated or unsaturated $C_1$-$C_{20}$, such as $C_1$-$C_{16}$, hydrocarbon-based chains, which can form one or more optionally substituted, optionally aromatic 3- to 7-membered carbon-based rings, this chain being optionally substituted, optionally interrupted with one or more hetero atoms or with one or more groups bearing a hetero atom, these hetero atoms, for example, being chosen from oxygen and nitrogen;

the groups $R_2$ and $R_3$, independently of each other, are chosen from:

a halogen atom chosen from bromine, chlorine and fluorine;

linear or branched, saturated or unsaturated $C_1$-$C_{16}$ hydrocarbon-based chains, which can form one or more optionally aromatic 3- to 6-membered carbon-based rings, this chain being optionally substituted, optionally interrupted with one or more hetero atoms or with one or more groups bearing at least one hetero atom, these hetero atoms, for example, being chosen from oxygen and nitrogen;

a hydroxyl group;

a $C_1$-$C_4$ alkoxy group; a $C_2$-$C_4$ (poly)hydroxyalkoxy group; an alkoxycarbonyl group (RO—CO—) in which R is chosen from a $C_1$-$C_4$ alkyl radical and an alkylcarbonyloxy radical (RCO—O—) in which R is a $C_1$-$C_4$ alkyl radical; an optionally substituted aryloxy group;

an amino group, an amino group substituted with one or more $C_1$-$C_4$ alkyl radicals, which may be identical or different, optionally bearing at least one hydroxyl group, the two alkyl radicals possibly forming, with the nitrogen atom to which they are attached, a saturated or unsaturated, optionally substituted 5- or 6-membered heterocycle, optionally bearing another nitrogen or non-nitrogen hetero atom; an alkylcarbonylamino group (RCO—NR—) in which the radicals R, independently of each other, are a $C_1$-$C_4$ alkyl radical; a carbamoyl group ($(R)_2$N—CO—) in which the radicals R, independently of each other, are chosen from a hydrogen atom and a $C_1$-$C_4$ alkyl radical; a ureido group ($N(R)_2$—CO—NR'—) in which the radicals R and R', independently of each other, are chosen from a hydrogen atom and a $C_1$-$C_4$ alkyl radical; a sulfonamide group ($(R)_2$N—$SO_2$—) in which the radicals R, independently of each other, are chosen from a hydrogen atom and a $C_1$-$C_4$ alkyl radical; an alkylthio group (R—S—) in which the group R is a $C_1$-$C_4$ alkyl radical; an alkylsulfonylamino group ($RSO_2$—NR'—) in which the radicals R and R', independently of each other, are chosen form a hydrogen atom and a $C_1$-$C_4$ alkyl radical;

a nitro group; a cyano group; a halogen atom, such as chlorine or fluorine; a trifluoromethyl group ($CF_3$);

it should be noted that when the main ring does not contain the maximum number of substituents, then the unsubstituted position bears a hydrogen atom;

$R_1$ and $R_2$ may also form, with the nitrogen atom substituted with $R_1$, a saturated or unsaturated, substituted or unsubstituted 5- or 6-membered heterocycle;

two adjacent radicals $R_2$ may form, together with the carbon atoms to which they are attached, a saturated or unsaturated, substituted or unsubstituted 5- or 6-membered aromatic ring or heterocycle;

two adjacent radicals $R_3$ can together form a saturated or unsaturated, substituted or unsubstituted 5- or 6-membered aromatic ring or heterocycle;

the groups $R_4$, independently of each other, are chosen from:

a hydrogen atom;

a linear or branched, saturated or unsaturated $C_1$-$C_{16}$ hydrocarbon-based chain, which can form one or more optionally aromatic 3- to 6-membered carbon-based rings, this chain being optionally substituted, optionally interrupted with one or more hetero atoms or with one or more groups bearing at least one hetero atom chosen, for example, from oxygen and nitrogen;

an amino group, an amino group substituted with one or more $C_1$-$C_4$ alkyl radicals, which may be identical or different, optionally bearing at least one hydroxyl group, the two alkyl radicals possibly forming, with the nitrogen atom to which they are attached, a saturated or unsaturated, optionally substituted 5- or 6-membered heterocycle, optionally bearing another nitrogen or non-nitrogen hetero atom; an alkylcarbonylamino group (RCO—NR—) in which the radicals R, independently of each other, are chosen from $C_1$-$C_4$ alkyl radicals; a ureido group ($N(R)_2$—CO—NR'—)

in which the radicals R and R', independently of each other, are chosen from a hydrogen atom and a $C_1$-$C_4$ alkyl radical; an alkylsulfonylamino group ($RSO_2$—NR'—) in which the radicals R and R', independently of each other, are chosen from a hydrogen atom and a $C_1$-$C_4$ alkyl radical;

n is an integer ranging from 0 to 5, n' is an integer ranging from 0 to 4, the bond a in formulae (Ia), (Ib), (Ic), (Id), (Ie), (If) and (Ig) links each of the chromophores DYE to the linker L of formula (I), X is an organic or mineral anion or mixture of anions for equilibrating the charge(s) of the compounds (Ia), (Ib), (Ic), (Id), (Ie), (If) and (Ig), chosen, for example, from a halide such as chloride, bromide, fluoride or iodide; a hydroxide; a sulfate; a hydrogen sulfate; alkyl sulfates in which the linear or branched alkyl part is of $C_1$-$C_6$, for instance the methyl sulfate or ethyl sulfate ion; carbonates and hydrogen carbonates such as acetate, citrate, tartrate and oxalate; alkylsulfonates in which the linear or branched alkyl part is of $C_1$-$C_6$, for instance the methylsulfonate ion; arylsulfonates in which the aryl, e.g., phenyl, part is optionally substituted with one or more $C_1$-$C_4$ alkyl radicals, for instance 4-tolylsulfonate; alkylsulfonyls such as mesylate.

It is pointed out that when the compounds of formula (I) are such that the two chromophores DYE are identical and correspond to formula (Ia) with n=n'=0, then the group L is not one of the following groups:

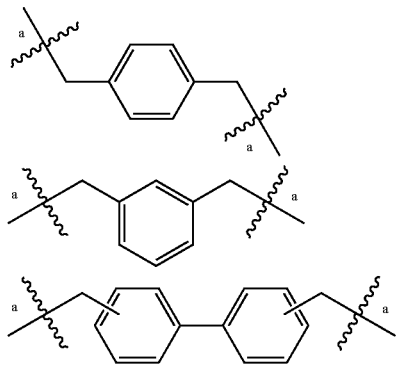

In at least one embodiment, when the two chromophores DYE are identical or different and correspond to formula (Ia) with n=n'=0, then the group L is not one of the three above-mentioned groups.

The group L is a linker linking the two chromophores DYE; L is chosen from a linear or branched $C_1$-$C_{60}$, such as $C_2$-$C_{40}$, hydrocarbon-based chain, which can form one or more optionally aromatic, optionally substituted 3- to 7-membered carbon-based rings, this chain optionally being substituted, optionally interrupted with one or more hetero atoms or with one or more groups bearing a hetero atom, chosen, for example, from oxygen, nitrogen and sulfur, L does not comprise any peroxide, nitro, diazo or nitroso groups, the linker L is linked to the quaternized nitrogen atom of each of the chromophores DYE via a carbon atom and L is not cationic.

According to one embodiment, the linker L is a hydrocarbon-based chain that isolates each of the chromophores so as to stop the electron delocalization of each of the chromophores.

Examples of linkers L that may be mentioned include alkylene radicals ($C_nH_{2n}$) containing from 1 to 60 carbon atoms, e.g., from 2 to 40 carbon atoms or from 2 to 20 carbon atoms, optionally substituted and/or interrupted with one or more hetero atoms chosen from oxygen, nitrogen and sulfur and/or from an $SO_2$ or CO group. These alkylene radicals are, for example, propylene, butylene, pentylene, hexylene, etc.

Examples of linkers L that may also be mentioned include the alkylene radicals as defined above interrupted with a divalent (hetero)aryl radical. According to this embodiment, the linker L may be chosen from:

$C_1$-$C_{20}$ alky-(hetero)aryl-$C_1$-$C_{20}$ alkyl and, for example, by:

$C_1$-$C_{20}$ alky-(hetero)aryl-$C_1$-$C_{20}$ alkyl

The (hetero)arylene radicals are, for example, phenylene or naphthylene, phenanthrylene, triazinyl, pyrimidinyl, pyridyl, pyridazinyl or quinoxalinyl.

Examples of alkylene radicals interrupted with a (hetero)arylene group that may be mentioned include the following radicals linking two chromophores DYE:

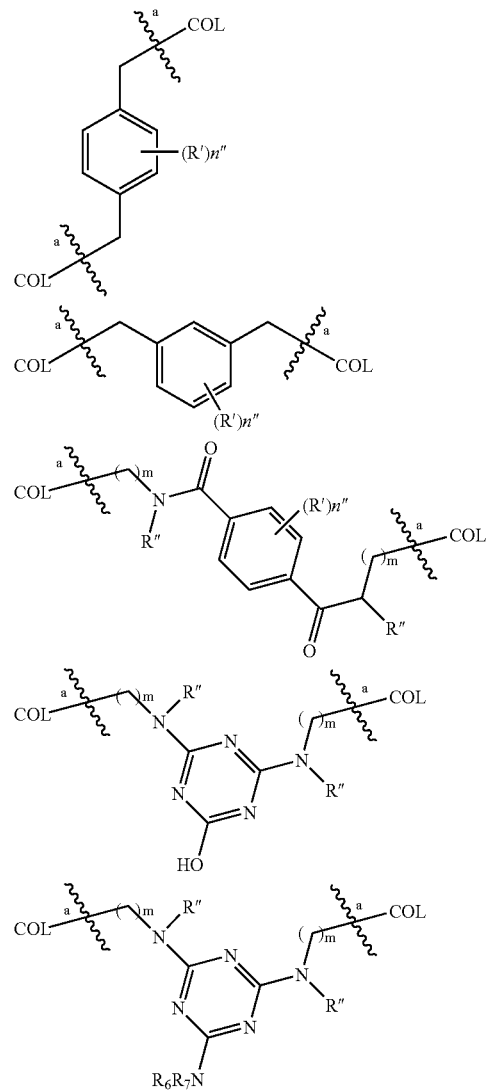

-continued

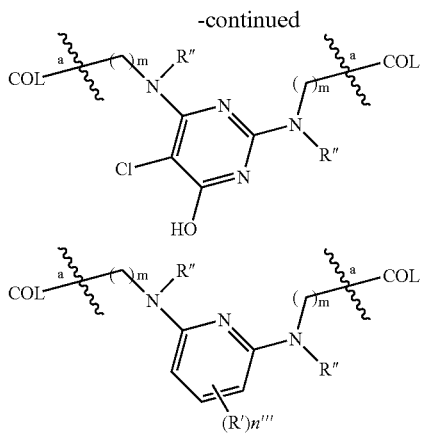

in which:
- R', which may be identical or different, have the same definition as $R_2$ and in one embodiment are a substituent on an aryl or heteroaryl radical as defined above,
- R'', which may be identical or different, are chosen from a hydrogen atom and a $C_1$-$C_4$ alkyl radical;
- $R_6$ and $R_7$ are chosen, independently of each other, from a hydrogen atom and a $C_1$-$C_8$ alkyl radical optionally substituted with one or more hydroxyl, $C_1$-$C_2$ alkoxy, $C_2$-$C_4$ (poly)hydroxyalkoxy, amino, $C_1$-$C_2$ (di)alkylamino or optionally substituted aryl radicals,
- m is an integer from 1 to 6,
- n'' is an integer from 0 to 4,
- n''' is an integer from 0 to 3.

Linkers that may be mentioned include the triazines described in published application WO 03/029359, the alkylenes described in U.S. Pat. No. 5,708,151 and the alkyl-aryl-alkyls described in U.S. Pat. No. 5,708,151.

In at least one embodiment, the compounds of formula (I) according to the present disclosure are such that the linker L is a linear or branched $C_2$-$C_{40}$ and for example, $C_2$-$C_{20}$, hydrocarbon-based chain, optionally substituted and/or interrupted with one or more hetero atoms chosen from oxygen, nitrogen and sulfur.

In another embodiment, the compounds of formula (I) according to the present disclosure are such that the groups $R_1$ are identical and, for example are chosen from a $C_1$-$C_4$ alkyl radical optionally substituted with one or more radicals chosen from hydroxyl, $C_1$-$C_2$ alkoxy, amino and $C_1$-$C_2$ (di)alkylamino radicals; an alkylcarbonyl radical (R—CO—) in which the radical R is a $C_1$-$C_4$ alkyl radical; a carbamoyl group ((R)$_2$N—CO—) in which the radicals R, independently of each other, are chosen from a hydrogen atom and a $C_1$-$C_4$ alkyl radical; an alkylsulfonyl radical (R—SO$_2$—) in which the radical R is a $C_1$-$C_4$ alkyl radical; an optionally substituted phenyl radical.

According to at least one embodiment, the groups $R_1$ are identical and are chosen from methyl, ethyl, 2-hydroxyethyl, 2-methoxyethyl, acetyl (CH$_3$CO—), methylsulfonyl (CH$_3$SO$_2$—) and phenyl radicals.

According to another embodiment, $R_1$ and $R_2$ form, with the nitrogen atom substituted with $R_1$, a saturated or unsaturated 5- or 6-membered heterocycle substituted with one or more alkyl radicals.

$R_2$ and $R_3$, in one embodiment, independently of each other are chosen from:
- a hydrogen atom;
- a halogen atom chosen from bromine, chlorine and fluorine;
- a linear or branched $C_1$-$C_4$ alkyl radical optionally substituted with one or more radicals chosen from hydroxyl, $C_1$-$C_2$ alkoxy, $C_2$-$C_4$ (poly)hydroxyalkoxy, amino, $C_1$-$C_2$ (di)alkylamino, thio (—SH), ($C_1$-$C_4$)alkylsulfinyl, ($C_1$-$C_4$)alkylsulfonyl and ($C_1$-$C_4$)thioalkyl radicals;
- a phenyl radical optionally substituted with one or more radicals chosen from hydroxyl, $C_1$-$C_2$ alkoxy, $C_2$-$C_4$ (poly)hydroxyalkoxy, amino and $C_1$-$C_2$(di)alkylamino radicals, or a halogen atom such as chlorine, fluorine or bromine;
- a $C_1$-$C_4$ alkoxy radical;
- a ($C_1$-$C_4$)alkylsulfonylamino radical;
- a $C_2$-$C_4$ (poly)hydroxyalkoxy radical;
- an amino radical;
- a $C_1$-$C_2$ (di)alkylamino radical;
- a $C_2$-$C_4$ (poly)hydroxyalkylamino radical;
- an alkylcarbonyl radical (R—CO—) in which the radical R is a $C_1$-$C_4$ alkyl radical;
- a carbamoyl radical ((R)$_2$N—CO—) in which the radicals R, independently of each other, are chosen from a hydrogen atom and a $C_1$-$C_4$ alkyl radical;
- an alkylsulfonylamino radical (RSO$_2$N—) in which the radical R is a $C_1$-$C_4$ alkyl radical;
- an aminosulfonyl radical ((R)$_2$NSO$_2$—) in which the radicals R, independently of each other, are chosen from a hydrogen atom and a $C_1$-$C_4$ alkyl radical;
- an alkylthio radical (RS—) in which the radical R is a $C_1$-$C_4$ alkyl radical;
- a thio radical (HS—)
- an alkylsulfinyl radical (RSO—) in which the radical R is a $C_1$-$C_4$ alkyl radical;
- an alkylsulfonyl radical (R—SO$_2$—) in which the radical R is a $C_1$-$C_4$ alkyl radical;
- an alkylcarbonylamino radical (RCONR'—) in which the radical R is chosen from a hydrogen atom and a $C_1$-$C_4$ alkyl radical and the radical R' is also chosen from a hydrogen atom and a $C_1$-$C_4$ alkyl radical.

According to one embodiment, the groups $R_2$ and $R_3$, independently of one another, are chosen from hydrogen and from methyl, ethyl, 2-hydroxyethyl, 2-methoxyethyl, acetyl (CH$_3$CO—), methylsulfonyl (CH$_3$SO$_2$—), amide (CH$_3$CONH—), hydroxyl, amino, methylamino, dimethylamino, 2-hydroxyethylamino, methoxy, ethoxy and phenyl radicals;

the groups $R_4$, independently of each other, are chosen from, for example:
- a hydrogen atom;
- a linear or branched $C_1$-$C_4$ alkyl radical, optionally substituted with one or more radicals chosen from hydroxyl, $C_1$-$C_2$ alkoxy, $C_2$-$C_4$ (poly)hydroxyalkoxy, amino, $C_1$-$C_2$ (di)alkylamino, thio (—SH), ($C_1$-$C_4$) alkylsulfinyl, ($C_1$-$C_4$)alkylsulfonyl and ($C_1$-$C_4$)thioalkyl radicals;
- an amino group, an amino group substituted with one or more $C_1$-$C_4$ alkyl radicals, which may be identical or different, optionally bearing at least one hydroxyl group, an alkylcarbonylamino group (RCO—NR—) in which the radicals R, independently of each other, are chosen from $C_1$-$C_4$ alkyl radicals; a ureido group (N(R)$_2$—CO—NR'—) in which the radicals R and R', independently of each other, are chosen from a hydrogen atom and a $C_1$-$C_4$ alkyl radical; an alkylsulfonylamino group (RSO$_2$—NR'—) in which the radicals R, R', independently of each other, are chosen from a hydrogen atom and a $C_1$-$C_4$ alkyl radical;

a phenyl radical optionally substituted with one or more radicals chosen from hydroxyl, $C_1$-$C_2$ alkoxy, $C_2$-$C_4$ (poly)hydroxyalkoxy, amino, $C_1$-$C_2$ (di)alkylamino, thio (—SH), $(C_1$-$C_4)$alkylsulfinyl, $(C_1$-$C_4)$alkylsulfonyl and $(C_1$-$C_4)$thioalkyl radicals.

In yet another embodiment, $R_4$ is chosen from a hydrogen atom and methyl, ethy and hydroxyethyl radicals; an amino radical or an alkylcarbonylamino group (RCO—NR—); a ureido group $(N(R)_2$—CO—NR'—) in which the radicals R and R', independently of each other, are chosen from a hydrogen atom and a $C_1$-$C_4$ alkyl radical; an alkylsulfonylamino group $(RSO_2$—NR'—) in which the radicals R and R', independently of each other, are chosen from a hydrogen atom and a $C_1$-$C_4$ alkyl radical; a phenyl radical optionally substituted with at least one hydroxyl group.

In one embodiment, the compounds of formula (I) according to the present disclosure are such that the groups $R_5$ are identical and, for example, are chosen from a $C_1$-$C_4$ alkyl radical optionally substituted with one or more radicals chosen from hydroxyl, $C_1$-$C_2$ alkoxy, amino and $C_1$-$C_2$ (di)alkylamino radicals; an optionally substituted phenyl radical.

According to another embodiment, the groups $R_5$ are identical and, for example, are chosen from methyl, ethyl, 2-hydroxyethyl, 2-methoxyethyl and phenyl radicals.

According to one embodiment, in formulae (Ia) and (Ic) n' is equal to 4 and each of the two adjacent radicals $R_3$ forms an aromatic radical, such as a benzene radical.

According to another embodiment, in formulae (Ia), (Ib), (Ic), (Ie) and (If), n' is equal to 2 and the two groups $R_3$ are adjacent and form an aromatic radical, such as a benzene radical.

In at least one embodiment, the linker L is a linear or branched $C_1$-$C_{10}$ alkylene radical optionally interrupted with one or more hetero atoms chosen from oxygen, nitrogen and sulfur, optionally substituted with one or more radicals chosen from hydroxyl, $C_1$-$C_2$ alkoxy, $C_1$-$C_2$ dialkylamino and alkylcarbonyl (R—CO—) radicals, in which the radical R is a $C_1$-$C_4$ alkyl radical, a carbamoyl group $((R)_2N$—CO—) in which the radicals R, independently of each other, are chosen from a hydrogen atom and an alkylsulfonyl radical $(R$—$SO_2$—) in which the radical R is a $C_1$-$C_4$ alkyl radical.

In yet another embodiment, the linker L is a linear $C_1$-$C_{10}$ alkylene radical optionally interrupted with one or more hetero atoms chosen from oxygen and sulfur, optionally substituted with one or more radicals chosen from hydroxyl and $C_1$-$C_2$ alkoxy radicals, and an alkylsulfonyl radical $(R$—$SO_2$—) in which the radical R is a $C_1$-$C_4$ alkyl radical.

According to another embodiment, the linker L is an alkylene radical interrupted with a (hetero)aryl group optionally substituted and/or interrupted with one or more hetero atoms chosen from oxygen and nitrogen, and/or from an $SO_2$ or CO group.

In one embodiment, the cationic bis-hydrazone compound (I) is chosen from the compounds of formulae:

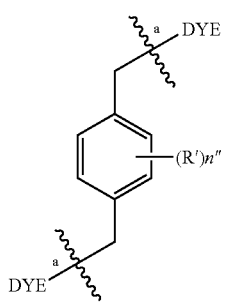

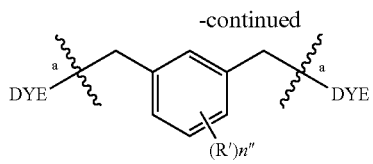

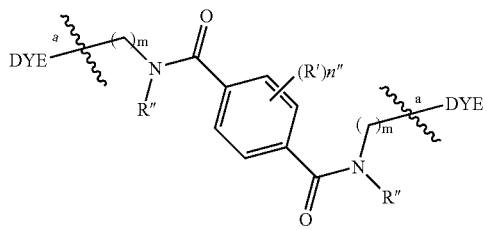

in which:
R' has the same definition as $R_2$,
R" is chosen from a hydrogen atom and a $C_1$-$C_4$ alkyl radical,
m is an integer from 2 to 6,
n" is an integer from 0 to 4.
In one embodiment, $X^-$ is $Br^-$, $Cl^-$, acetate or mesylate.
According to one embodiment, the compounds of formula (I) are chosen from those of the following formulae:

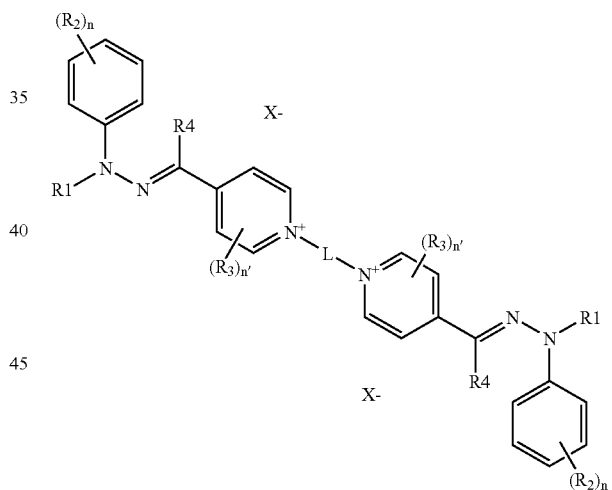

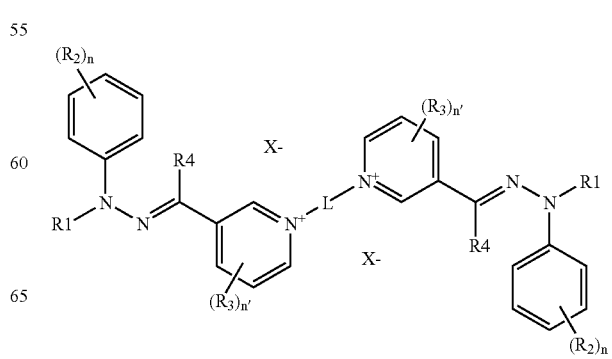

-continued
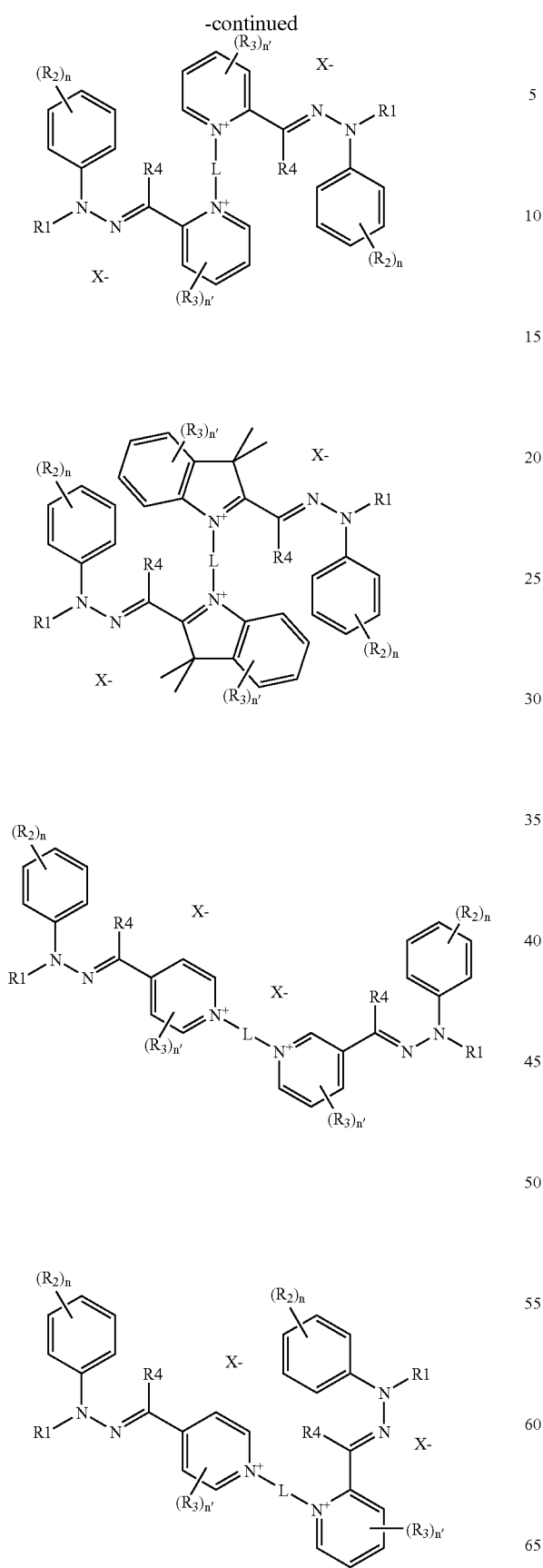
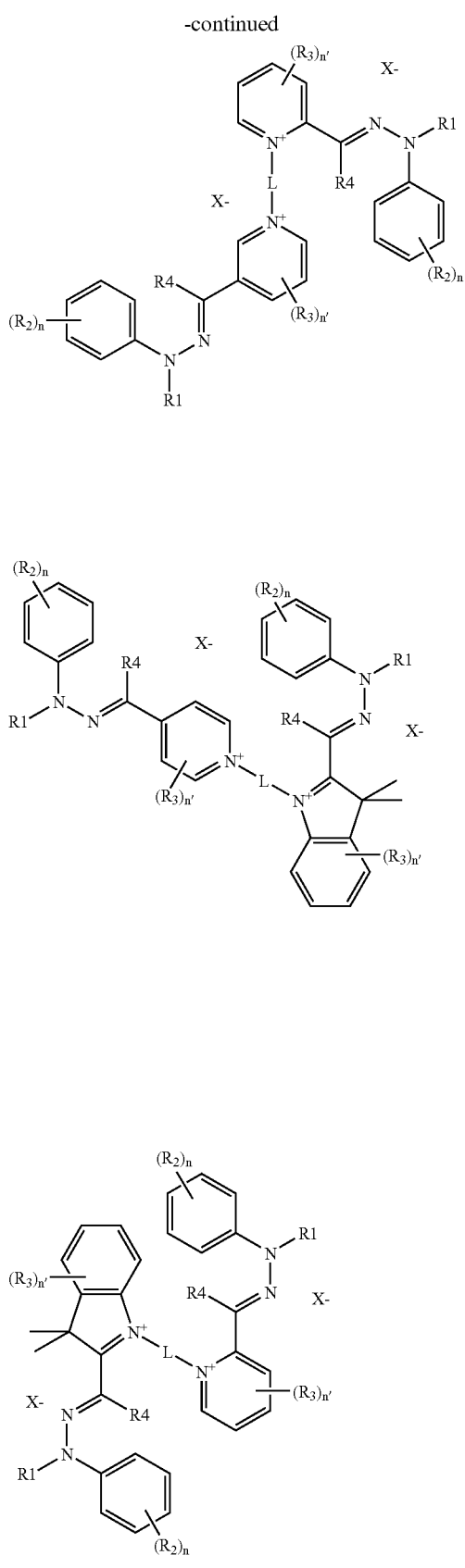

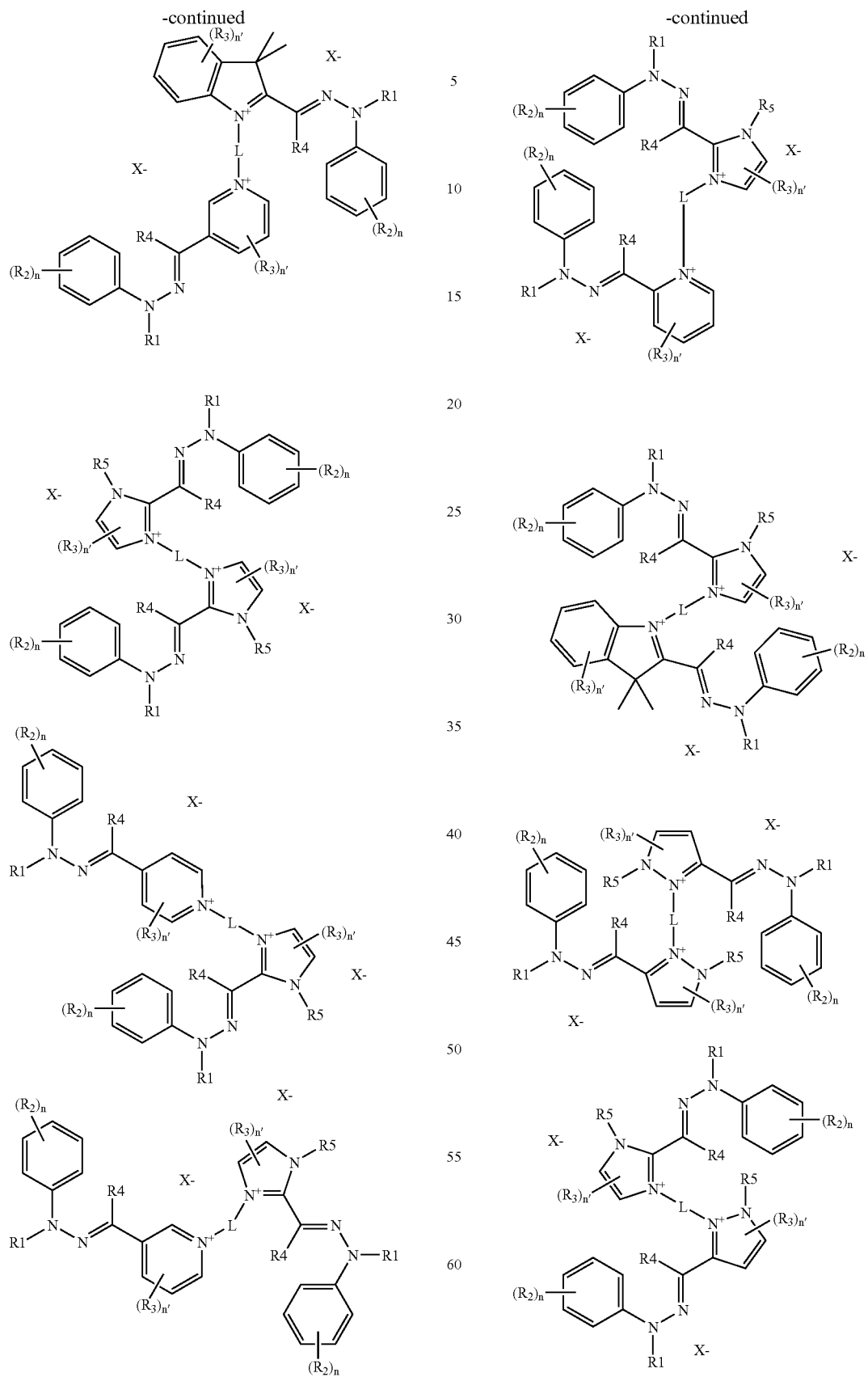

-continued
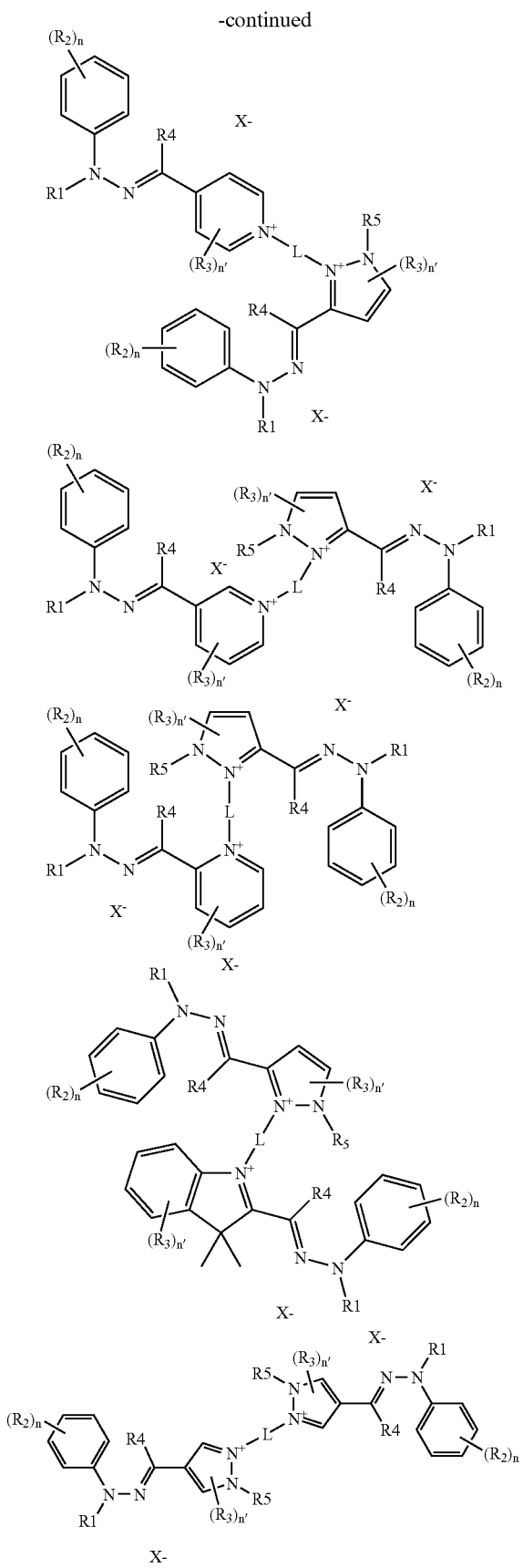
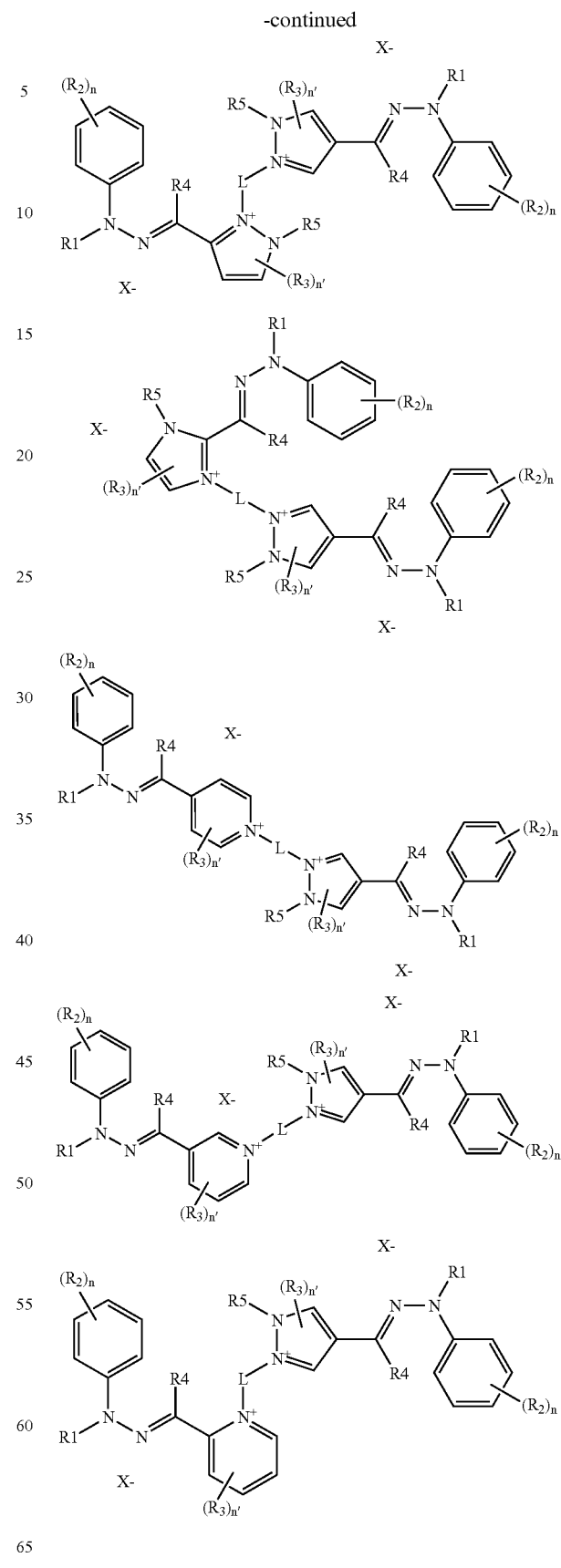

-continued
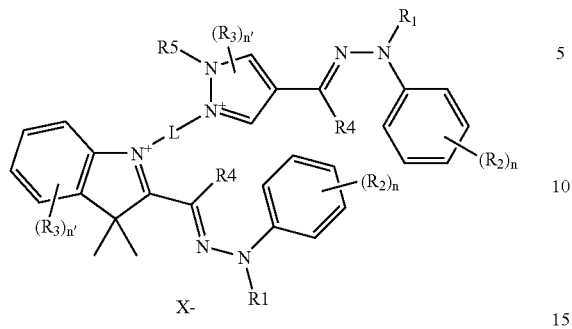
in which the radicals $R_1$, $R_2$, $R_3$, $R_4$, $R_5$, X, n, n' and L are as defined above.
For example, the compounds of dicationic bis-hydrazone type of formula (I) according to the present disclosure may be chosen from the following compounds:
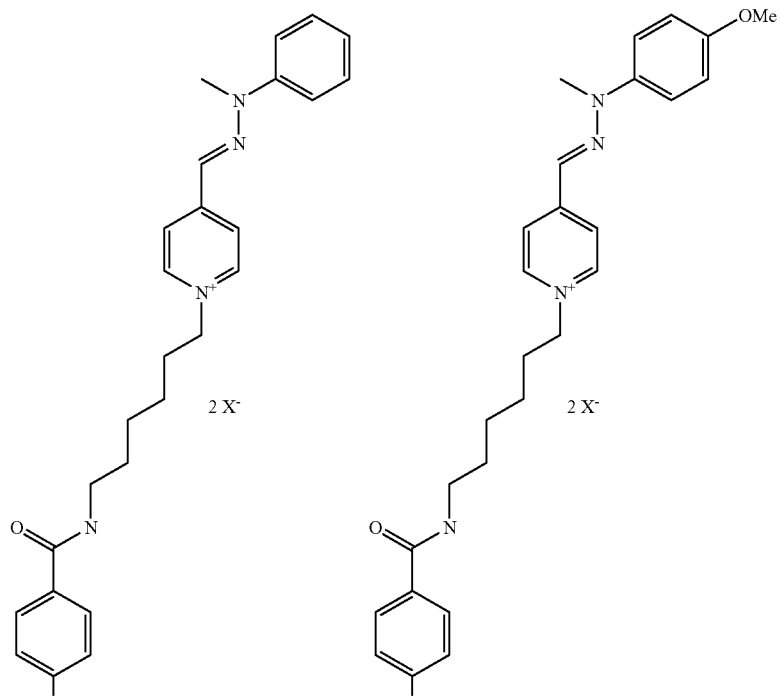

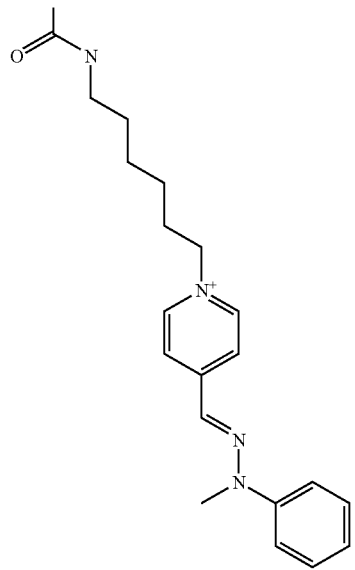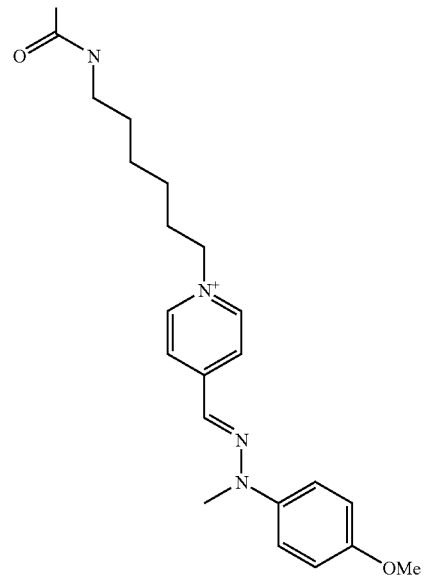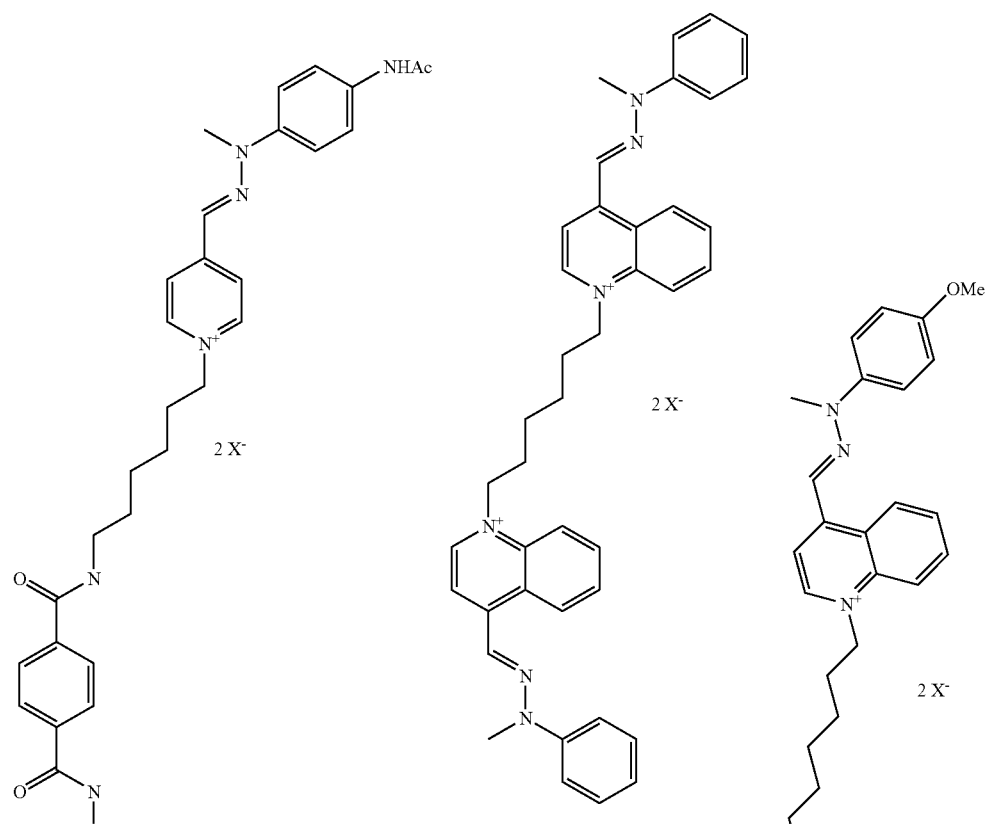

23
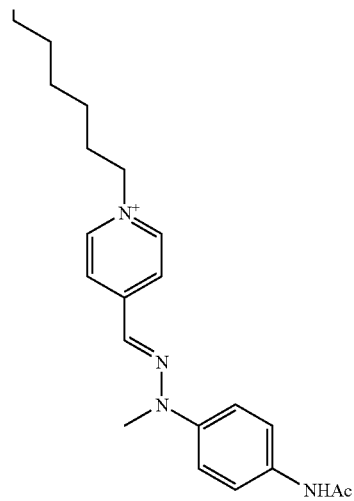
24
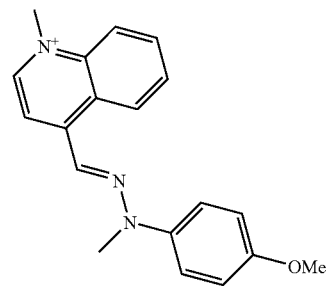
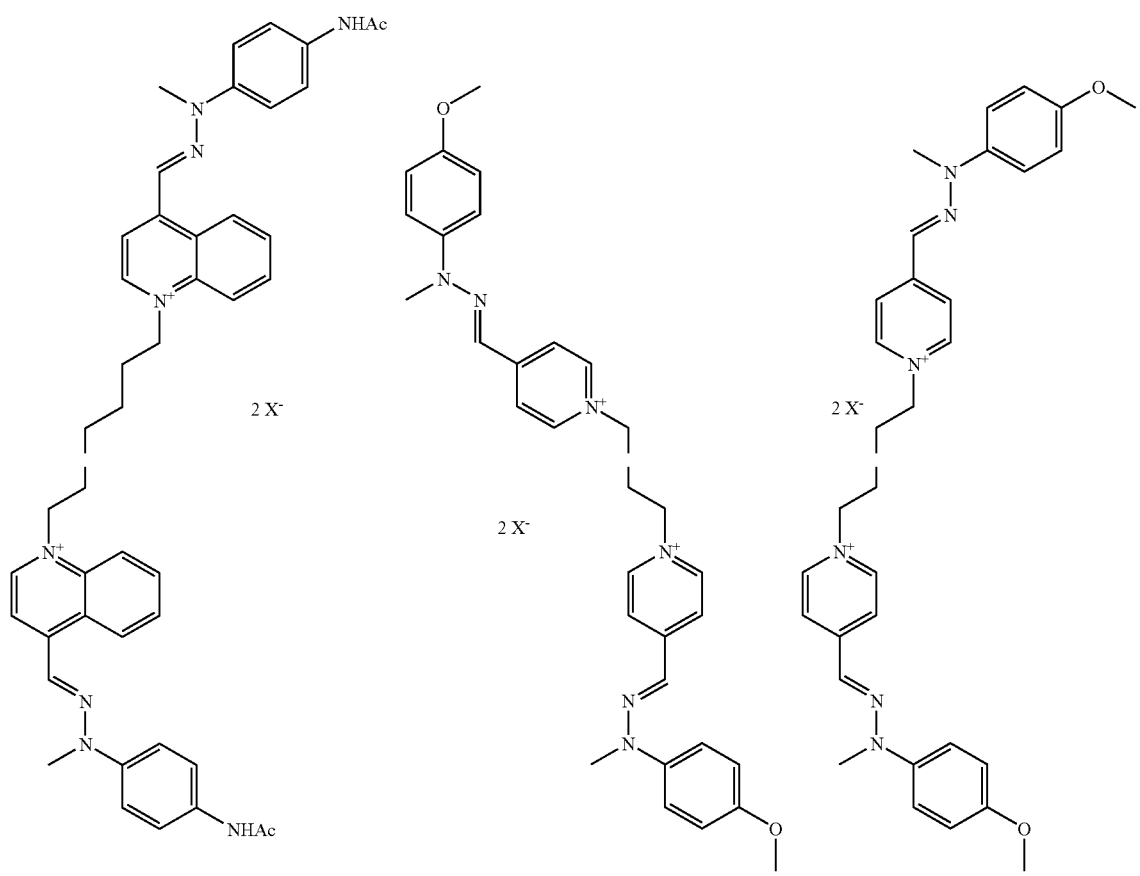

25 26
-continued
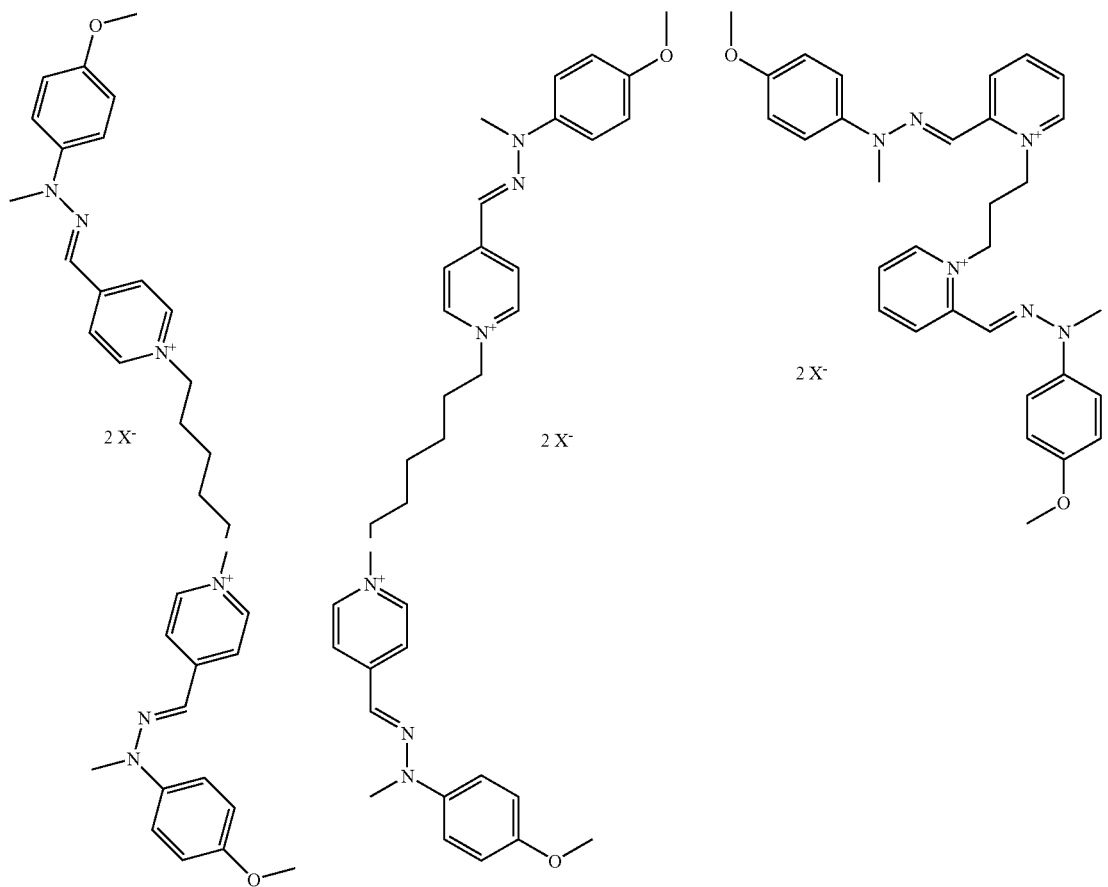
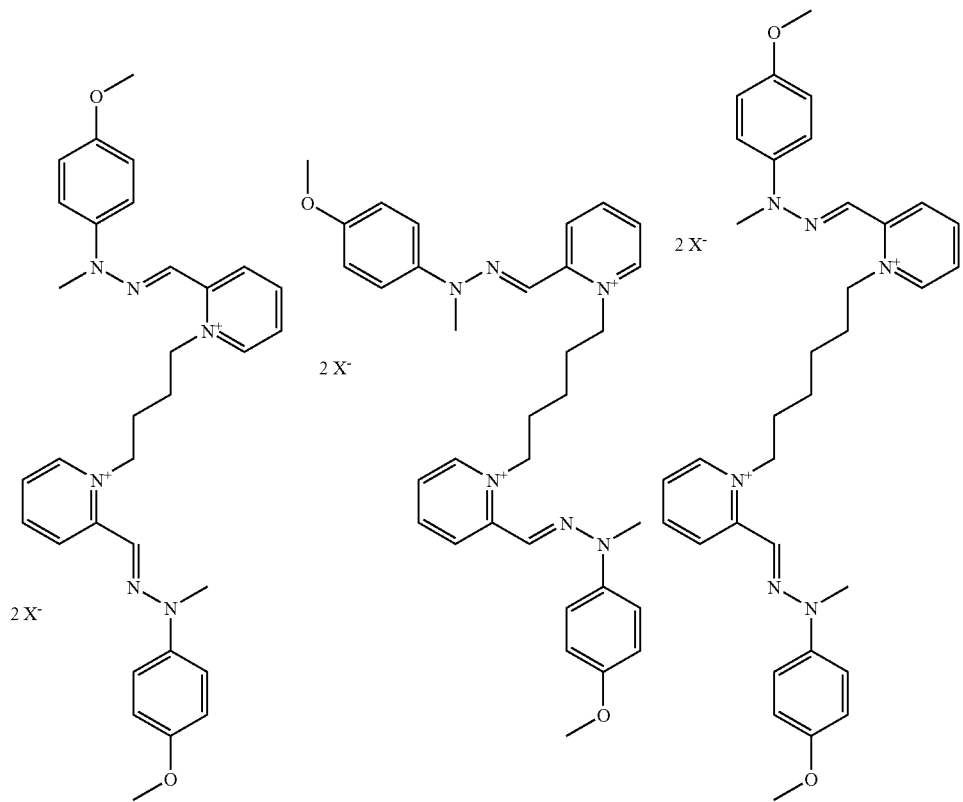

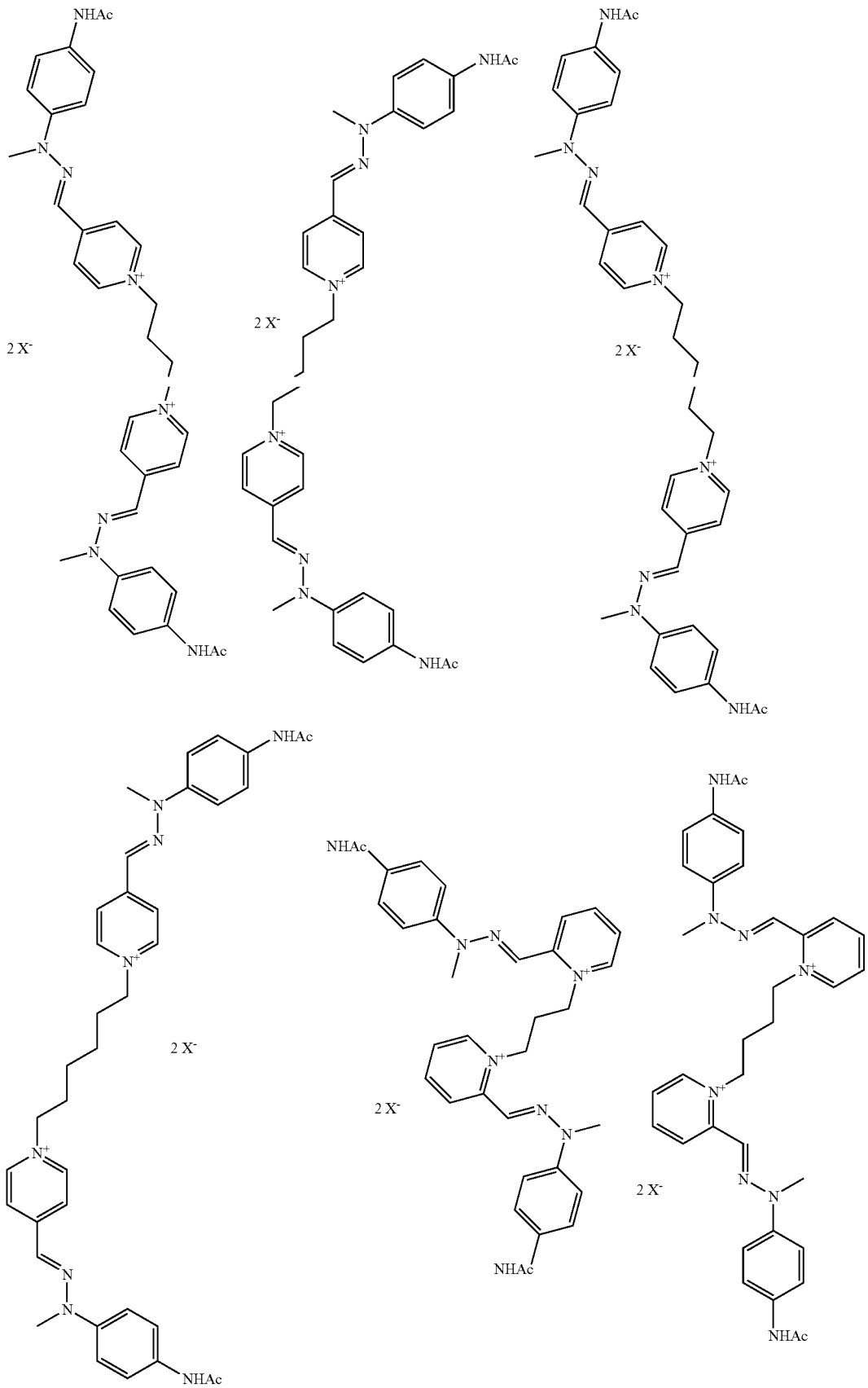

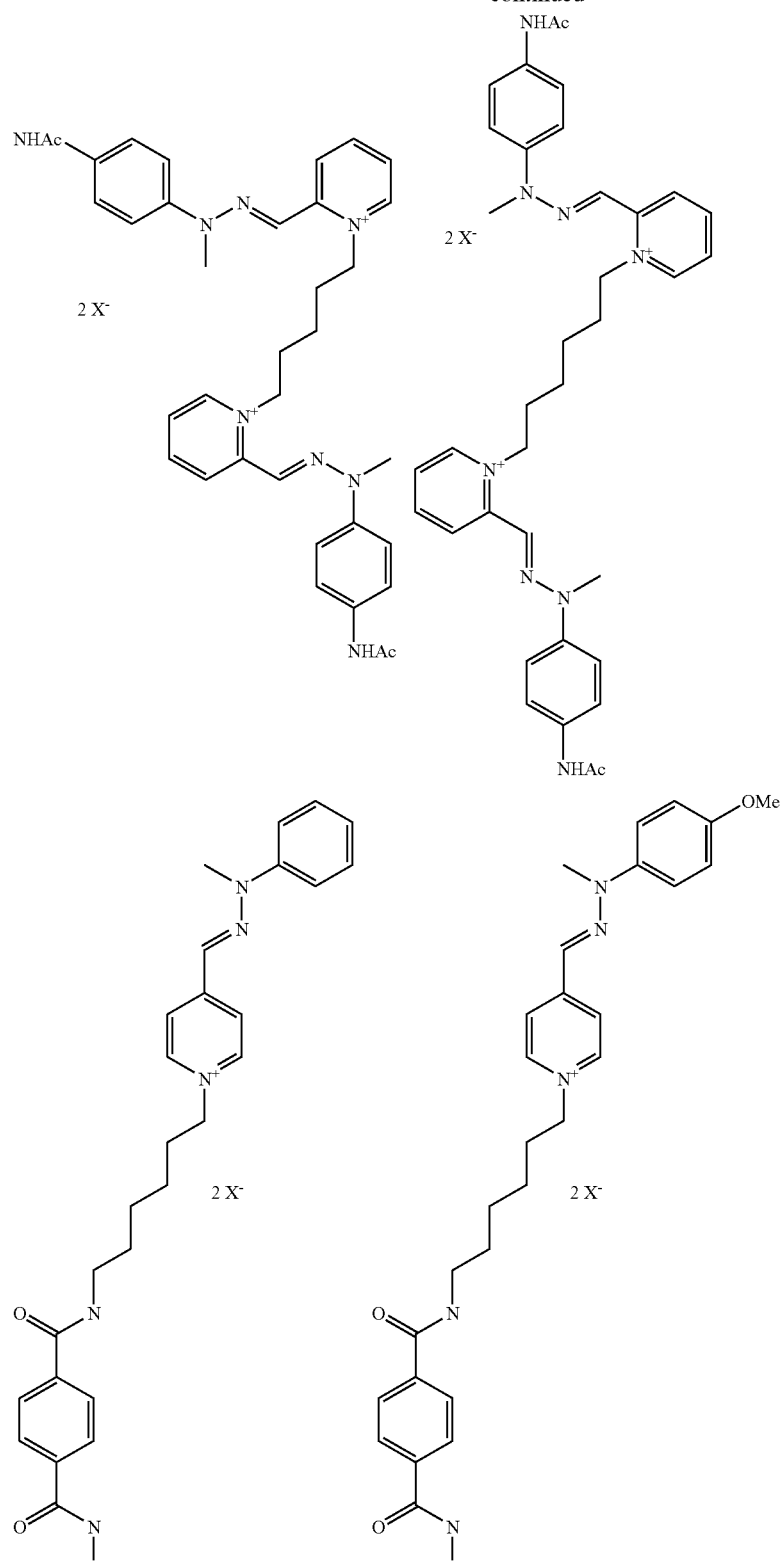

-continued
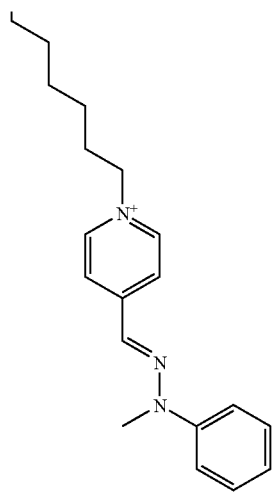
31
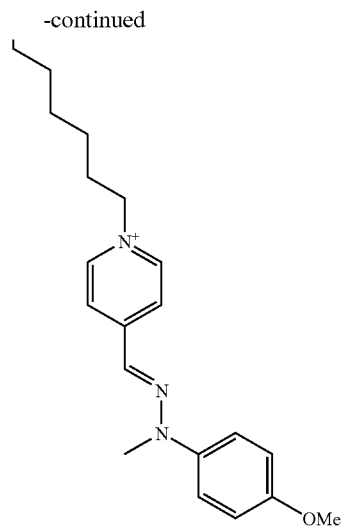
32
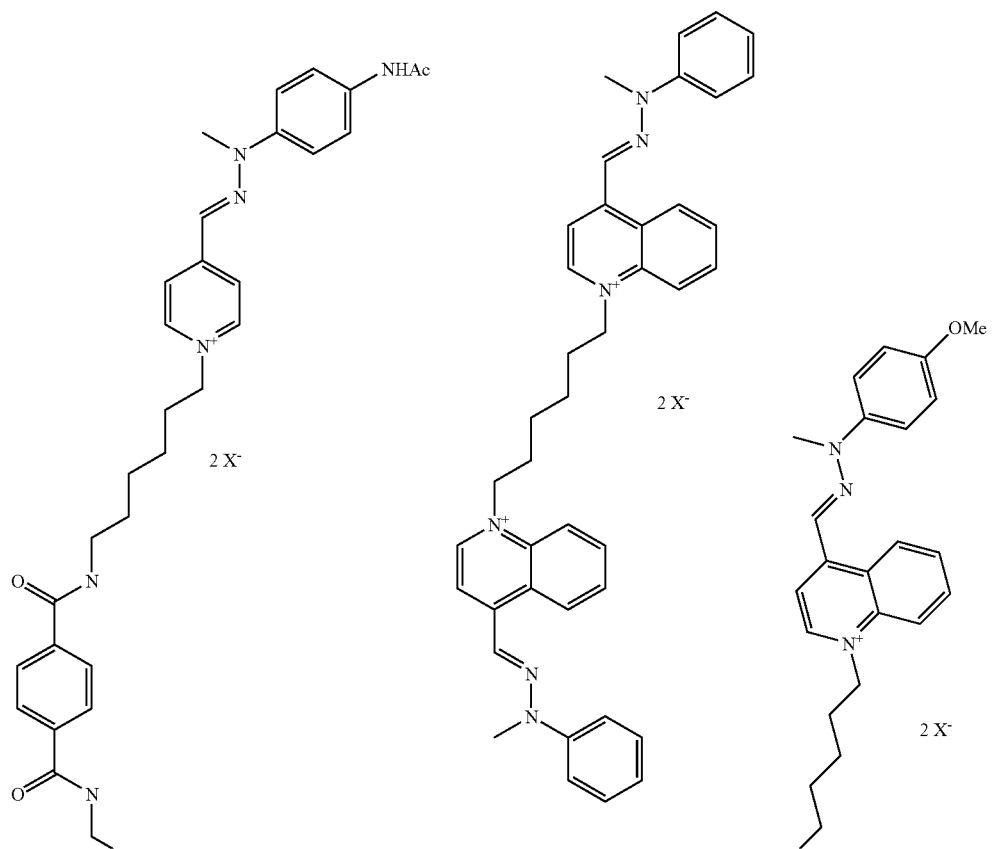

33 34
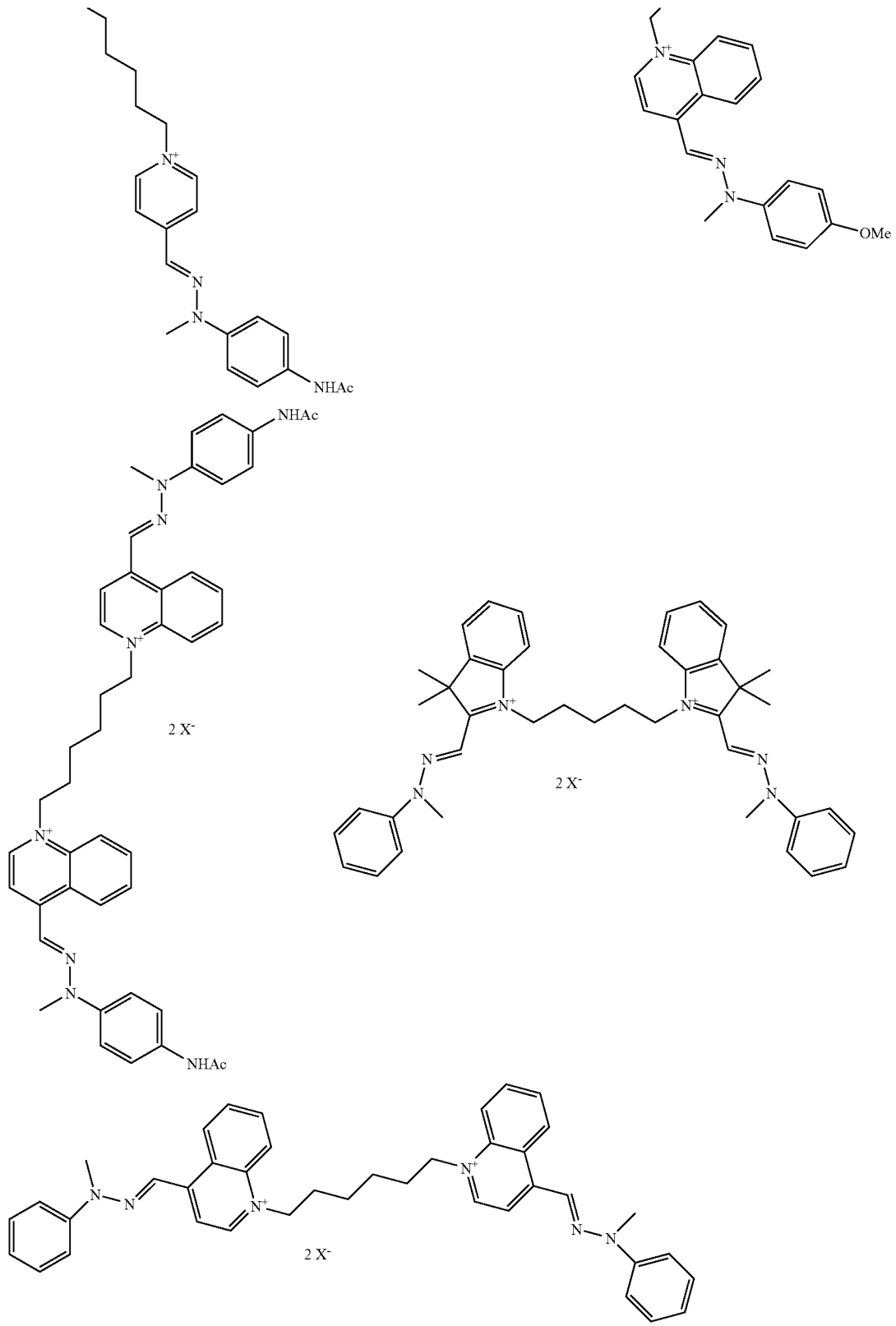
-continued

-continued
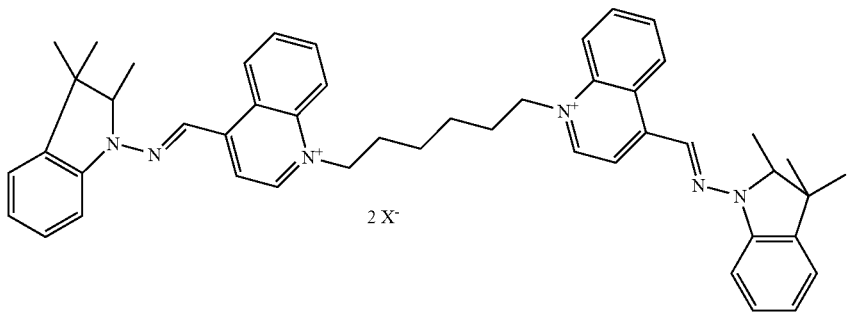
2 X⁻
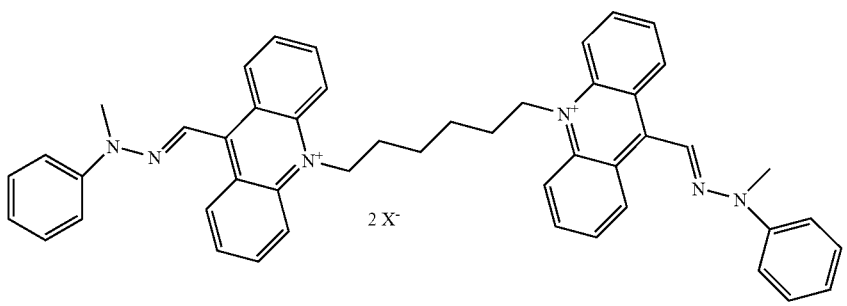
2 X⁻
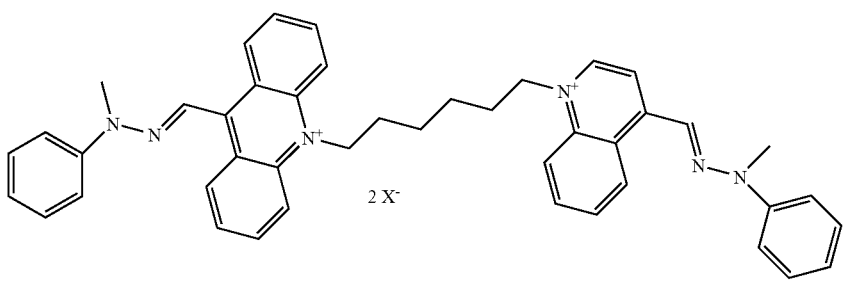
2 X⁻
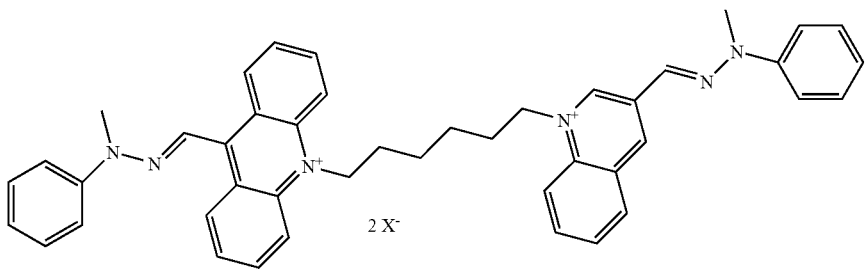
2 X⁻
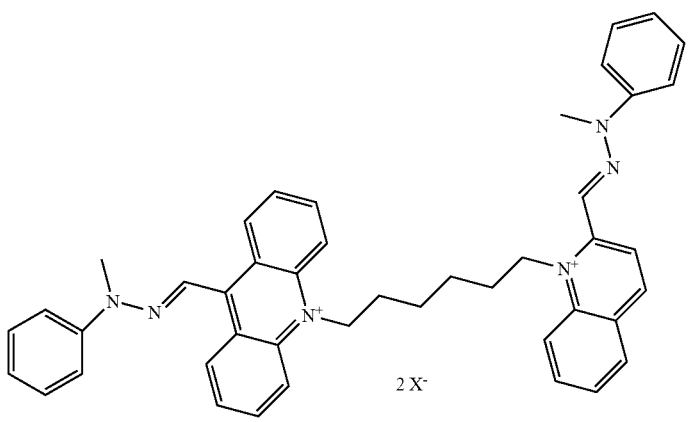
2 X⁻

-continued
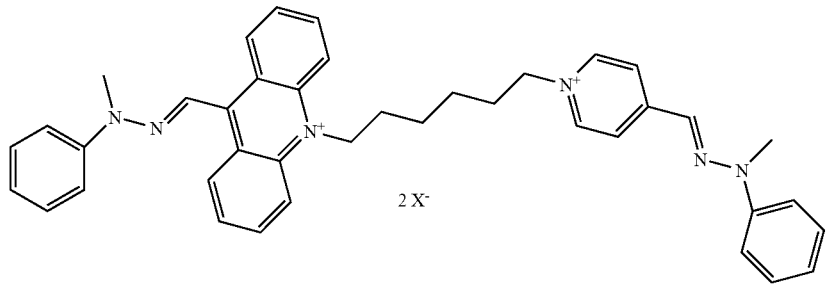
2 X⁻
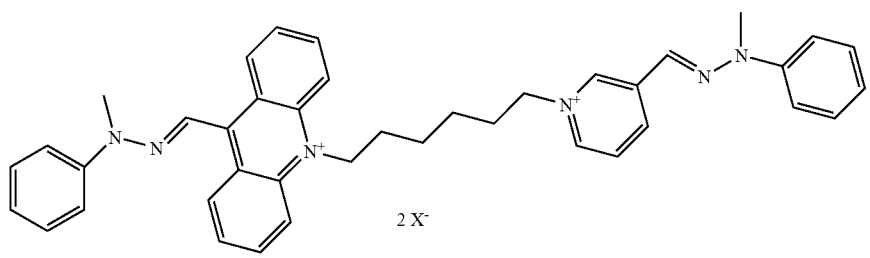
2 X⁻
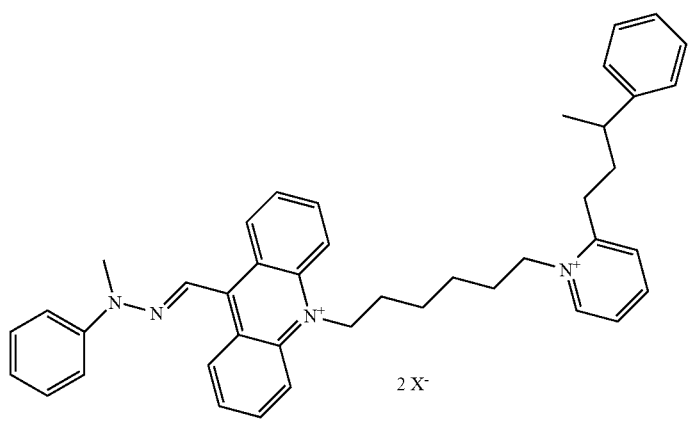
2 X⁻
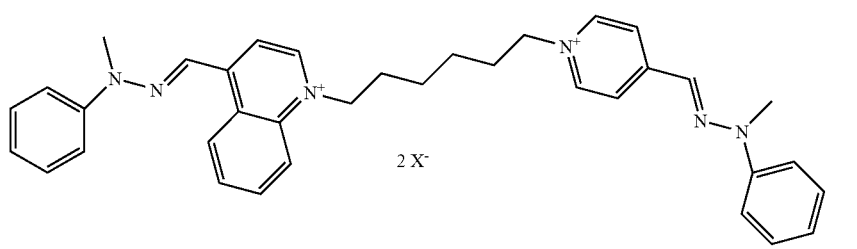
2 X⁻
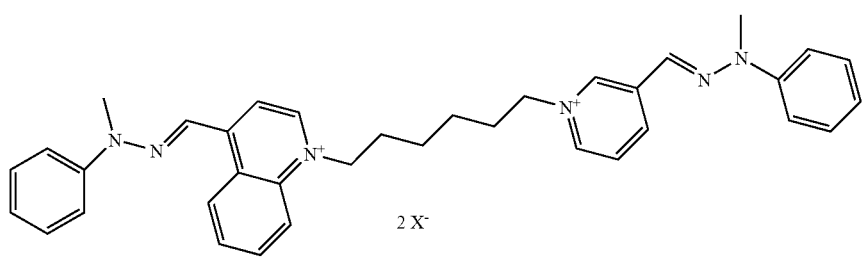
2 X⁻

-continued
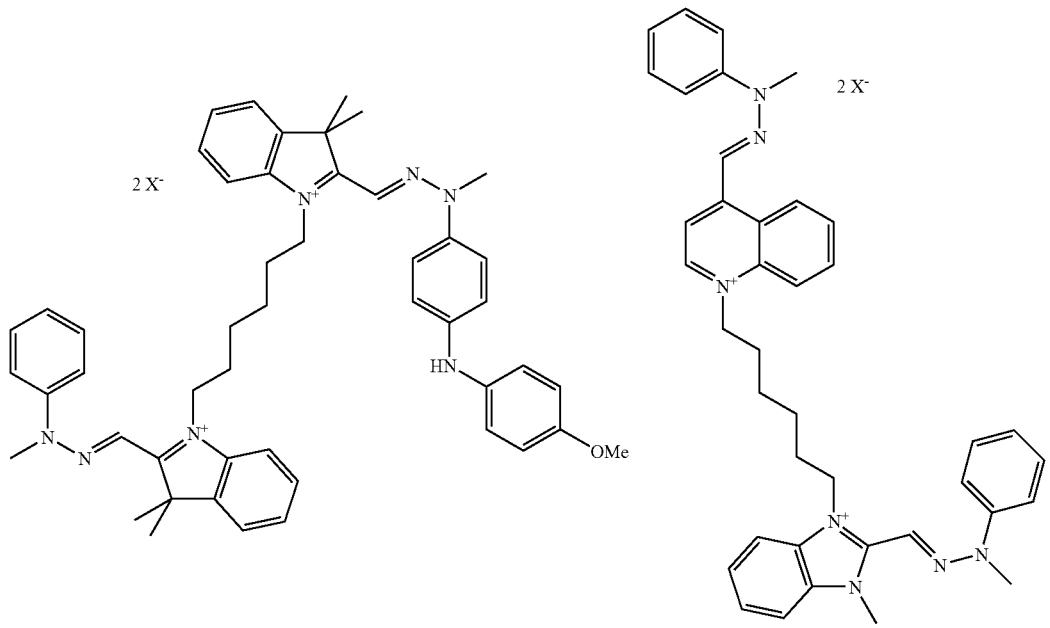
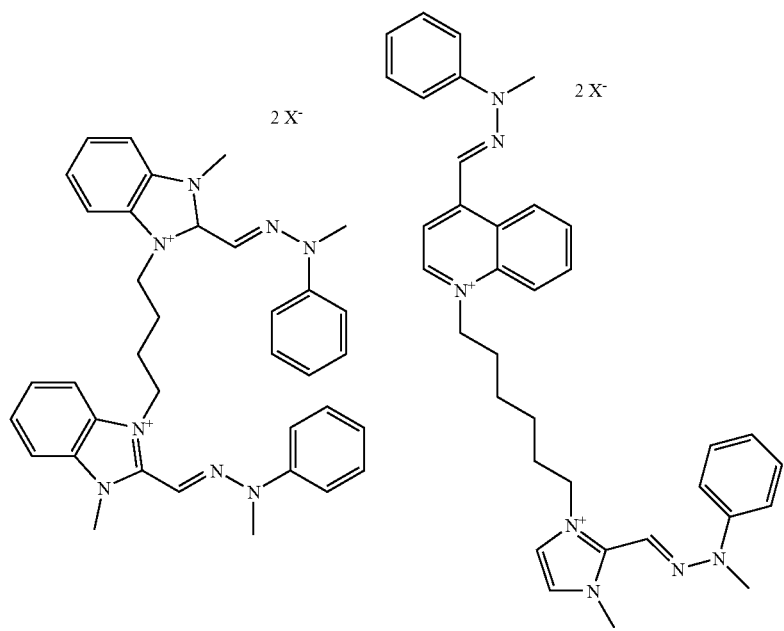

-continued

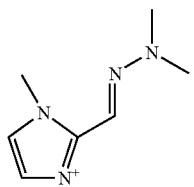

2 X⁻

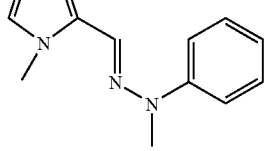

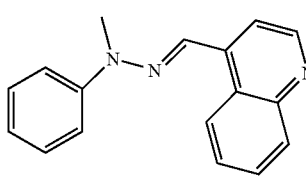

2X⁻

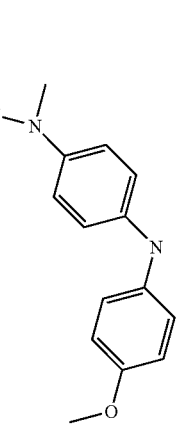

wherein in at least one embodiment, X⁻ is Cl⁻ or Br⁻.

The composition according to the present disclosure comprises from 0.001 to 10%, such as from 0.01 to 10%, by weight of compounds of dicationic bis-hydrazone type of formula (I) relative to the total weight of the composition.

The composition according to the present disclosure may comprise one or more compounds of dicationic bis-hydrazone type of formula (I), mixtures of these compounds then being possible in all relative proportions.

The dye composition in accordance with the present disclosure may also comprise at least one additional direct dye other than the direct dyes of dicationic bis-hydrazone type of formula (Ia) and/or (Ib), and/or (Ic), and/or (Id) and/or (Ie) and/or (If) and/or (Ig), which may be chosen, for instance, from neutral, acidic or cationic nitrobenzene dyes, neutral, acidic or cationic azo direct dyes, neutral, acidic or cationic quinone and in particular anthraquinone direct dyes, azine direct dyes, triarylmethane direct dyes, indoamine direct dyes, tetraazapentamethine-type dyes and natural direct dyes.

Among the benzene-based direct dyes that may be used according to the present disclosure, mention may be made, in a non-limiting manner, of the following compounds:
1,4-diamino-2-nitrobenzene
1-amino-2-nitro-4-β-hydroxyethylaminobenzene
1-amino-2-nitro-4-bis(β-hydroxyethyl)aminobenzene
1,4-bis(β-hydroxyethylamino)-2-nitrobenzene
1-β-hydroxyethylamino-2-nitro-4-bis(β-hydroxyethylamino)benzene
1-β-hydroxyethylamino-2-nitro-4-aminobenzene
1-β-hydroxyethylamino-2-nitro-4-(ethyl)(β-hydroxyethyl)aminobenzene
1-amino-3-methyl-4-β-hydroxyethylamino-6-nitrobenzene
1-amino-2-nitro-4-β-hydroxyethylamino-5-chlorobenzene
1,2-diamino-4-nitrobenzene
1-amino-2-β-hydroxyethylamino-5-nitrobenzene
1,2-bis(β-hydroxyethylamino)-4-nitrobenzene
1-amino-2-tris(hydroxymethyl)methylamino-5-nitrobenzene
1-hydroxy-2-amino-5-nitrobenzene
1-hydroxy-2-amino-4-nitrobenzene
1-hydroxy-3-nitro-4-aminobenzene
1-hydroxy-2-amino-4,6-dinitrobenzene
1-β-hydroxyethyloxy-2-β-hydroxyethylamino-5-nitrobenzene
1-methoxy-2-β-hydroxyethylamino-5-nitrobenzene
1-β-hydroxyethyloxy-3-methylamino-4-nitrobenzene
1-β,γ-dihydroxypropyloxy-3-methylamino-4-nitrobenzene
1-β-hydroxyethylamino-4-β,γ-dihydroxypropyloxy-2-nitrobenzene 1-β,γ-dihydroxypropylamino-4-trifluoromethyl-2-nitrobenzene
1-β-hydroxyethylamino-4-trifluoromethyl-2-nitrobenzene
1-β-hydroxyethylamino-3-methyl-2-nitrobenzene
1-β-aminoethylamino-5-methoxy-2-nitrobenzene
1-hydroxy-2-chloro-6-ethylamino-4-nitrobenzene
1-hydroxy-2-chloro-6-amino-4-nitrobenzene
1-hydroxy-6-bis(β-hydroxyethyl)amino-3-nitrobenzene
1-β-hydroxyethylamino-2-nitrobenzene and
1-hydroxy-4-β-hydroxyethylamino-3-nitrobenzene.

Among the azo direct dyes that may be used according to the present disclosure, mention may be made of the cationic azo dyes described in patent applications WO 95/15144, WO-95/01772 and EP-714954, the contents of which are herein incorporated by reference.

Among these compounds, mention may be made of the following dyes:
1,3-dimethyl-2-[[4-(dimethylamino)phenyl]azo]-1H-imidazolium chloride,
1,3-dimethyl-2-[(4-aminophenyl)azo]-1H-imidazolium chloride,
1-methyl-4-[(methylphenylhydrazono)methyl]pyridinium methyl sulfate.

Among the azo direct dyes that may also be mentioned are the following dyes, described in the Color Index International, 3rd edition:
Disperse Red 17
Acid Yellow 9
Acid Black 1
Basic Red 22
Basic Red 76
Basic Yellow 57
Basic Brown 16
Acid Yellow 36
Acid Orange 7
Acid Red 33
Acid Red 35
Basic Brown 17
Acid Yellow 23
Acid Orange 24
Disperse Black 9.

Mention may also be made of 1-(4'-aminodiphenylazo)-2-methyl-4-bis(β-hydroxyethyl)aminobenzene and 4-hydroxy-3-(2-methoxyphenylazo)-1-naphthalenesulfonic acid.

Among the quinone direct dyes that may be mentioned are the following dyes:
Disperse Red 15
Solvent Violet 13
Acid Violet 43
Disperse Violet 1
Disperse Violet 4
Disperse Blue 1
Disperse Violet 8
Disperse Blue 3
Disperse Red 11
Acid Blue 62
Disperse Blue 7
Basic Blue 22
Disperse Violet 15
Basic Blue 99
and also the following compounds:
1-N-methylmorpholiniumpropylamino-4-hydroxyanthraquinone
1-aminopropylamino-4-methylaminoanthraquinone
1-aminopropylaminoanthraquinone
5-β-hydroxyethyl-1,4-diaminoanthraquinone
-2-aminoethylaminoanthraquinone
1,4-bis(β,γ-dihydroxypropylamino)anthraquinone.

Among the azine dyes that may be mentioned are the following compounds:
Basic Blue 17
Basic Red 2.

Among the triarylmethane dyes that may be used herein, mention may be made of the following compounds:
Basic Green 1
Acid blue 9
Basic Violet 3
Basic Violet 14
Basic Blue 7
Acid Violet 49
Basic Blue 26
Acid Blue 7

Among the indoamine dyes that may be used according to the present disclosure, mention may be made of the following compounds:
2-β-hydroxyethylamino-5-[bis(β-4'-hydroxyethyl)amino]anilino-1,4-benzoquinone
2-β-hydroxyethylamino-5-(2'-methoxy-4'-amino)anilino-1,4-benzoquinone
3-N-(2'-chloro-4'-hydroxy)phenylacetylamino-6-methoxy-1,4-benzoquinone imine
3-N-(3'-chloro-4'-methylamino)phenylureido-6-methyl-1,4-benzoquinone imine
3-[4'-N-(ethyl,carbamylmethyl)amino]phenylureido-6-methyl-1,4-benzoquinone imine.

Among the dyes of the tetraazapentamethine type that may be used according to the present disclosure, mention may be made of the compounds given in the table below, wherein An is an organic or mineral anion chosen, for example, from a halide such as chloride, bromide, fluoride or iodide; a hydroxide; a sulfate; a hydrogen sulfate; a $(C_1-C_6)$alkyl sulfate, for instance a methyl sulfate or an ethyl sulfate; an acetate; a tartrate; an oxalate; a $(C_1-C_6)$alkylsulfonate such as methylsulfonate; an arylsulfonate that is unsubstituted or substituted with a $C_1-C_4$ alkyl radical, for instance a 4-tolylsulfonate. In at least one embodiment, An is a chloride or a methyl sulfate:

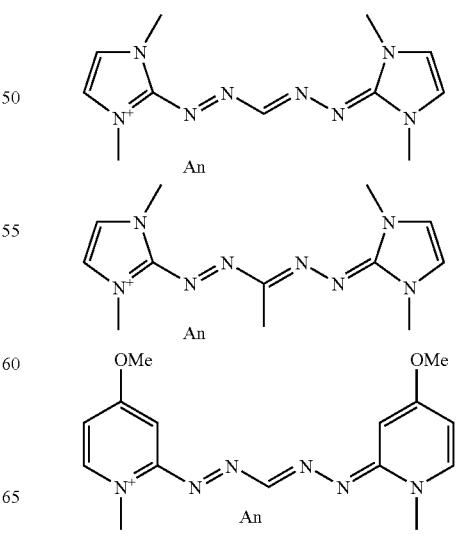

-continued

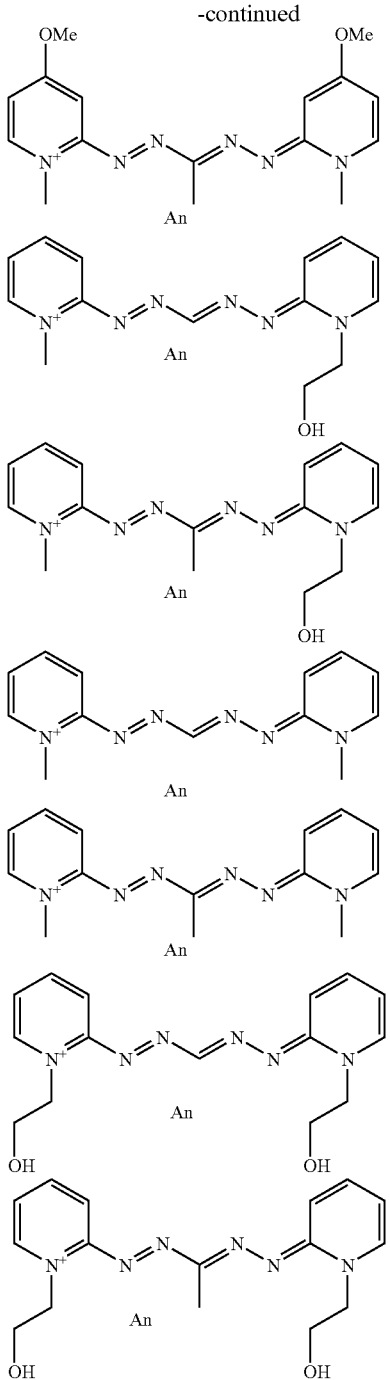

Among the natural direct dyes that may be used according to the present disclosure, mention may be made of lawsone, juglone, alizarin, purpurin, carminic acid, kermesic acid, purpurogallin, protocatechaldehyde, indigo, isatin, curcumin, spinulosin and apigenidin. It is also possible to use extracts or decoctions containing these natural dyes, and also henna-based poultices or extracts.

The at least one additional direct dye is present, in at least one embodiment herein, in an amount ranging from 0.001% to 20% by weight relative to the total weight of the ready-to-use composition, such as from 0.005% to 10% by weight.

The composition of the present disclosure may also comprise at least one oxidation dye precursor: at least one oxidation base and/or at least one coupler.

By way of example, the oxidation bases are chosen from phenylenediamines, bis(phenyl)alkylenediamines, para-aminophenols, ortho-aminophenols, heterocyclic bases other than the heterocyclic para-phenylenediamines of formula (I), and the addition salts thereof.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

For example, among the para-phenylenediamines listed above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, may be mentioned.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, and 2,5-diaminopyridine, 2-(4-methoxyphenyl)amino-3-aminopyridine, and 3,4-diaminopyridine, and the addition salts thereof.

Other pyridine oxidation bases that are useful in the present disclosure are the 3-aminopyrazolo[1,5-a]pyridine oxidation bases or addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamino, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol,
and the addition salts thereof.

Among the pyrimidine derivatives that may be mentioned are the compounds described, for example, in patents DE 2 359 399; JP 88-169 571; JP 05-63124; EP 0 770 375 or patent application WO 96/15765, for instance 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and the addition salts thereof, and the tautomeric forms thereof, when a tautomeric equilibrium exists.

Among the pyrazole derivatives that may be mentioned are the compounds described in patents DE 3 843 892 and DE 4 133 957, and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl) amino-1-methylpyrazole, and the addition salts thereof.

The at least one additional oxidation base is present in the composition of the present disclosure in an amount ranging from 0.001% to 20% by weight, such as from 0.005% to 6%, relative to the total weight of the dye composition.

The composition according to the present disclosure may also comprise at least one coupler conventionally used for dyeing keratin fibers. Among these couplers, mention may be made, for example, of meta-phenylenediamines, meta-diphenols, naphthalene-based couplers and heterocyclic couplers, and the addition salts thereof.

Examples that may be mentioned include 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino)toluene, and the addition salts thereof.

In the composition of the present disclosure, the at least one coupler is present in an amount ranging from 0.001% to 20%, such as from 0.005% to 6%, by weight relative to the total weight of the dye composition.

In general, the addition salts of the oxidation bases and couplers that may be used in the context of the present disclosure are chosen, for example, from the addition salts with an acid, such as the hydrochlorides, hydrobromides, sulfates, citrates, succinates, tartrates, lactates, tosylates, benzenesulfonates, phosphates and acetates, and the addition salts with a base, such as sodium hydroxide, potassium hydroxide, ammonia, amines or alkanolamines.

The suitable dyeing medium, also known as the dye support, is a cosmetic medium generally comprising water or a mixture of water and at least one organic solvent to dissolve the compounds that are not sufficiently water-soluble. Examples of organic solvents that may be mentioned include $C_1$-$C_4$ lower alkanols, such as ethanol and isopropanol; polyols and polyol ethers, for instance 2-butoxyethanol, propylene glycol, propylene glycol monomethyl ether, diethylene glycol monoethyl ether and monomethyl ether, and also aromatic alcohols, for instance benzyl alcohol or phenoxyethanol, and mixtures thereof.

The solvents are, in at least one embodiment, present in amounts ranging from 1% to 40% by weight, such as from 5% to 30%, by weight relative to the total weight of the dye composition.

The dye composition in accordance with the present disclosure may also comprise at least one adjuvant conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric polymeric associative thickeners, antioxidants, penetrating agents, sequestering agents, fragrances, buffers, dispersants, conditioning agents, for instance volatile or nonvolatile, modified or unmodified silicones, film-forming agents, ceramides, preserving agents and opacifiers.

The above adjuvants are generally each present in an amount of from 0.01% to 20% by weight relative to the weight of the composition.

Needless to say, a person skilled in the art will take care to select this or these optional additional compound(s) such that the advantageous properties intrinsically associated with the oxidation dye composition in accordance with the invention are not, or are not substantially, adversely affected by the envisaged addition(s).

The pH of the dye composition in accordance with the present disclosure is generally from 3 to 12, such as from 5 to 11. It may be adjusted to the desired value by means of acidifying or basifying agents usually used for dyeing keratin fibers, or alternatively using standard buffer systems.

Among the acidifying agents that may be mentioned, for example, are mineral or organic acids such as hydrochloric acid, orthophosphoric acid, sulfuric acid, carboxylic acids, for instance acetic acid, tartaric acid, citric acid or lactic acid, and sulfonic acids.

Among the basifying agents that may be mentioned, for example, are aqueous ammonia, alkaline carbonates, alkanolamines such as monoethanolamine, diethanolamine and triethanolamine and derivatives thereof, sodium hydroxide, potassium hydroxide and the compounds of formula (II) below:

in which W is a propylene residue optionally substituted with a hydroxyl group or a $C_1$-$C_4$ alkyl radical; and $R_a$, $R_b$, $R_c$ and $R_d$, which may be identical or different, are chosen from a hydrogen atom and a $C_1$-$C_4$ alkyl or $C_1$-$C_4$ hydroxyalkyl radical.

The dye composition according to the present disclosure may be in various forms, such as in the form of liquids, creams or gels, or in any other form that is suitable for dyeing keratin fibers, such as human hair.

The process of the present disclosure is a dyeing process in which the composition according to the disclosure as defined above is applied to keratin fibers.

According to one embodiment, the dyeing composition is applied to the keratin fibers in the presence of an oxidizing agent for a period long enough to obtain the desired lightening. The oxidizing agent may be added to the dyeing composition just at the time of use, or it may be used in the form of an oxidizing composition containing it, which is applied simultaneously with or sequentially to the dyeing composition.

According to one embodiment, the composition according to the present disclosure comprises at least one oxidation dye precursor.

The mixture obtained is then applied to the keratin fibers. After a leave-in time ranging from 3 minutes to 1 hour, such as from 5 to 50 minutes, the keratin fibers are rinsed, washed with shampoo, rinsed again and then dried.

The oxidizing agents conventionally used for the oxidation dyeing of keratin fibers are, for example, hydrogen peroxide, urea peroxide, alkali metal bromates, persalts such as perborates and persulfates, peracids and oxidase enzymes, among which mention may be made of peroxidases, two-electron oxidoreductases such as uricases, and four-electron oxygenases, for instance laccases. In at least one embodiment, the oxidizing agent is hydrogen peroxide.

The oxidizing composition may also contain various adjuvants conventionally used in compositions for dyeing the hair and as defined above.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the embodiments disclosed herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosed embodiments are approximations, unless otherwise indicated the numerical values set forth in the specific examples are reported as precisely as possible. Any numerical value, however, inherently contain certain errors necessarily resulting from the standard deviation found in their respective testing measurements.

The examples that follow serve to illustrate the invention without, however, being limiting in nature.

EXAMPLES

Example 1

Synthesis of 4-{(E)-[methyl(phenyl)hydrazono]methyl}-1-[3-(4-{(E)-[methyl(phenyl)hydrazono]methyl}pyridinium-1-yl)propyl]pyridinium dibromide

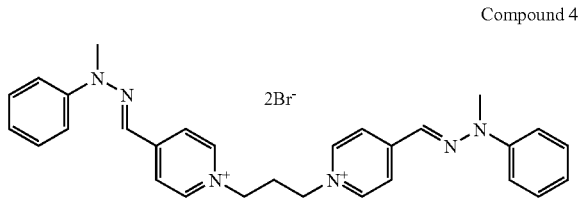

Compound 4

Step 1: Synthesis of isonicotinaldehyde methyl(phenyl)hydrazone

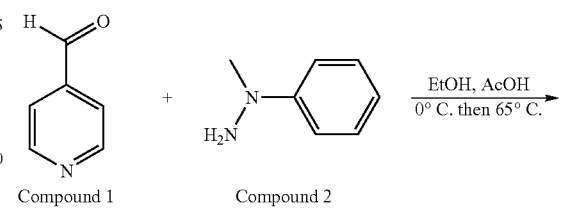

Compound 1    Compound 2

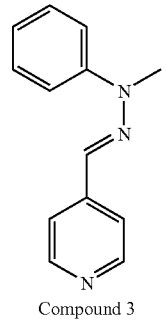

Compound 3

One equivalent of methyl phenylhydrazine (58.76 g; 0.4809 mol, compound 2) was diluted in 50 ml of ethanol and 1.5 ml of acetic acid in a three-necked flask on which was mounted a condenser. The reaction medium was then stirred at 0° C. Using a dropping funnel, 1 equivalent of 4-pyridinecarboxaldehyde (51.5 g; 0.4808 mol, compound 1) was added. After addition of the aldehyde, the reaction medium was heated at 65° C. (oilbath temperature) for 13 hours.

Next, the reaction medium (dark oil) was poured into a water-ice mixture (1/3). The mixture was then stirred. The oily product darkened until a yellow powder was obtained. This powder was then filtered off and washed several times with water. After drying, 83.9 g of compound 3 were obtained.

Analytical Data:
Yellow Powder.
NMR ($^1$H, MeOD, 400 MHz): 3.45 ppm, 3H, s; 6.94-6.98 ppm, 1H, m; 7.32-7.35 ppm, 2H, m; 7.44-7.47 ppm, 2H, m; 7.60-7.63 ppm, 3H, m; 8.53-8.55 ppm, 2H, m NMR ($^{13}$C, DMSO-d6, 100, 62 MHz): 35.59 ppm; 115.62 ppm; 120.29 ppm; 121.46 ppm; 129.45 ppm; 130.02 ppm; 144.08 ppm; 147.31 ppm; 150.31 ppm Mass (MS ES+): m/z=212

Step 2

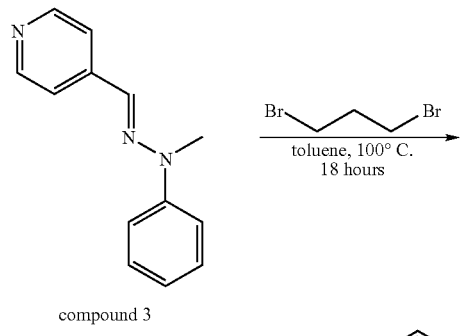

compound 3

Compound 3 (10 g, 0.047 mol) in the presence of 2.40 ml of 1,3-dibromopropane (0.023 mol) in 200 ml of toluene was stirred at 100° C. for 18 hours in a three-necked flask on which was mounted a condenser.

After the reaction, the reaction medium was cooled to room temperature and the desired product that precipitated was filtered off and then cleaned with ethyl acetate and finally dried. A reprecipitation was necessary and was performed as follows: the crude reaction product was dissolved in 150 ml of methanol. Over a very short period, a further 550 ml of ethyl acetate were added, causing the expected product to precipitate. This product was filtered off and then dried under vacuum. 10.1 g of compound 4 were recovered (yellow powder).

Analyses of the Product:
NMR (1H, 400 MHz, CD3OD):

| 2.77 | m | CH2 |
| 3.6 | d | 2 × CH3 |
| 4.7 | t | 2 × CH2 |
| 7.15 | m | 2 H |
| 7.4 | m | 4 H |
| 7.51 | m | 4 H |
| 7.66 | bs | 2 H |
| 8.11 | m | 4 H |
| 8.71 | m | 4 H |

Mass (LC/MS; ESI+): the expected dication $[C_{29}H_{32}N_6]^{2+}$ was detected at m/z, ESI+=232.

Example 2

Synthesis of 4-{(E)-[methyl(phenyl)hydrazono]methyl}-1-[4-(4-{(E)-[methyl(phenyl)hydrazono]methyl}pyridinium-1-yl)butyl]pyridinium dibromide

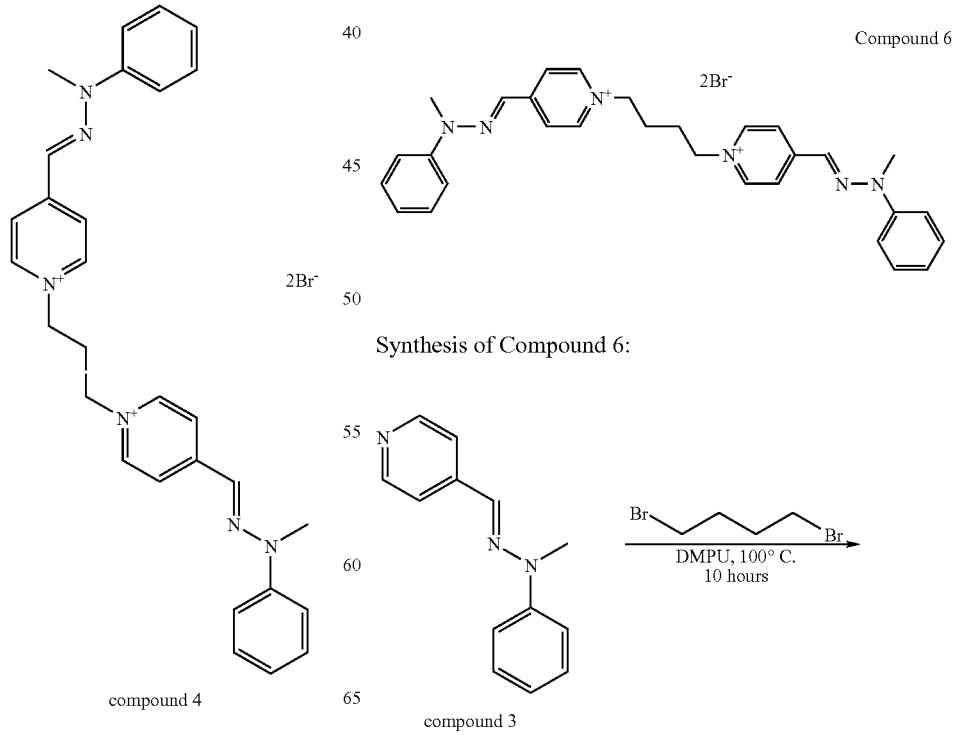

Compound 6

Synthesis of Compound 6:

compound 3

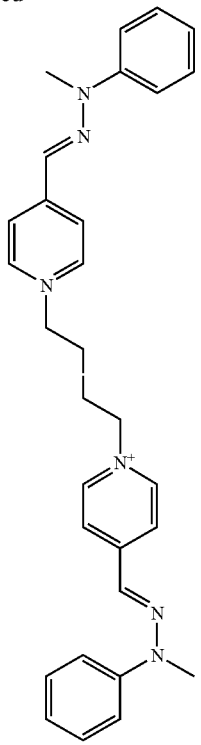

compound 6

Compound 3 (10 g, 0.047 mol) was stirred at 100° C. for 10 hours in the presence de 2.82 ml of 1,4-dibromobutane (0.023 mol) in 200 ml of 1,3-dimethyl-3,4,5,6-tetrahydro-2(1H)-pyrimidinone in a three-necked flask on which was mounted a condenser.

After the reaction, the reaction medium was cooled to room temperature and the desired product that precipitated was filtered off and then rinsed with ethyl acetate and finally dried. Reprecipitation was necessary and was performed as follows: the crude reaction product was dissolved in 150 ml of methanol. Over a very short period, a further 550 ml of ethyl acetate were added, causing the expected product to precipitate. This product was filtered off and then dried under vacuum. 12.4 g of compound 6 were recovered (yellow powder).

Analyses of the Product:
NMR (1H, 400 MHz, CD3OD):

| 2.15 | m | 2 CH2 |
| 3.65 | m | 2 CH3 |
| 4.58 | m | 2 CH2 |
| 7.17 | m | 2 H |
| 7.43 | m | 4 H |
| 7.58 | m | 4 H |
| 7.72 | bs | 2 H |
| 8.15 | m | 4 H |
| 8.71 | m | 4 H |

Mass (ESI+): the expected dication $[C_{30}H_{34}N_6]^{2+}$ was detected at m/z, ESI+=239.

Example 3

Synthesis of 4-{(E)-[methyl(phenyl)hydrazono]methyl}-1-[5-(4-{(E)-[methyl(phenyl)hydrazono]methyl}pyridinium-1-yl)pentyl]pyridinium dibromide Compound 8

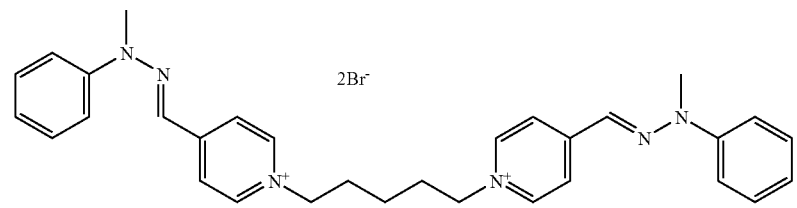

Synthesis of Compound 8:

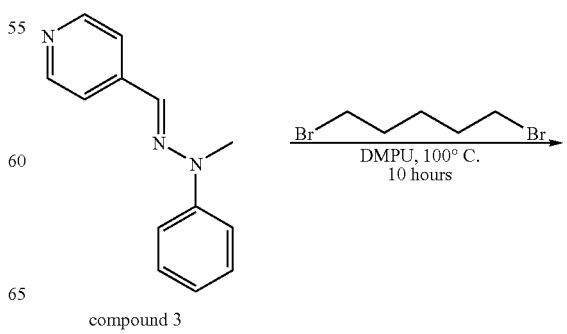

compound 3

-continued

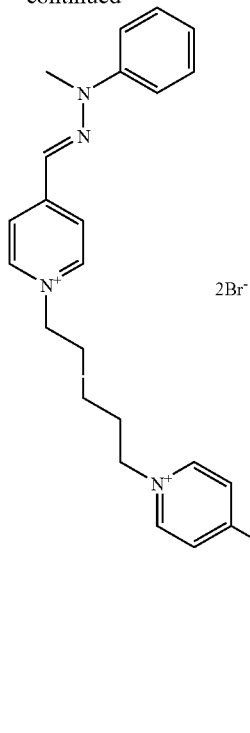

compound 8

| | | |
|---|---|---|
| 1.5 | m | CH2 |
| 2.09 | m | 2 CH2 |
| 3.61 | d | 2 CH3 |
| 4.52 | t | 2 CH2 |
| 7.14 | m | 2 H |
| 7.41 | m | 4 H |
| 7.53 | m | 4 H |
| 7.69 | bs | 2 H |
| 8.13 | d | 4 H |
| 8.71 | d | 4 H |

Mass (ESI+): the expected dication $[C_{31}H_{36}N_6]^{2+}$ was detected at m/z, ESI+=246.

Example 4

Synthesis of 4-{(E)-[methyl(phenyl)hydrazono]methyl}-1-[6-(4-{(E)-[methyl(phenyl)hydrazono]methyl}pyridinium-1-yl)hexyl]pyridinium dibromide

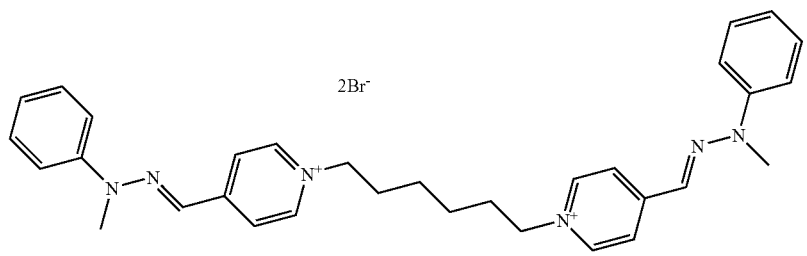

Compound 10

Compound 3 (10 g, 0.047 mol) was stirred at 100° C. for 10 hours in the presence of 3.22 ml of 1,5-dibromopentane (0.023 mol) in 100 ml of 1,3-dimethyl-3,4,5,6-tetrahydro-2 (1H)-pyrimidinone in a three-necked flask on which was mounted a condenser.

After the reaction, the reaction medium was cooled to room temperature and the expected product was precipitated in the presence of 20 ml of ethyl acetate, filtered off and dried. Reprecipitation was necessary and was performed as follows: the crude reaction product was dissolved in 150 ml of methanol. Over a very short period, a further 550 ml ethyl acetate were added, causing the expected product to precipitate. This product was filtered off and then dried under vacuum. 12.4 g of compound 8 were recovered (yellow powder).

Analyses of the Product:

NMR (1H, 400 MHz, CD$_3$OD):

Synthesis of Compound 10:

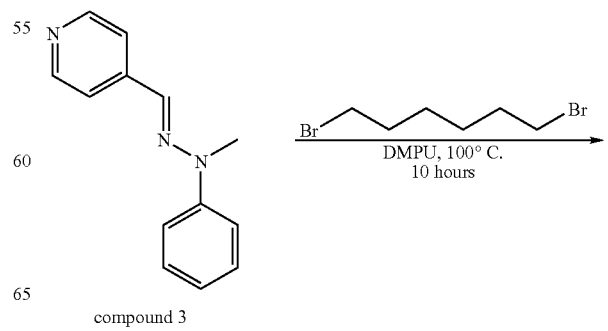

compound 3

-continued

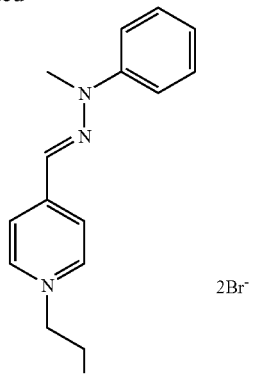

compound 10

Compound 3 (10 g, 0.047 mol) was stirred at 100° C. for 10 hours in the presence of 3.61 ml of 1,6-dibromohexane (0.023 mol) in 100 ml of 1,3-dimethyl-3,4,5,6-tetrahydro-2(1H)-pyrimidinone in a three-necked flask on which was mounted a condenser.

After the reaction, the reaction medium was cooled to room temperature and the desired product was precipitated in the presence of 20 ml of ethyl acetate and then filtered off and finally dried. Reprecipitation was necessary and was performed as follows: the crude reaction product was dissolved in 150 ml of methanol. Over a very short period a further 550 ml of ethyl acetate were added, causing the expected product to precipitate. This product was filtered off and then dried under vacuum. 11.2 g of compound 10 were recovered (yellow powder).

Analytical Data:

NMR (1H 400 MHz, CD$_3$OD):

| 1.51 | m | 2 × CH2 |
|------|---|---------|
| 2.04 | m | 2 × CH2 |
| 3.63 | s | 2 × CH3 |
| 4.51 | t | 2 × CH2 |
| 7.14 | m | 2 H |
| 7.41 | m | 4 H |
| 7.55 | m | 4 H |
| 7.7  | s | 2 H |
| 8.13 | d | 4 H |
| 8.72 | d | 4 H |

Mass (ESI+):

the expected dication $(C_{32}H_{38}N_6)^{2+}$ was detected at m/z=254.

Example 5

Synthesis of 4-{(E)-[methyl(phenyl)hydrazono]methyl}-1-(6-{[4-({[6-(4-{(E)-[methyl(phenyl)hydrazono]methyl}pyridinium-1-yl)hexyl]amino}carbonyl)benzoyl]amino}hexyl)pyridinium dibromide

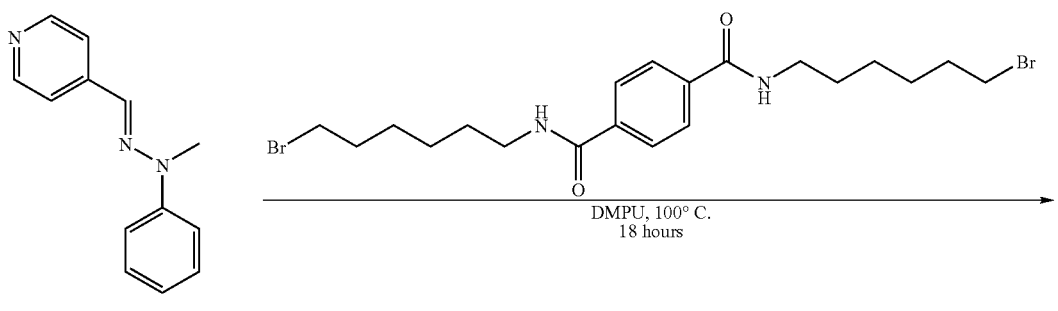

compound 3

-continued

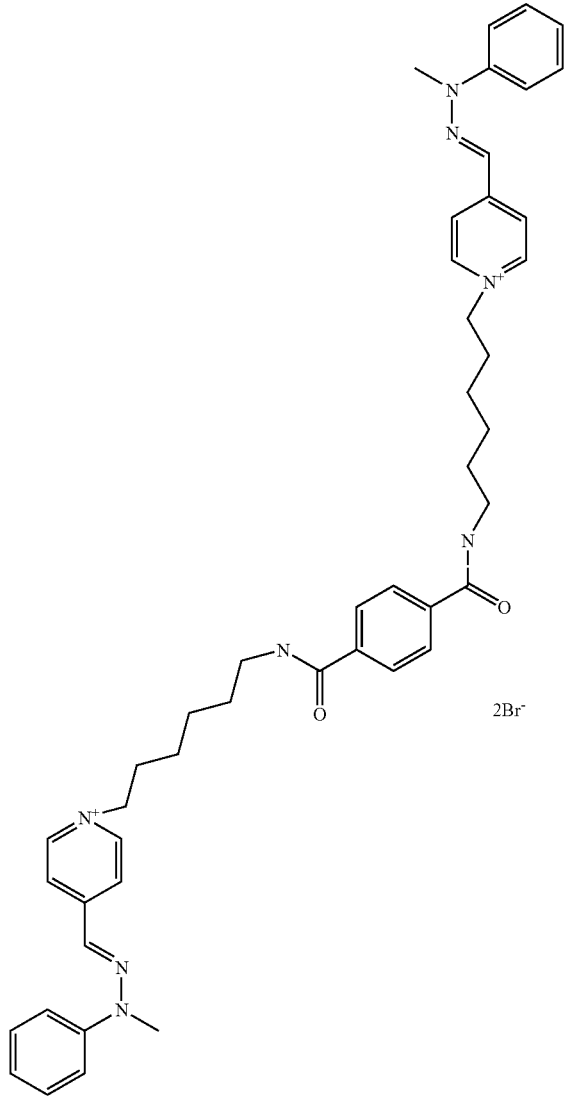

compound 12

Compound 3 (10 g, 0.047 mol) was stirred at 100° C. for 18 hours in the presence of 3.02 g of N,N"-bis(6-bromohexyl) terephthalamide (0.023 mol) in 200 ml of 1,3-dimethyl-3,4,5,6-tetrahydro-2(1H)-pyrimidinone in a three-necked flask on which was mounted a condenser.

After the reaction, the reaction medium was cooled to room temperature and the desired product was precipitated by adding 200 ml of ethyl acetate. The precipitate was filtered off and then dried. Reprecipitation was necessary, and was performed as follows: the crude reaction product was dissolved in 150 ml of methanol. Over a very short period, a further 550 ml of ethyl acetate were added, causing the expected product to precipitate. This product was filtered off and then dried under vacuum. 14.1 g of compound 12 were recovered (yellow powder).

Analyses of the Product:

NMR (1H. 400 MHz, CD3OD):

| 1.48 | m | 4 CH2 |
| 1.67 | m | 2 CH2 |
| 2.03 | m | 2 CH2 |
| 3.32 | d | 2 CH2 |
| 3.63 | s | 2 CH3 |
| 4.48 | t | 2 CH2 |
| 7.13 | m | 2 H |
| 7.4 | m | 4 H |
| 7.51 | m | 4 H |
| 7.66 | bs | 2 H |
| 7.87 | s | 4 H |
| 8.09 | d | 4 H |
| 8.64 | d | 4 H |

Mass (ESI+): The dication $[C_{46}H_{56}N_8O_2]^{2+}$ was detected at m/z=376.

Example 6

Synthesis of 4-{(E)-[methyl(phenyl)hydrazono]methyl}-1-[6-(4-{(E)-[methyl(phenyl)hydrazono]methyl}quinolinium-1-yl)hexyl]quinolinium dibromide

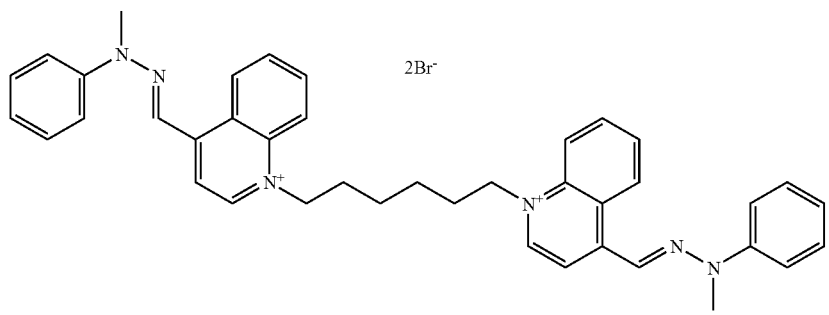

Compound 16

Step 1: Synthesis of quinoline-4-carbaldehyde methyl(phenyl)hydrazone

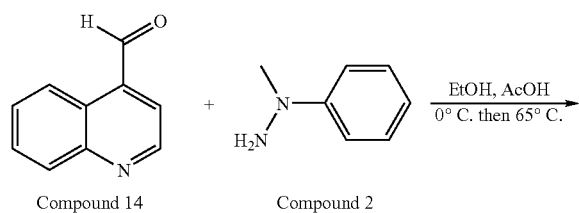

Compound 14        Compound 2

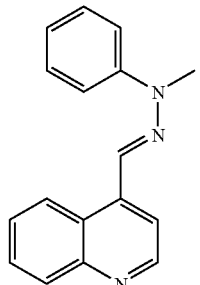

Compound 15

One equivalent of methylphenylhydrazine (4.1 g; 0.033 mol, compound 2 was diluted in 25 ml of ethanol and 0.5 ml of glacial acetic acid in a three-necked flask on which was mounted a condenser. The reaction medium was then stirred at 0° C. 1 equivalent of 4-formylquinoline (5.28 g; 0.033 mol, compound 14) was added by spatula. After adding the aldehyde, the reaction medium was heated at 70° C. (oil bath temperature) for 4 hours.

Next, the reaction medium (dark oil) was poured into a water-ice mixture (1/3). The mixture was then stirred. The oily product gradually darkened until an orange-yellow powder was obtained. This powder was then filtered and washed several times with water. After drying, 7.9 g of compound 15 were obtained.

Analytical Data:

NMR (1H, 400 MHz, CD$_3$OD):

| | | |
|---|---|---|
| 3.58 | d | CH3 |
| 7.01 | m | 1 H |
| 7.36 | m | 2 H |
| 7.48 | m | 2 H |
| 7.65 | m | 1 H |
| 7.76 | m | 1 H |
| 7.92 | d | 1 H |
| 8.01 | m | 1 H |
| 8.16 | bs | 1 H |
| 8.69 | d | 1 H |
| 8.75 | d | 1 H |

Mass (MS ES+): The quasi-molecular ion (MH)$^+$ of the expected molecule, C17H15N3, was mainly detected at m/z=262.

Step 2: Synthesis of 4-{(E)-[methyl(phenyl)hydrazono]methyl}-1-[6-(4-{(E)-[methyl(phenyl)hydrazono]methyl}quinolinium-1-yl)hexyl]quinolinium dibromide

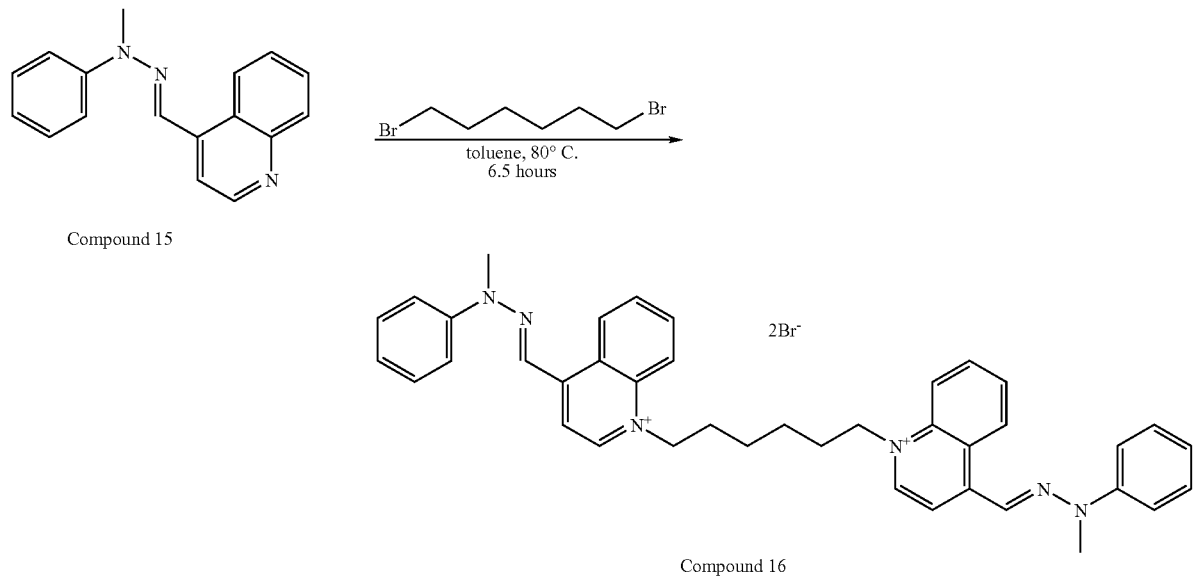

Compound 15 (1 g, 3.82 mmol) was stirred at 80° C. for 6.5 hours in the presence of 3.7 ml of 1,6-dibromohexane (23.96 mmol) in 23 ml of toluene in a three-necked flask on which was mounted a condenser.

After the reaction, the reaction medium was cooled to room temperature and then poured onto acetone (50 ml). The precipitate obtained was filtered off and then washed several times with acetone and finally dried under vacuum. 73 mg of compound 16 were recovered (orange powder).

Analyses of the Product:
NMR (1H, 400 MHz, CD3OD):

| | | |
|---|---|---|
| 1.06 | m | 2 × CH2 |
| 1.92 | m | 2 × CH2 |
| 3.8 | s | 2 × CH3 |
| 4.92 | t | 2 × CH2 |
| 7.19 | m | 2 H |
| 7.46 | m | 4 H |
| 7.68 | m | 4 H |
| 7.99 | t | 2 H |
| 8.2 | t | 2 H |
| 8.39 | d | 2 H |
| 8.48 | m | 2 H |
| 8.49 | m | 2 H |
| 9.09 | m | 2 H |
| 9.13 | d | 2 H |

Mass (LC/MS: ESI+): The expected dication ($C_{40}H_{42}N_6$) 2+, was detected at m/z=303.

Example 7

Synthesis of 4-{(E)-[methyl(phenyl)hydrazono]methyl}-1-[6-(4-[{(E)-[methyl(phenyl)hydrazono]methyl}pyridinium-1-yl)hexyl]quinolinium dibromide

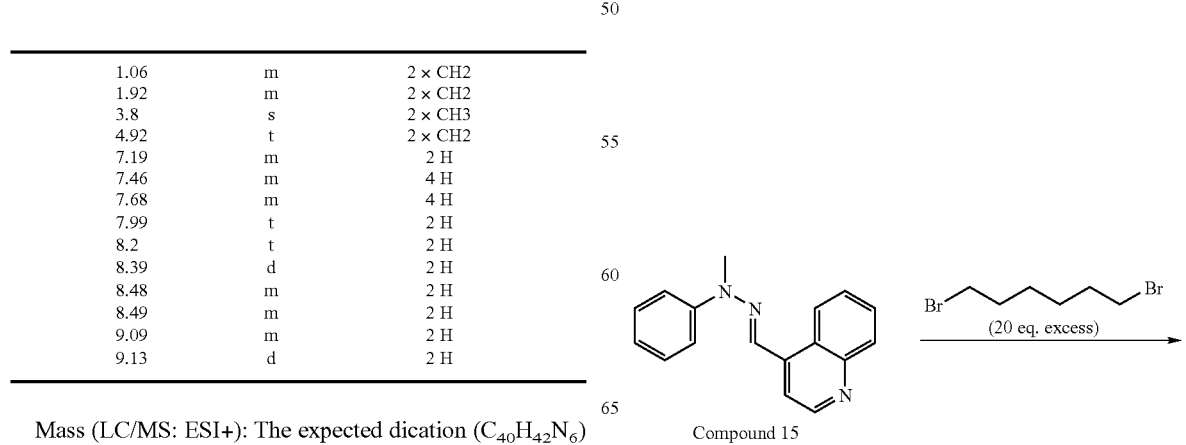

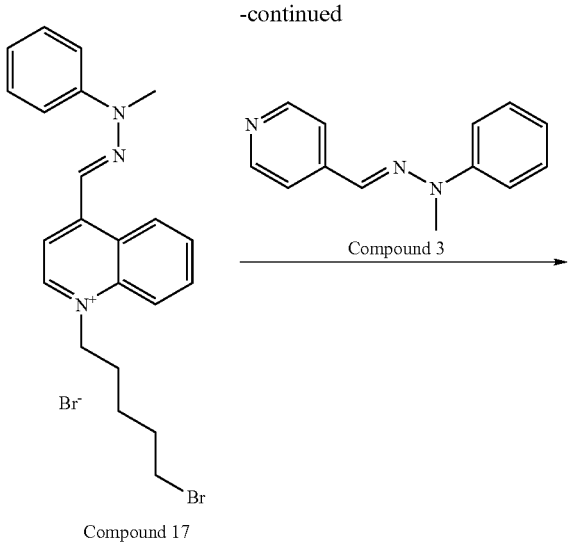

Compound 17

Compound 3

Compound 18 of ethanol were added to the reaction medium, preheated to 50° C., with stirring. The reaction medium was maintained at 50° C. for 48 hours.

After the reaction, compound 18 was precipitated by adding 75 ml of cold ethyl acetate. The precipitate obtained was filtered off and then rinsed with 25 ml of ethyl acetate. 1.2 g of a red powder were obtained after drying in a desiccator under vacuum.

Mass (ESI+): the expected dication was detected at m/z=278.

Example 8

Synthesis of 1-methyl-3-[5-(1-methyl-2-{(E)-[methyl(phenyl)hydrazono]methyl}-1H-imidazol-3-ium-3-yl)pentyl]-2-{(E)-[methyl(phenyl)hydrazono]methyl}-1H-imidazol-3-ium dibromide

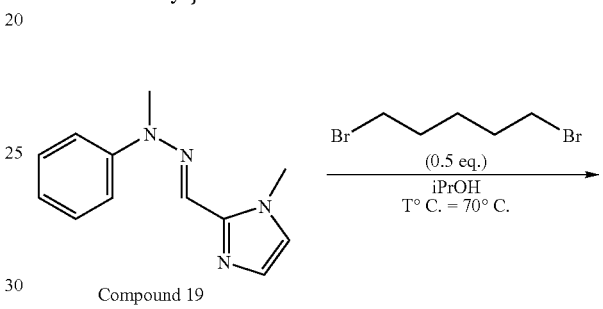

Compound 19

Compound 20

Compound 15 (5.83 g) was stirred at 80° C. for 6 hours in the presence of 1,6-dibromohexane (70 ml) in a three-necked flask on which was mounted a condenser.

After reaction, an orange precipitate was obtained. The reaction medium was filtered while hot through a sinter funnel. The precipitate obtained was washed several times with toluene and then with petroleum ether and finally dried under vacuum. 7.47 g of compound 17 were recovered (orange powder).

1.19 g (1 eq, 2.3 mmol) of compound 17 were dissolved in 5 ml of ethanol in a three-necked flask. Using a dropping funnel, 1 g (2 eq, 4.6 mmol) of compound 3 dissolved in 10 ml Compound 19 (0.15 g) was stirred at 70° C. for 48 hours in the presence of 1,5-dibromopentane (80 mg) and 1 ml of isopropanol in a three-necked flask on which was mounted a condenser.

After the reaction, compound 20 was precipitated by adding 5 ml of cold ethyl acetate. The precipitate obtained was filtered off and rinsed with 2×5 ml of ethyl acetate. 90 mg of a yellow powder were obtained after drying in a desiccator under vacuum.

Mass (ESI+): the expected dication was detected at m/z=249.

Example 9

Synthesis of 1-methyl-3-[4-(1-methyl-2-{(E)-[methyl(phenyl)hydrazono]methyl}-1H-benzimidazol-3-ium-3-yl)butyl]-2-{(E)-[methyl(phenyl)hydrazono]methyl}-1H-benzimidazol-3-ium dibromide

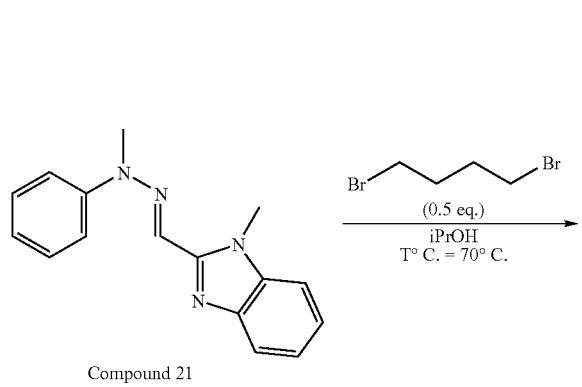

Example 10

Synthesis of 1-[6-(1-methyl-2-{(E)-[methyl(phenyl)hydrazono]methyl}-1H-imidazol-3-ium-3-yl)hexyl]-4-{(E)-[methyl(phenyl)hydrazono]methyl}quinolinium dibromide

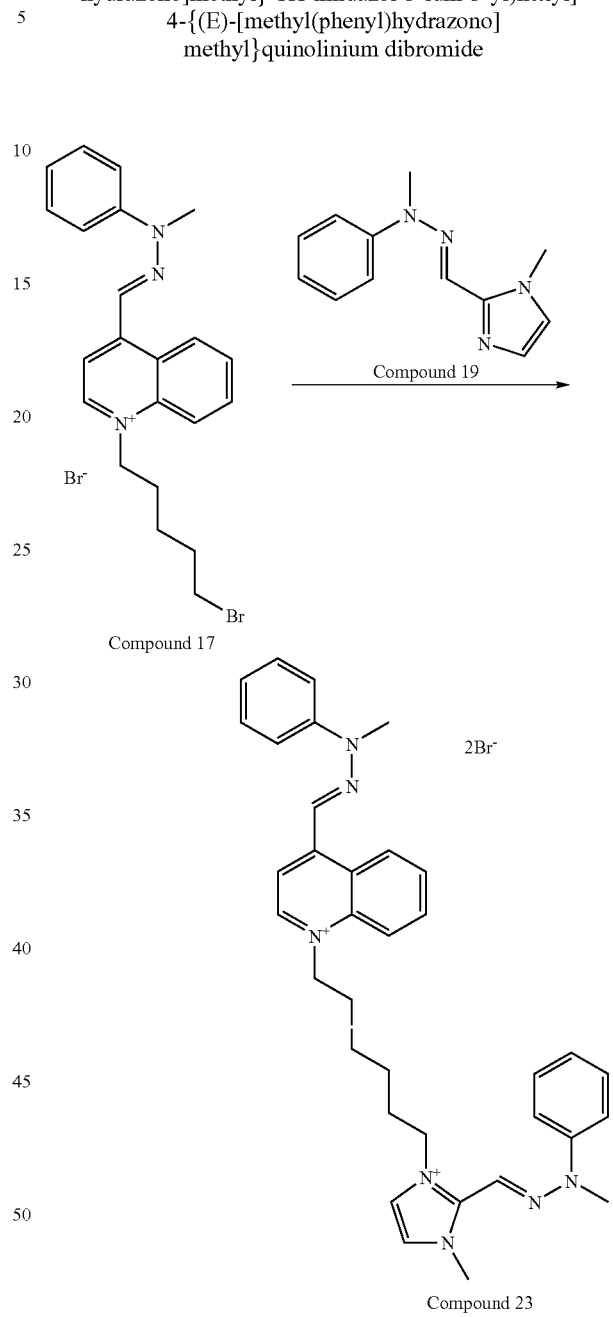

Compound 21 (0.15 g) was stirred at 70° C. for 48 hours in the presence of 1,4-dibromobutane (61 mg) and 1 ml of isopropanol in a three-necked flask on which was mounted a condenser.

After the reaction, compound 22 was precipitated by adding 5 ml of cold ethyl acetate. The precipitate obtained was filtered off and then rinsed with 2×5 ml of ethyl acetate. 77 mg of a yellow powder were obtained after drying in a desiccator under vacuum.

Mass (ESI+): the expected dication was detected at m/z=292.

Compound 17 (0.26 g) was stirred at 70° C. for 48 hours in the presence of compound 19 (120 mg) and 2 ml of isopropanol in a three-necked flask on which was mounted a condenser.

After the reaction, compound 23 was precipitated by adding 5 ml of cold ethyl acetate. The precipitate obtained was filtered off and then rinsed with 2×5 ml of ethyl acetate. 125 mg of a yellow powder were obtained after drying in a desiccator under vacuum.

Mass (ESI+): the expected dication was detected at m/z=280.

Example 11

Synthesis of 1-[6-(1-methyl-2-{(E)-[methyl(phenyl)hydrazono]methyl}-1H-benzimidazol-3-ium-3-yl)hexyl]-4-{(E)-[methyl(phenyl)hydrazono]methyl]quinolinium dibromide

Example 12

Synthesis of the Compound [25]: 1,1'-pentane-1,5-diylbis(4-{(E)-[methyl(phenyl)hydrazono]methyl}quinolinium) dibromide

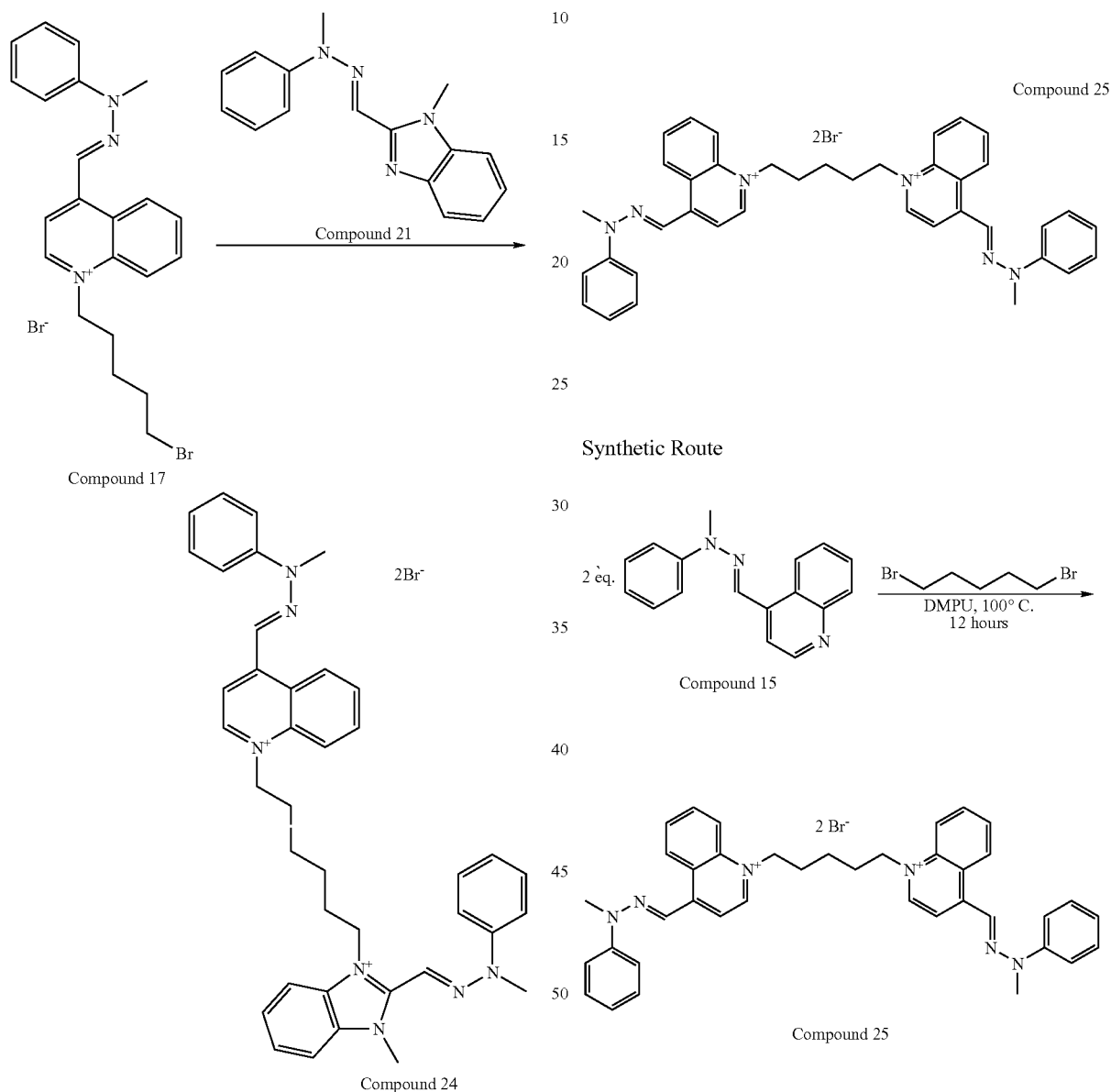

Compound 17 (0.21 g) was stirred at 70° C. for 48 hours in the presence of compound 21 (120 mg) and 2 ml of isopropanol in a three-necked flask on which was mounted a condenser.

After the reaction, compound 24 was precipitated by adding 5 ml of cold ethyl acetate. The precipitate obtained was filtered off and then rinsed with 2×5 ml of ethyl acetate. 111 mg of a yellow powder were obtained after drying in a desiccator under vacuum.

Mass (ESI+): the expected dication was detected at m/z=305.

In a three neck flask fitted with a mechanical stirrer, [15] (1 g; 3.82 mmoles) was dissolved in DMPU (20 ml); 0.26 ml of 1,5-dibromohexane (1.91 mmoles) and then was heated at 100° C. The color of the reaction mixture became very dark orange. The reaction mixture was heated at 100° C. overnight and then cooled down to room temperature. Acetone (50 ml) and ethyl acetate (50 ml) were added slowly, and a precipitate gradually formed. The precipitate was filtered off, rinsed with acetone and dried under vacuum to give a orange powder of [25] (0.75 g).

Standard analytical characterization was in agreement with the structure.

Example 13

Synthesis of the Compound [26]: 1,1'-butane-1,4-diylbis(4-{(E)[methyl(phenyl)hydrazono]methyl}quinolinium) dibromide

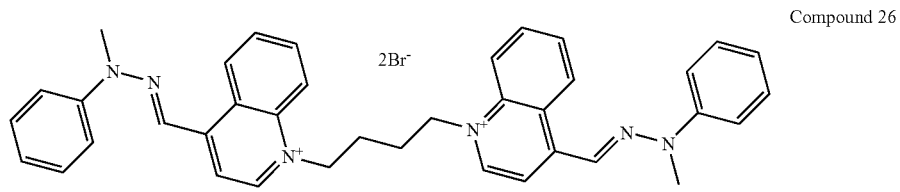

Compound 26

Synthetic Route

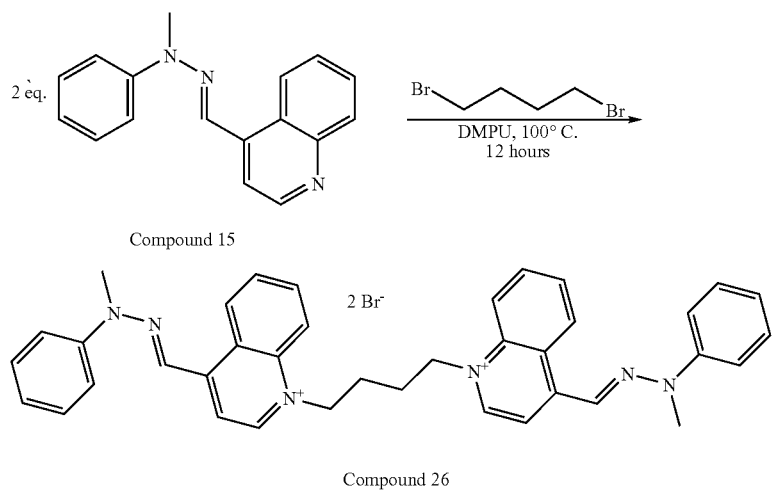

In a three neck flask fitted with a mechanical stirrer, [15] (1 g; 3.82 mmoles) was dissolved in DMPU (20 ml); 0.23 ml of 1,4-dibromobutane (1.91 mmoles) and then was heated at 100° C. The color of the reaction mixture became very dark orange. The reaction mixture was heated at 100° C. overnight and then cooled down to room temperature. Acetone (50 ml) and ethyl acetate (50 ml) were added slowly, and a precipitate gradually formed. The precipitate was filtered off, rinsed with acetone and dried under vacuum to give a orange powder of [26] (0.65 g).

Standard analytical characterization was in agreement with the structure.

Example 14

Synthesis of the Compound [27]: 1,1'-propane-1,3-diylbis(4-{(E)-[methyl(phenyl)hydrazono]methyl}quinolinium) dibromide

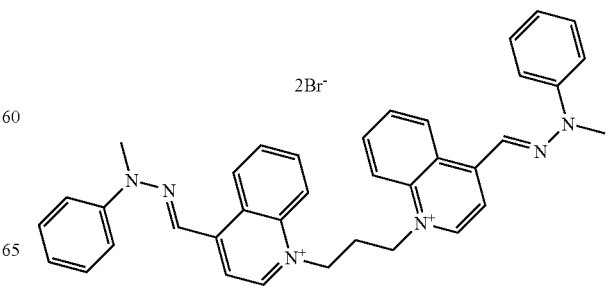

Compound 27

Synthetic Route

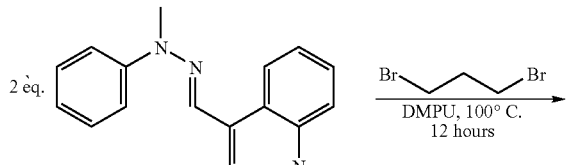

Compound 15

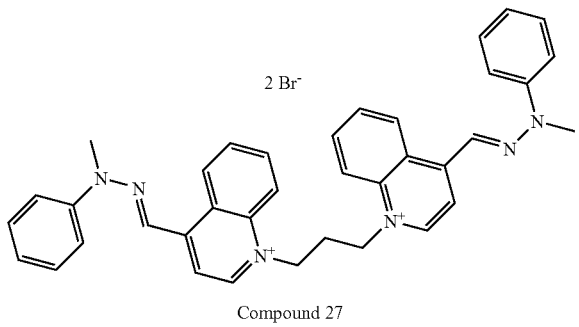

Compound 27

In a three neck flask fitted with a mechanical stirrer, [15] (1 g; 3.82 mmoles) was dissolved in DMPU (20 ml); 0.20 ml of 1,3-dibromopropane (1.91 mmoles) and then was heated at 100° C. The color of the reaction mixture became very dark orange. The reaction mixture was heated at 100° C. overnight and then cooled down to room temperature. Acetone (50 ml) and ethyl acetate (50 ml) were added slowly, and a precipitate gradually formed. The precipitate was filtered off, rinsed with acetone and dried under vacuum to give a orange powder of [27] (0.81 g).

Standard analytical characterization was in agreement with the structure.

Example 15

Synthesis of the Compound [33]: 2-{(E)-[{4-[(4-methoxyphenyl)(methyl)amino]phenyl}(methyl)hydrazono]methyl}-3,3-dimethyl-1-[6-(4-{(E)-[methyl(phenyl)hydrazono]methyl}pyridinium-1-yl)hexyl]-3H-indolium dichloride Compound 33

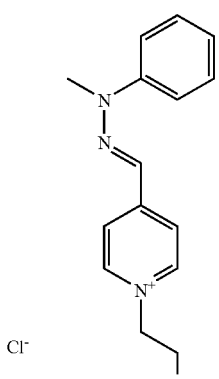

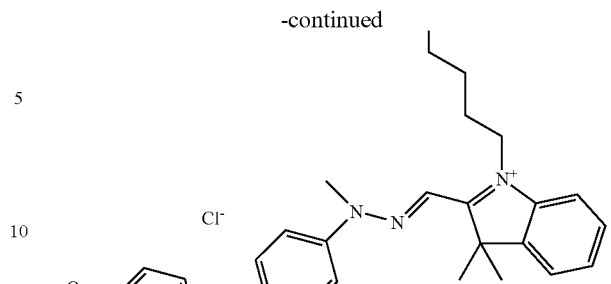

Step 1: Synthesis of the Compound [28]

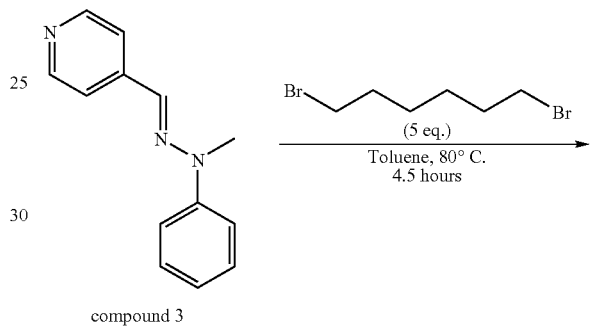

compound 3

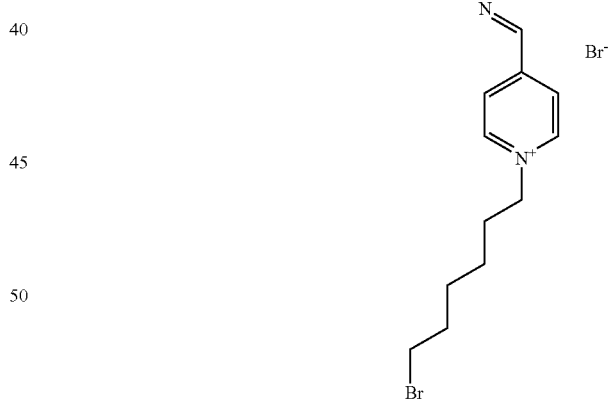

compound 28

In a three neck flask fitted with a mechanical stirrer, [3] (80.1 g; 0.379 moles) was dissolved in toluene (250 ml); The reaction mixture was heated at 80° C. 302 ml of 1,6-dibromohexane (1.94 moles) diluted in toluene were added to the reaction mixture; the color of the reaction mixture became very dark yellow. The reaction mixture was heated at 80° C. during 4,5 hours and then cooled down to room temperature. A precipitate gradually formed during the reaction. The precipitate was filtered off, rinsed with toluene and petroleum ether and filtered off again.

The solid was then solubilized in dichloromethane (1 L) and washed 4 times with water. The organic phase was dried over MgSO$_4$, filtrate, and the solvent was removed in vacuo to yield 95.1 g of a deep yellow powder [28]

Standard analytical characterization was in agreement with the structure.

Step 2: Synthesis of the Compound [30]

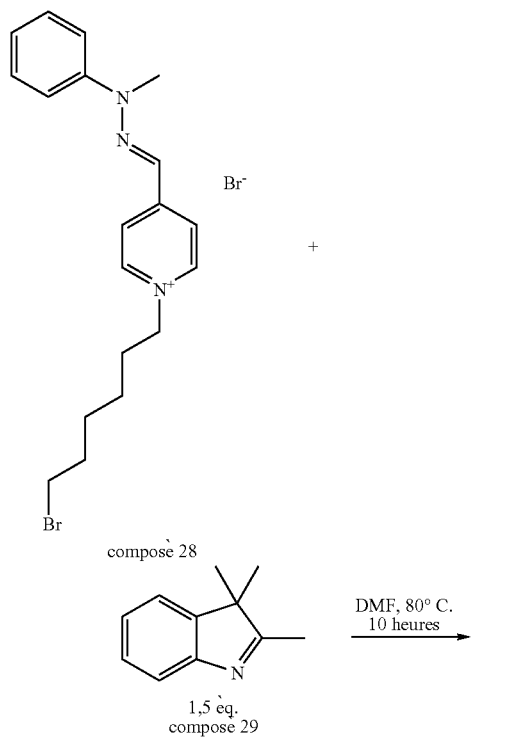

In a three neck flask fitted with a mechanical stirrer, [28] (10 g; 21.96 mmoles) and [29] (5,3 ml; 33.02 mmoles) were dissolved in DMF (10 ml); the reaction mixture was heated at 80° C. during 10 hours and then cooled down to room temperature. A crude oil was obtained after adding diethyl ether. After separation, the crude oil was diluted in iPrOH. A precipitate gradually formed when the alcoholic phase was added slowly to a diethyl ether solution. The precipitate was filtered off to give a red powder of [30] (12.31 g).

Standard analytical characterization was in agreement with the structure.

Step 3: Synthesis of the Compound [32]

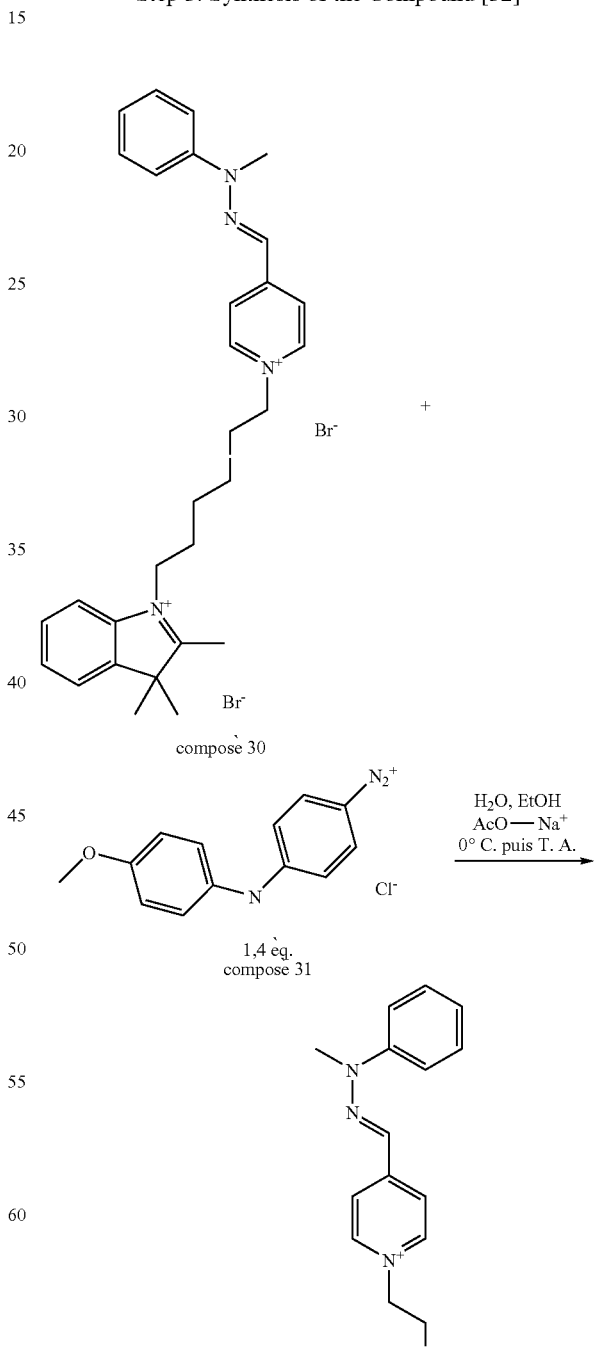

-continued

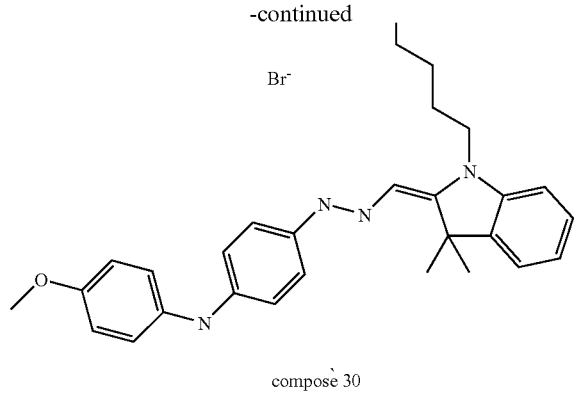

composé 30

In a three neck flask fitted with a mechanical stirrer, [30] (7.24 g; 0.013 mole) was dissolved in water (270 ml) and ethanol (400 ml). The reaction mixture was cooled at 0° C. Compound [31] (4.38 g) was slowly added to the reaction mixture adjusting the pH to 5.7 by dropwise addition of sodium acetate; the reaction mixture was stirred at 0° C. for 4.5 hours. Then, the cooling bath was removed and pH was adjusted to 11 by dropwise addition of 40% aqueous sodium hydroxide. A precipitate formed, was filtered off, rinsed with water and dried over $P_2O_5$ under vacuum overnight to give a black powder of [32] (8.79 g).

Standard analytical characterization was in agreement with the structure.

Step 4: Synthesis of the Compound [33]

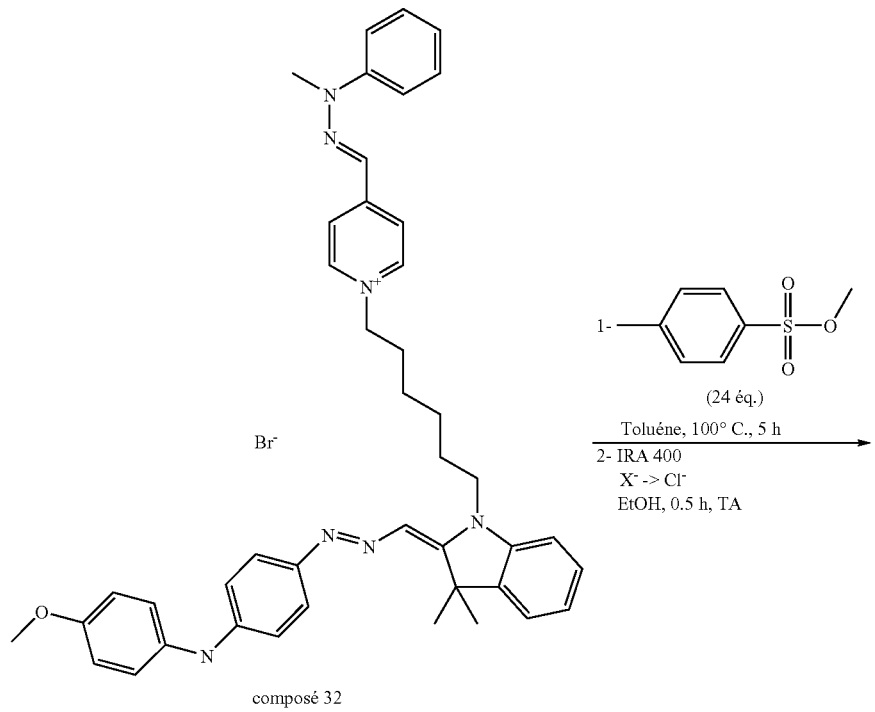

composé 32

-continued

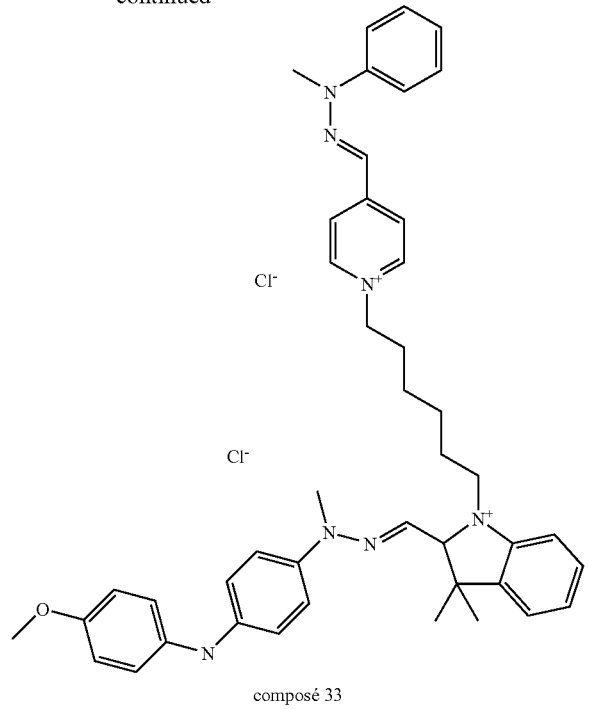

composé 33

In a three neck flask fitted with a mechanical stirrer, [32] (0.2 g; 0.26 mmole) and p-toluene sulfonic acid methyl ester (1.18 g) were dissolved in toluene (5 ml). The reaction mixture was heated at 100° C. for 5 hours. After reaction, the solvent was removed in vacuo. The crude solid was solubilized in ethanol (50 ml) and Amberlyst resin (IRA 400) was added (10 g) to the mixture reaction. The reaction mixture was stirred at room temperature for 0.5 hour. After filtration, the solvent was removed in vacuo and the solid rinsed with diethyle oxide, and dried over $P_2O_5$ under vacuum overnight to give a black powder of [33] (0.21 g).

Example 16

Synthesis of the Compound [36]: 1,1'-hexane-1,6-diylbis(2-{(E)-[{4-[(4-methoxyphenyl)(methyl)amino]phenyl}(methyl)hydrazono]methyl}-3,3-dimethyl-3H-indolium) dichloride

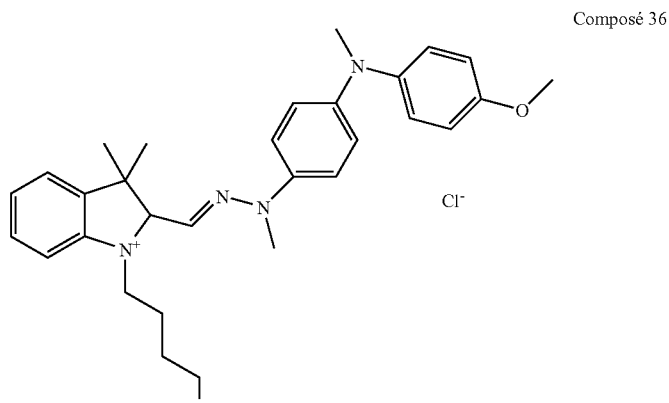

Composé 36

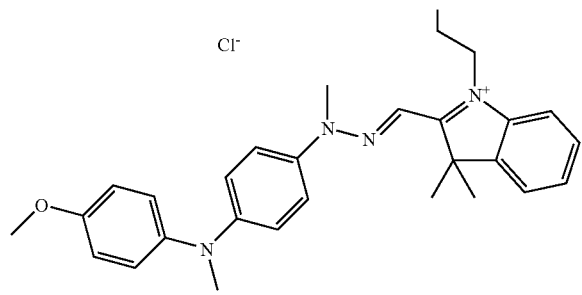
Step 1: Synthesis of the Compound [34]
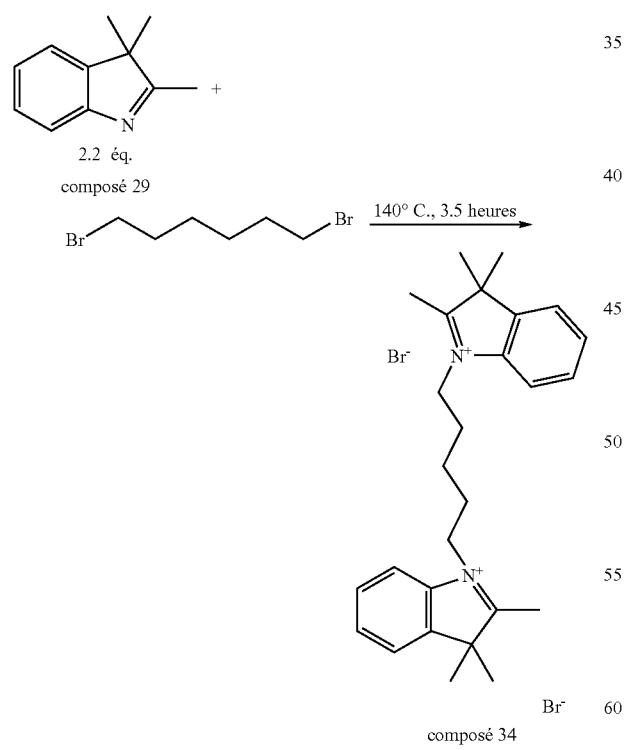

Ref: F. Ribes, R. Guglielnetti, J. Metzger, Bulletin de la Société Chimique de France, 1972, n °1, 143-147.

In a three neck flask fitted with a mechanical stirrer, [29] (11 ml; 68.52 mmoles) was reacted with 1,6-dibromohexane (4.8 ml; 31.2 mmoles); The reaction mixture was heated at 140° C. for 3.5 hours; the color of the reaction mixture became very dark red. The reaction mixture was cooled down to room temperature. A precipitate gradually formed after adding acetone. The precipitate was filtered off, then solubilized in isopropanol. A precipitate gradually formed when the alcoholic phase was added slowly to a diethyl ether solution. The precipitate was filtered off to give a red powder of [34] (12.70 g).

Standard analytical characterization was in agreement with the structure.

Step 2: Synthesis of the Compound [35]

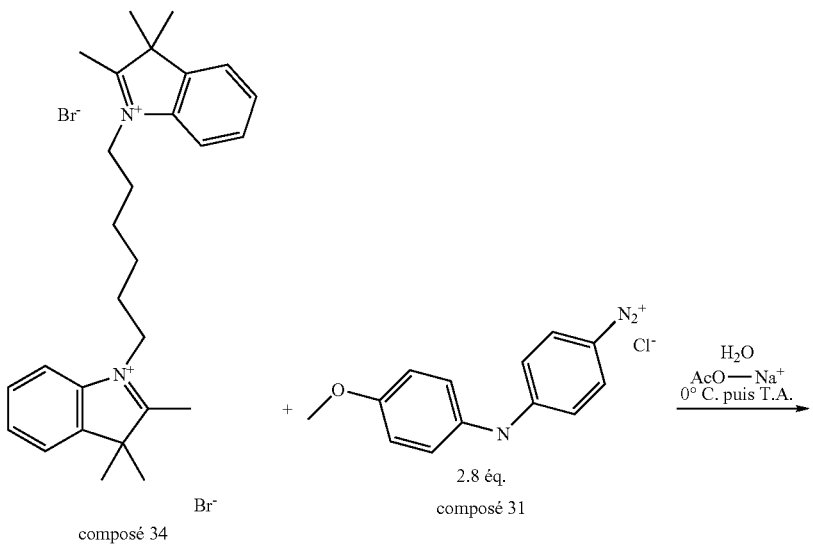

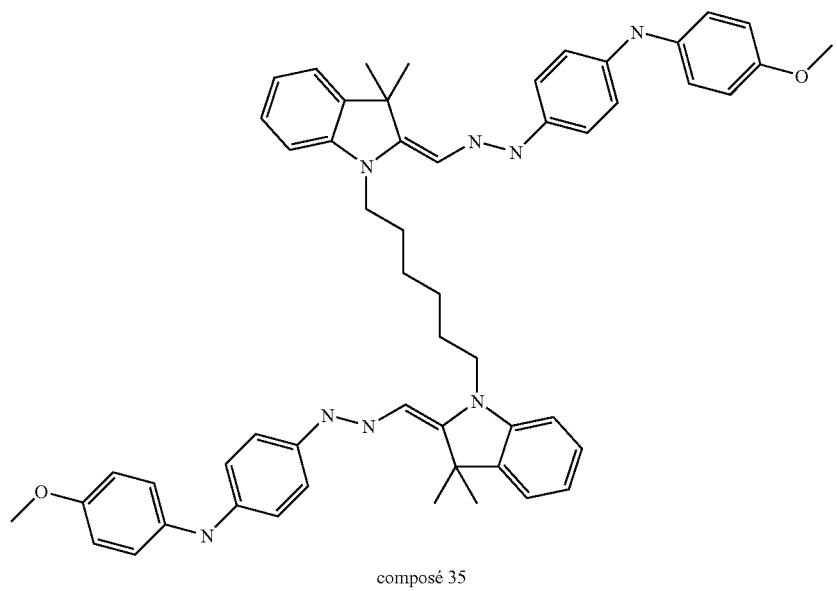

In a three neck flask fitted with a mechanical stirrer, [34] (2.15 g; 3.82 mmoles) was dissolved in water (45 ml). The reaction mixture was cooled at 0° C. Compound [31] (2.8 g, 10.69 mmoles) was slowly added to the reaction mixture adjusting the pH to 5.7 by dropwise addition of sodium acetate; the reaction mixture was stirred at 0° C. for 4.5 hours. Then, the cooling bath was removed and pH was adjusted to 11 by dropwise addition of 40% aqueous sodium hydroxide. A precipitate formed, was filtered off, rinsed with water and dried over P$_2$O$_5$ under vacuum overnight to give a black powder of [35] (3.58 g).

Standard analytical characterization was in agreement with the structure.

Step 3: Synthesis of the Compound [36]

In a three neck flask fitted with a mechanical stirrer, [35] (0.62 g; 0.68 mmole) and methyl-p-toluene sulfonate (0.6 g) were dissolved in toluene (5 ml). The reaction mixture was heated at 100° C. for 5 hours. After reaction, the solvent was removed in vacuo. The crude solid was solubilized in ethanol (50 ml) and Amberlyst resin (IRA 400) was added (10 g) to the mixture reaction. The reaction mixture was stirred at room temperature for 0.5 hour. After filtration, the solvent was removed in vacuo and the solid rinsed with diethyl ether, and dried over P$_2$O$_5$ under vacuum overnight to give a violet powder of [36] (0.44 g).

Standard analytical characterization was in agreement with the structure.

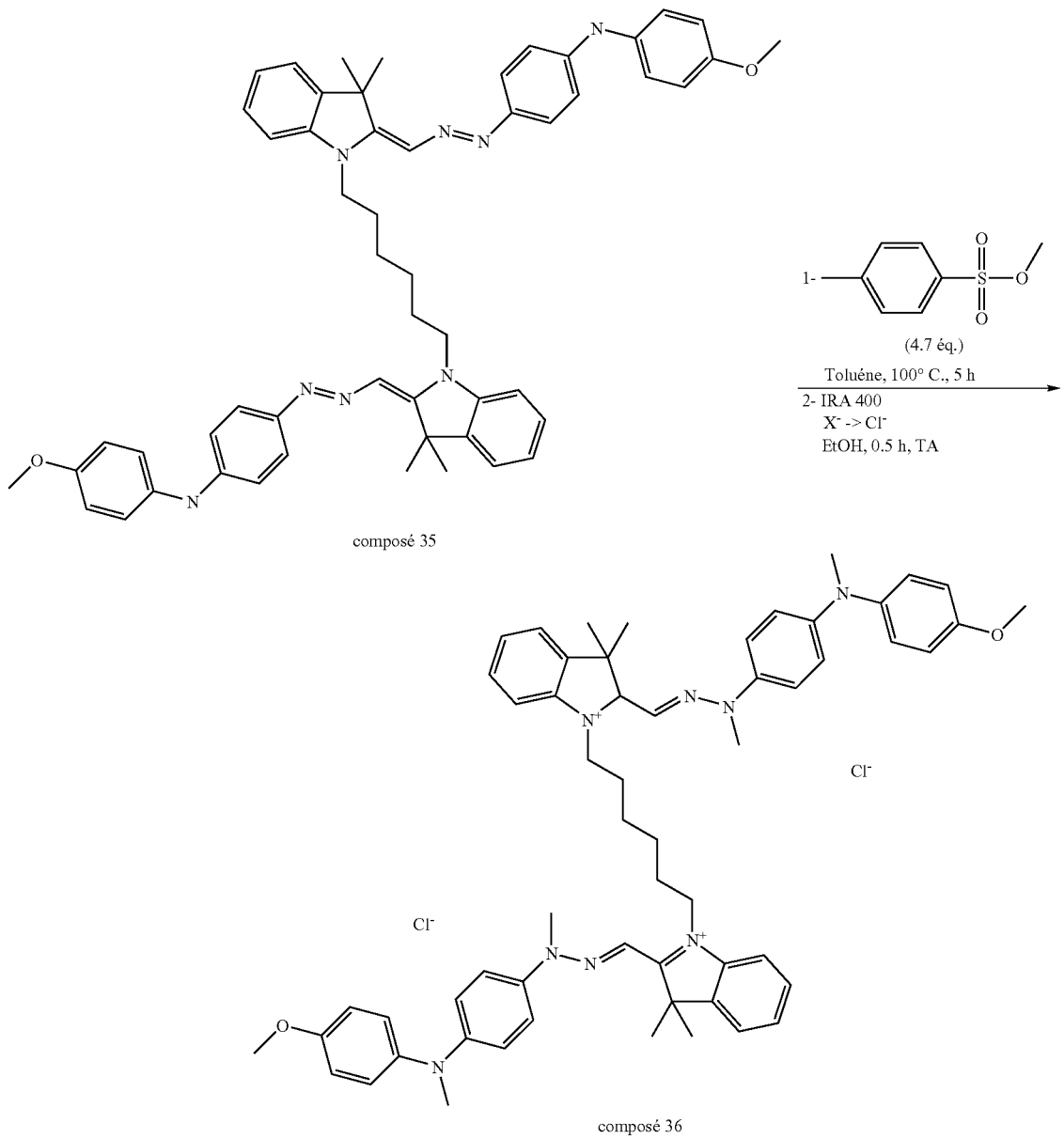

Examples of Dyeing

Dye compositions were prepared in the following proportions:

| Solution 1 | |
|---|---|
| (50/50 C8/C10) alkyl polyglucoside (2) as an aqueous 60% solution | 120 g |
| Pure absolute ethanol | 200 g |
| Polyethylene glycol (8 OE) 400 | 60 g |
| Pure benzyl alcohol | 40 g |
| Demineralized water | qs 1000 g |
| Solution 2: pH 9.5 buffer | |
| Ammonium chloride (NH4Cl) | 54 g |
| Aqueous 20% ammonia solution | qs pH = 9.5 (about 40 ml) |
| Demineralized water | qs 1000 ml |
| Solution 3: pH 7 buffer | |
| $KH_2PO_4$ | 0.026 mol/l |
| $Na_2PO_4$ | 0.041 mol/l |
| Demineralized water | qs 500 ml |

The dye compositions were obtained by dissolving the dye indicated below ($5\times10^{-3}$ mol/l) in solution 1, followed by addition of one equivalent volume of buffer solution 2 or 3 (pH 7 or 9.5).

Each composition was applied to grey hair containing 90% of white hairs (1 g of lock per 6 g of solution). After a leave-in time of 30 minutes, the locks were rinsed, washed with a standard shampoo, rinsed again and then dried.

The following dyeing results were obtained:

| | After dyeing | |
|---|---|---|
| | pH 7 | pH 9.5 |
| | Chromatic yellow | Chromatic yellow |

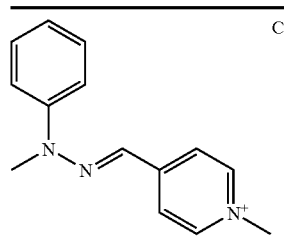

C. 1 Basic Yellow 87: compound I not in accordance with the invention

| | After dyeing | |
|---|---|---|
| | pH 7 | pH 9.5 |
| Compound 4 | Strong chromatic yellow | Strong chromatic yellow |
| Compound 6 | Strong chromatic yellow | Strong chromatic yellow |
| Compound 8 | Strong chromatic yellow | Strong chromatic yellow |
| Compound 10 | Strong chromatic yellow | Strong chromatic yellow |
| Compound 12 | Strong chromatic yellow | Strong chromatic yellow |
| Compound 25 | Chromatic orange | Chromatic orange |
| Compound 26 | Chromatic orange | Chromatic orange |
| Compound 27 | Chromatic orange | Chromatic orange |
| Compound 33 | violet | violet |
| Compound 36 | violet | violet |

The locks thus dyed were subjected to a wash-fastness test that consisted of shampooing 10 times and evaluating the color after these 10 shampoo washes. The color was evaluated by measuring L*a*b* in the L*a*b* system, using a Minolta® CM 2002 spectrophotometer (Illuminant D65). In this L*a*b* system, the three parameters denote, respectively, the intensity (L*), a* indicates the green/red color axis and b* the blue/yellow color axis.

| | After 10 shampoo washes (% loss of color) |
|---|---|
| Compound I C I Basic Yellow 87 | 20-30 |
| Compound 4 | 0-10 |
| Compound 6 | 0-10 |
| Compound 8 | 0-10 |
| Compound 10 | 0-10 |

These results show that the compounds of the invention made it possible to obtain an improved dyeing result in terms of shampoo fastness compared with the composition not in accordance with the invention containing compound 1.

Chromaticity

The following dye compositions were prepared:

| dye | $10^{-3}$ mole |
|---|---|
| Dye Support (1) | (*) |
| Deminéralized water q.s. | 100 g |

(*): Dye Support (1) pH 7

| Example | A | B |
|---|---|---|
| dye | 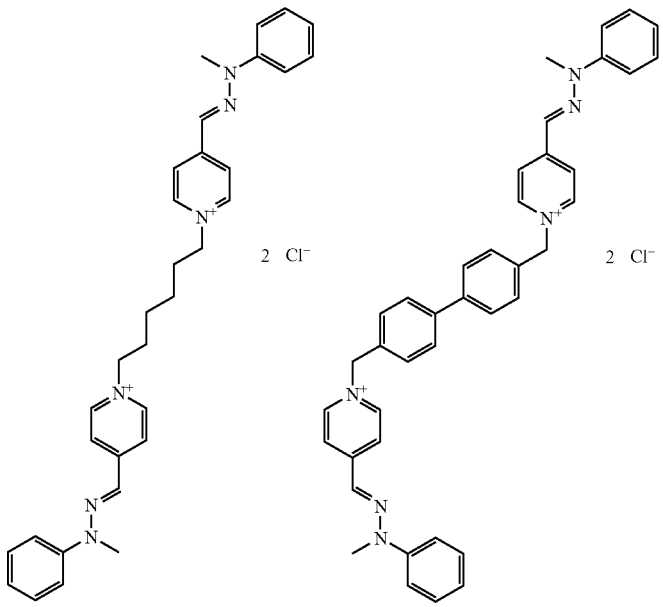 | |

Example A was in accordance with the present invention.
Example B was in accordance with WO 04/083312 (CIBA)

Dye Support (1) pH 7:

| | |
|---|---|
| 96° ethyl alcool | 20.8 g |
| Pentasodium salt of diéthylene-triamine-pentaacetic acid as an aqueous 40% solution | 0.48 g A.M. |
| C8-C10 Alkylpolyglucoside as an aqueous 60% solution | 3.6 g A.M. |
| Benzyl Alcool | 2.0 g |
| Polyethylene glycol containing 8 ethylene oxide units | 3.0 g |
| $Na_2HPO_4$ | 0.28 g |
| $KH_2PO_4$ | 0.46 g |

Each composition was applied to grey hair containing 90% of white hairs (1 g of lock per 6 g of solution). After a leave-in time of 30 minutes, the locks were rinsed, washed with a standard shampoo, rinsed again and then dried.

The following dyeing results were obtained

The color was evaluated by measuring L*a*b* in the L*a*b* system, using a Minolta® CM 2002 spectrophotometer (Illuminant D65). The lower L is, the more intensive (or darker) the color is. These tests show that a more intensive coloration was obtained with the composition according to the invention.

| Example | A | B |
|---|---|---|
| L* | 46 | 51.2 |

The following dye compositions were prepared:

| | |
|---|---|
| dye | 10-3 mole |
| Dye Support (2) | (*) |
| Demineralized water q.s. | 100 g |

(*): dye support (2) pH 9.5

| Example | C | D |
|---|---|---|
| Dye | | |

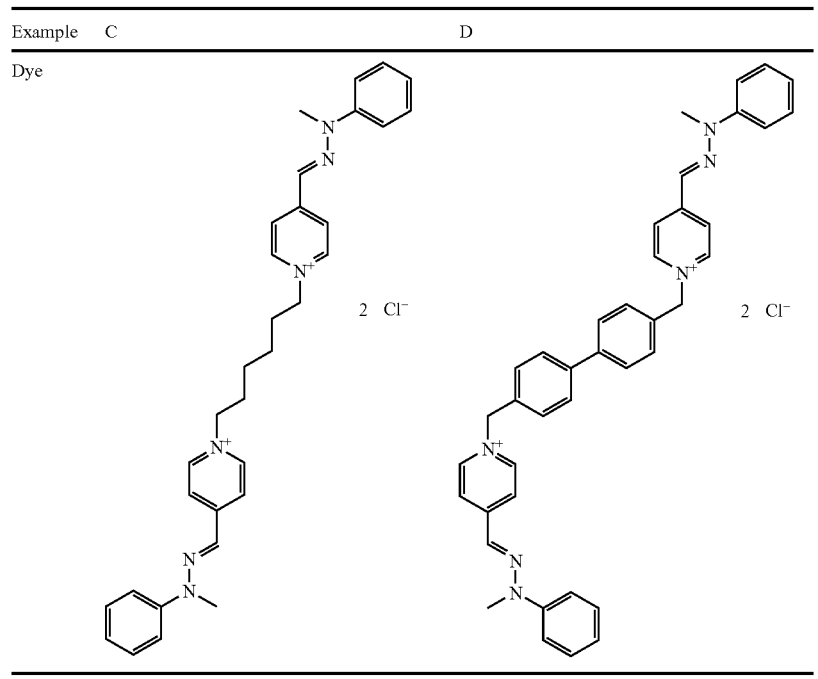

Dye Support (2) pH 9.5:

| | |
|---|---|
| 96° ethyl alcool | 20.8 g |
| Pentasodium salt of diéthylene-triamine-pentaacetic acid as an aqueous 40% solution | 0.48 g A.M. |
| C8-C10 Alkylpolyglucoside as an aqueous 60% solution | 3.6 g A.M. |
| Benzyl Alcool | 2.0 g |
| Polyethylene glycol containing 8 ethylene oxide units | 3.0 g |
| NH$_4$Cl | 4.32 g |
| Aqueous ammonia containing 20% NH$_3$ | 2.94 g |

At the time of use, each composition was mixed with an equal weight of 20 volumes aqueous hydrogen peroxide solution (6% by weight). A final pH of 9.5 was obtained.

Each mixture obtained was applied to locks of grey hair containing 90% white hair. After an action time of 30 minutes, the locks were rinsed, washed with a standard shampoo, rinsed again and then dried.

The shades obtained are given in the table below. The color was evaluated by measuring L*a*b* in the L*a*b* system, using a Minolta® CM 2002 spectrophotometer (Illuminant D65). These tests show that a more intensive coloration was obtained with the composition according to the invention.

| Example | C | D |
|---|---|---|
| L* | Chromatic yellow | yellow |
| | 48.7 | 56.5 |

What is claimed is:

1. A dicationic bis-hydrazone compound of formula (I)

DYE-L-DYE in which each of the chromophores DYE, which may be identical or different, is chosen from chromophores of formulae (Ia), (Ib), (Ic), (Id), (Ie), (If) and (Ig) below:

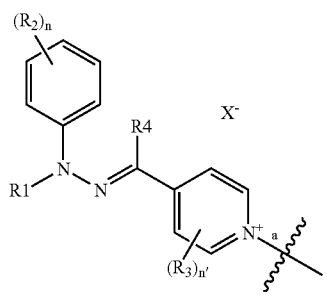

(Ia)

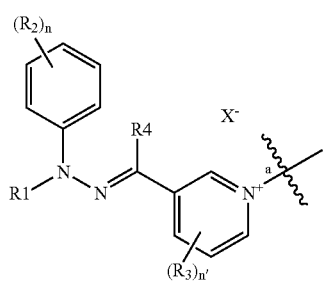

(Ib)

-continued

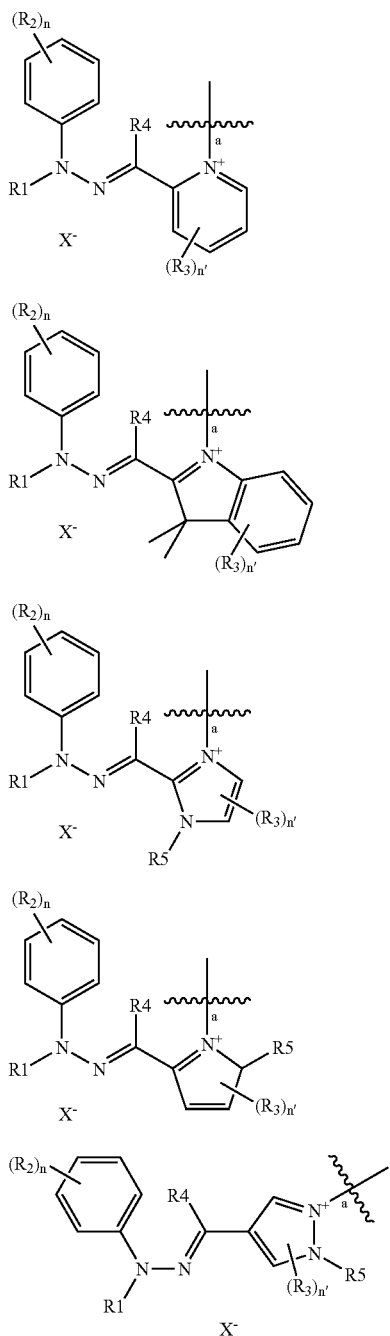

wherein:

the groups $R_1$ and $R_5$, independently of each other, are chosen from linear or branched, saturated or unsaturated $C_1$-$C_{20}$ hydrocarbon-based chains, which can form one or more optionally substituted, optionally aromatic 3- to 7-membered carbon-based rings, the chains being optionally substituted or being optionally interrupted with at least one hetero atom or with at least one group bearing a hetero atom, the groups $R_2$ and $R_3$, independently of each other, are chosen from:

a halogen atom chosen from bromine, chlorine and fluorine;

linear or branched, saturated or unsaturated $C_1$-$C_{16}$ hydrocarbon-based chains, which can form one or more optionally aromatic 3- to 6-membered carbon-based rings, the chain being optionally substituted or being optionally interrupted with at least one hetero atom or with at least one group bearing at least one hetero atom;

a hydroxyl group;

a $C_1$-$C_4$ alkoxy group; a $C_2$-$C_4$ (poly)hydroxyalkoxy group; an alkoxycarbonyl group (RO—CO—) in which R is a $C_1$-$C_4$ alkyl radical; or an alkylcarbonyloxy radical (RCO—O—) in which R is a $C_1$-$C_4$ alkyl radical; an optionally substituted aryloxy group;

an amino group, an amino group substituted with at least one $C_1$-$C_4$ alkyl radical, which may be identical or different, optionally bearing at least one hydroxyl group, the two alkyl radicals possibly forming, with the nitrogen atom to which they are attached, a saturated or unsaturated, optionally substituted 5- or 6-membered heterocycle, optionally bearing another nitrogen or non-nitrogen hetero atom; an alkylcarbonylamino group (RCO—NR—) in which the radicals R, independently of each other, are chosen from $C_1$-$C_4$ alkyl radicals; a carbamoyl group ((R)$_2$N—CO—) in which the radicals R, independently of each other, are chosen from a hydrogen atom and a $C_1$-$C_4$ alkyl radical; a ureido group (N(R)$_2$—CO—NR'—) in which the radicals R and R', independently of each other, are chosen from a hydrogen atom and a $C_1$-$C_4$ alkyl radical; a sulfonamide group ((R)$_2$N—SO$_2$—) in which the radicals R, independently of each other, are chosen from a hydrogen atom and a $C_1$-$C_4$ alkyl radical; an alkylthio group (R—S—) in which the group R is a $C_1$-$C_4$ alkyl radical; an alkylsulfonylamino group (RSO$_2$—NR'—) in which the radicals R and R', independently of each other, are chosen from a hydrogen atom and a $C_1$-$C_4$ alkyl radical;

a nitro group; a cyano group; a halogen atom;

a trifluoromethyl group (CF$_3$);

$R_1$ and $R_2$ may also form, with the nitrogen atom substituted with $R_1$, a saturated or unsaturated, substituted or unsubstituted 5- or 6-membered heterocycle;

two adjacent radicals $R_2$ may form, together with the carbon atoms to which they are attached, a saturated or unsaturated, substituted or unsubstituted 5- or 6-membered aromatic ring or heterocycle;

two adjacent radicals $R_3$ can together form a saturated or unsaturated, substituted or unsubstituted 5- or 6-membered aromatic ring or heterocycle;

the groups $R_4$, independently of each other, are chosen from:

a hydrogen atom;

linear or branched, saturated or unsaturated $C_1$-$C_{16}$ hydrocarbon-based chains, which can form at least one optionally aromatic 3- to 6-membered carbon-based ring, the chains being optionally substituted, optionally interrupted with at least one hetero atom or with at least one group bearing at least one hetero atom;

an amino group, an amino group substituted with at least one $C_1$-$C_4$ alkyl radical, which may be identical or different, optionally bearing at least one hydroxyl group, the two alkyl radicals possibly forming, with the nitrogen atom to which they are attached, a saturated or unsaturated, optionally substituted 5- or 6-membered heterocycle, optionally bearing another nitrogen or non-nitrogen hetero atom; an alkylcarbonylamino group (RCO—NR—) in which the radicals R, independently of each other, are chosen from $C_1$-$C_4$ alkyl radicals; a ureido group (N(R)$_2$—CO—NR'—) in which the radicals R and R', independently of each other, are chosen from a hydrogen atom and a $C_1$-$C_4$ alkyl radical; an alkylsulfonylamino group (RSO$_2$—NR'—) in which the radicals R and R', independently of each other, are chosen from a hydrogen atom and a $C_1$-$C_4$ alkyl radical;

n is an integer from 0 to 5, n' is an integer from 0 to 4, the bond a in formulae (Ia), (Ib), (Ic), (Id), (Ie), (If) and (Ig) links each of the chromophores DYE to the linker L of formula (I), X is an organic or mineral anion or mixture of anions for equilibrating the charge(s) of the compound Ia or Ib;

the group L is a linear or branched $C_1$-$C_{60}$ hydrocarbon-based chain that can form at least one optionally aromatic, optionally substituted 3- to 7-membered carbon-based ring, the chain being optionally substituted, optionally interrupted with at least one hetero atom or with at least one group bearing a hetero atom, L not comprising any peroxide, nitro, diazo or nitroso groups, the linker L being linked to the quaternized nitrogen atom of each of the chromophores DYE via a carbon atom, L not being cationic;

with the proviso that when the two chromophores DYE are identical and correspond to formula (Ia) with n=n'=0, then the group L is not one of the following groups:

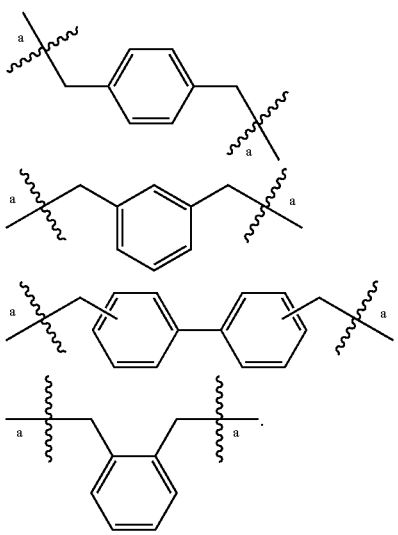

2. A dicationic bis-hydrazone compound according to claim 1, wherein in formula (I), L is chosen from alkylene radicals ($C_nH_{2n}$) comprising from 1 to 60 carbon atoms, optionally substituted and/or interrupted with at least one hetero atom.

3. A dicationic bis-hydrazone compound according to claim 2, wherein L is chosen from alkylene radicals ($C_nH_{2n}$) comprising from 2 to 20 carbon atoms, optionally substituted and/or interrupted with at least one hetero atom.

4. A dicationic bis-hydrazone compound according to claim 1, wherein L is $C_1$-$C_{20}$ alkyl-(hetero)aryl-$C_1$-$C_{20}$ alkyl.

5. A dicationic bis-hydrazone compound according to claim 4, wherein L is $C_1$-$C_{10}$ alkyl-(hetero)aryl-$C_1$-$C_{10}$ alkyl.

6. A dicationic bis-hydrazone compound according claim 1, wherein the groups $R_1$ are identical and are chosen from $C_1$-$C_4$ alkyl radicals optionally substituted with at least one radical chosen from hydroxyl, $C_1$-$C_2$ alkoxy, amino and $C_1$-$C_2$ (di)alkylamino radicals; an alkylcarbonyl radical (R—CO—) in which the radical R is a $C_1$-$C_4$ alkyl radical; a carbamoyl group ((R)$_2$N—CO—) in which the radicals R, independently of each other, are chosen from a hydrogen atom and a $C_1$-$C_4$ alkyl radical; an alkylsulfonyl radical (R—SO$_2$—) in which the radical R is a $C_1$-$C_4$ alkyl radical.

7. A dicationic bis-hydrazone compound according to claim 6, wherein the groups $R_1$ are identical and are chosen from methyl, ethyl, 2-hydroxyethyl, 2-methoxyethyl, acetyl ($CH_3CO$—) and methylsulfonyl ($CH_3SO_2$—) radicals.

8. A dicationic bis-hydrazone compound according to claim 1, wherein the groups $R_1$ and $R_2$ form, with the nitrogen atom substituted with $R_1$, a saturated or unsaturated 5- or 6-membered heterocycle substituted with at least one alkyl radical.

9. A dicationic bis-hydrazone compound according to claim 1, wherein the groups $R_2$ and $R_3$ are chosen from, independently of each other:

a hydrogen atom;

a halogen atom;

linear or branched $C_1$-$C_4$ alkyl radicals optionally substituted with at least one radical chosen from hydroxyl, $C_1$-$C_2$ alkoxy, $C_2$-$C_4$ (poly)hydroxyalkoxy, amino, $C_1$-$C_2$ (di)alkylamino, thio (—SH), ($C_1$-$C_4$)alkylsulfinyl, ($C_1$-$C_4$)alkylsulfonyle and ($C_1$-$C_4$)thioalkyl radicals;

phenyl radicals optionally substituted with at least one radical chosen from hydroxyl, $C_1$-$C_2$ alkoxy, $C_2$-$C_4$ (poly)hydroxyalkoxy, amino and $C_1$-$C_2$(di)alkylamino radicals, or a halogen atom chosen from chlorine, fluorine and bromine;

$C_1$-$C_4$ alkoxy radicals;

($C_1$-$C_4$)alkylsulfonylamino radicals;

$C_2$-$C_4$ (poly)hydroxyalkoxy radicals;

amino radicals;

$C_1$-$C_2$ (di)alkylamino radicals;

$C_2$-$C_4$ (poly)hydroxyalkylamino radicals;

alkylcarbonyl radicals (R—CO—) in which the radical R is a $C_1$-$C_4$ alkyl radical;

carbamoyl radicals ((R)$_2$N—CO—) in which the radicals R, independently of each other, are chosen from a hydrogen atom and a $C_1$-$C_4$ alkyl radical;

alkylsulfonylamino radicals (RSO$_2$N—) in which the radical R is a $C_1$-$C_4$ alkyl radical;

aminosulfonyl radicals ((R)$_2$NSO$_2$—) in which the radicals R, independently of each other, are chosen from a hydrogen atom and a $C_1$-$C_4$ alkyl radical;

alkylthio radicals (RS—) in which the radical R is a $C_1$-$C_4$ alkyl radical;

thio radicals (HS—)

alkylsulfinyl radicals (RSO—) in which the radical R is a $C_1$-$C_4$ alkyl radical;

alkylsulfonyl radicals (R—SO$_2$—) in which the radical R is a $C_1$-$C_4$ alkyl radical;

alkylcarbonylamino radicals (RCONR'—) in which the radical R is chosen from a hydrogen atom and a $C_1$-$C_4$ alkyl radical and the radical R' is chosen from a hydrogen atom and a $C_1$-$C_4$ alkyl radical.

10. A dicationic bis-hydrazone compound according to claim 9, wherein the groups $R_2$ and $R_3$ are chosen from, independently of each other, a hydrogen atom and methyl, ethyl, 2-hydroxyethyl, 2-methoxyethyl, acetyl (CH₃CO—), methylsulfonyl (CH₃SO₂—), amide (CH₃CONH—), hydroxyl, amino, methylamino, dimethylamino, 2-hydroxyethylamino, methoxy, ethoxy and phenyl radicals.

11. A dicationic bis-hydrazone compound according to claim 1, wherein the groups $R_5$ are identical and are chosen from $C_1$-$C_4$ alkyl radicals optionally substituted with at least one radical chosen from hydroxyl, $C_1$-$C_2$ alkoxy, amino and $C_1$-$C_2$ (di)alkylamino radicals; and an optionally substituted phenyl radical.

12. A dicationic bis-hydrazone compound according to claim 11, wherein the groups $R_5$ are identical and are chosen from methyl, ethyl, 2-hydroxyethyl, 2-methoxyethyl and phenyl radicals.

13. A dicationic bis-hydrazone compound according to claim 1, wherein said compound is chosen from the compounds of formulae:

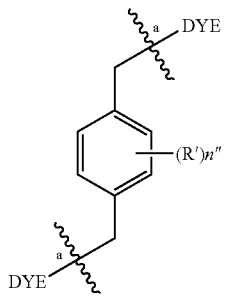

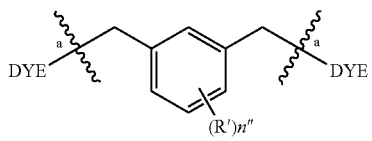

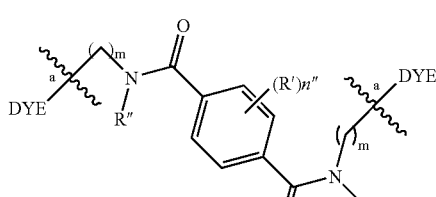

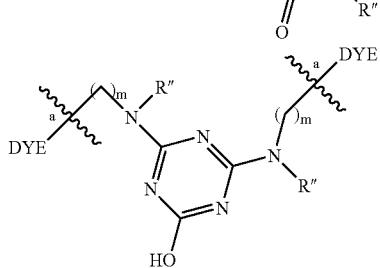

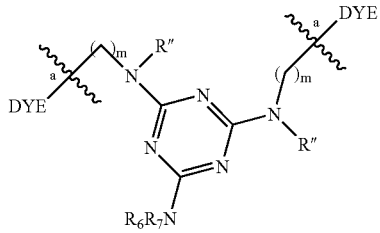

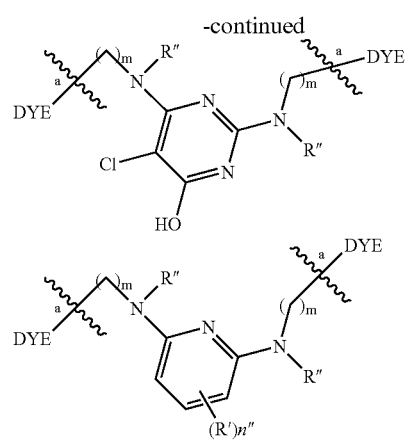

in which:
- R', which may be identical or different, have the same definition as $R_2$ of claim 1,
- R", which may be identical or different, are chosen from a hydrogen atom and a $C_1$-$C_4$ alkyl radical,
- m is an integer from 2 to 6,
- n" is an integer from 0 to 4.

14. A dicationic bis-hydrazone compound according to claim 1, wherein said compound is chosen from the compounds of formulae:

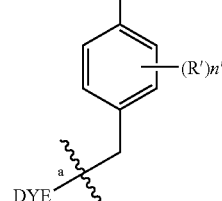

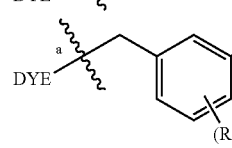

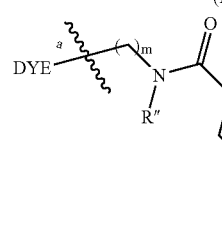

in which:
- R', which may be identical or different, have the same definition as $R_2$ of claim 1,
- R", which may be identical or different, are chosen from a hydrogen atom and a $C_1$-$C_4$ alkyl radical,
- m is an integer from 2 to 6,
- n" is an integer from 0 to 4.

15. A dicationic bis-hydrazone compound according to claim 1, wherein said compound is chosen from the compounds of formulae:
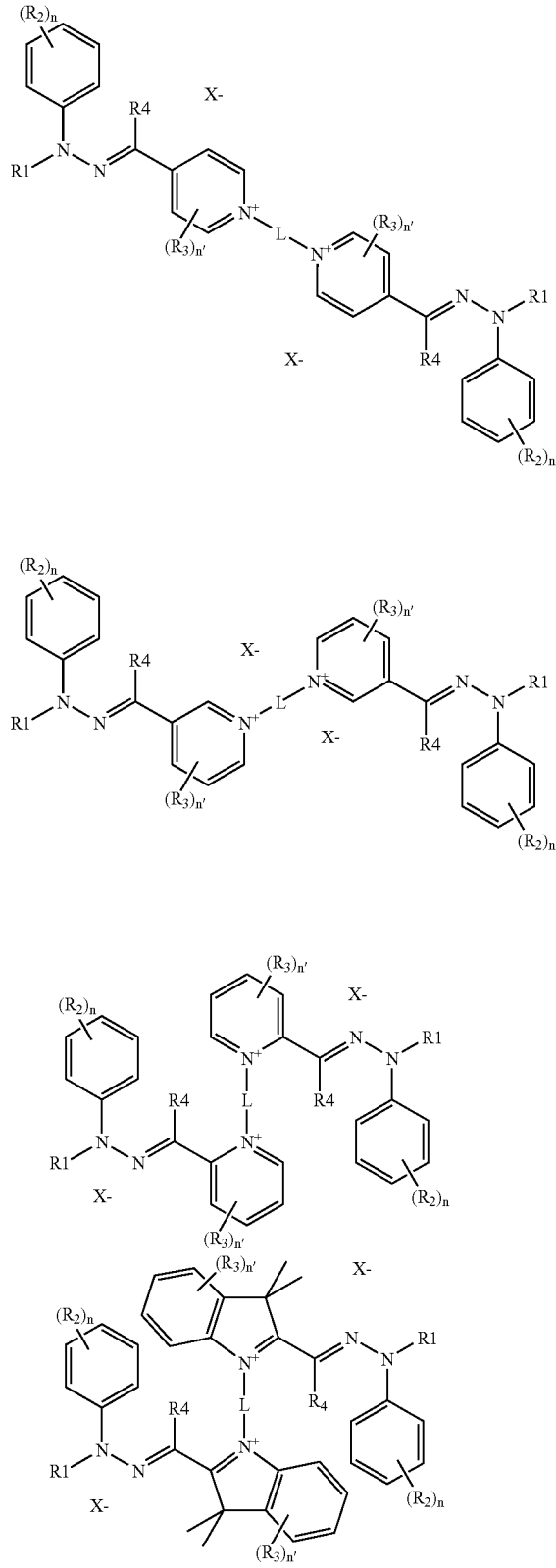
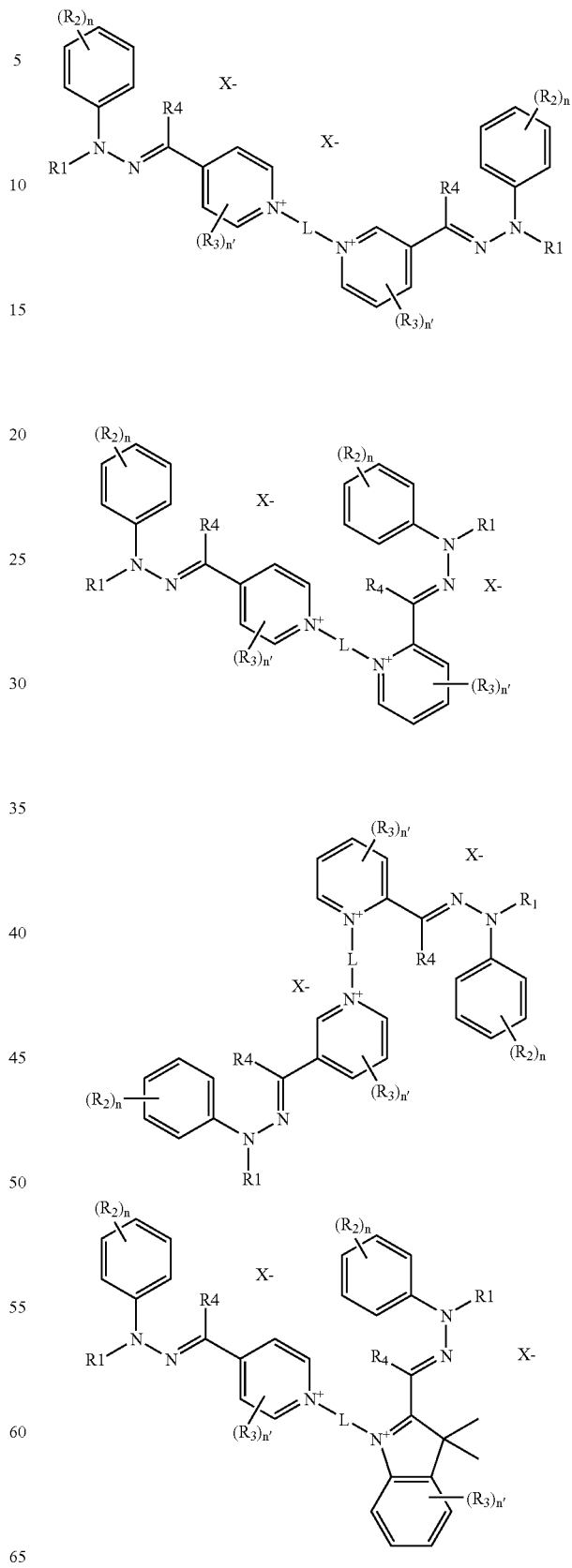

-continued
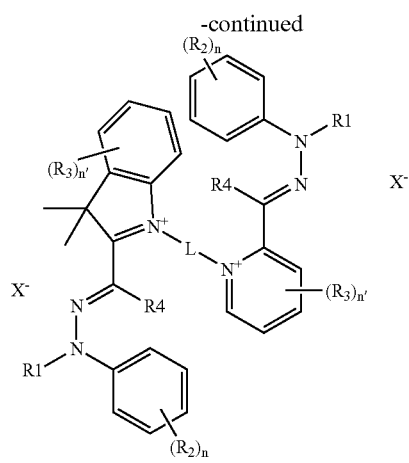
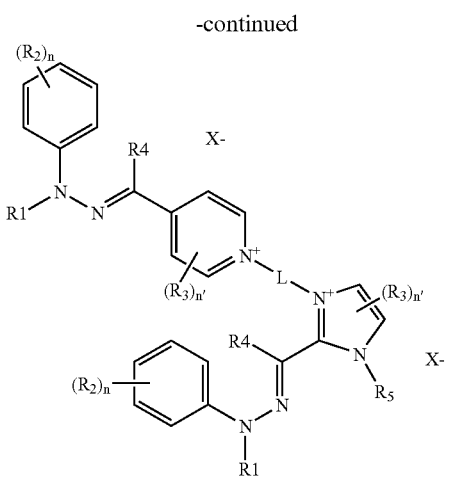
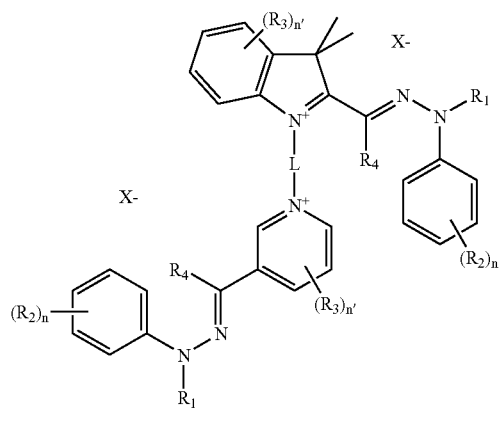
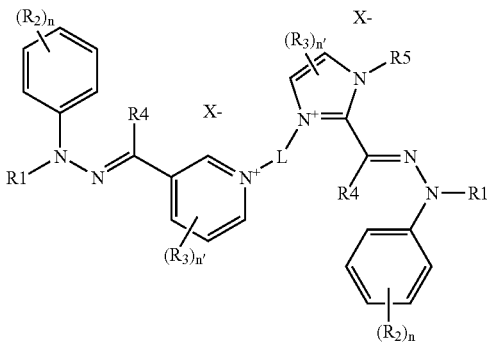
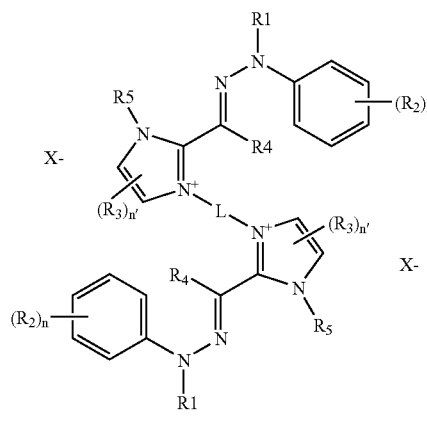
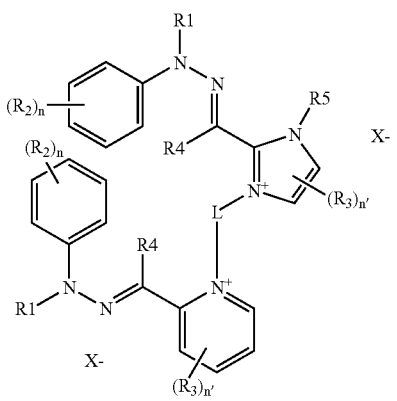

-continued
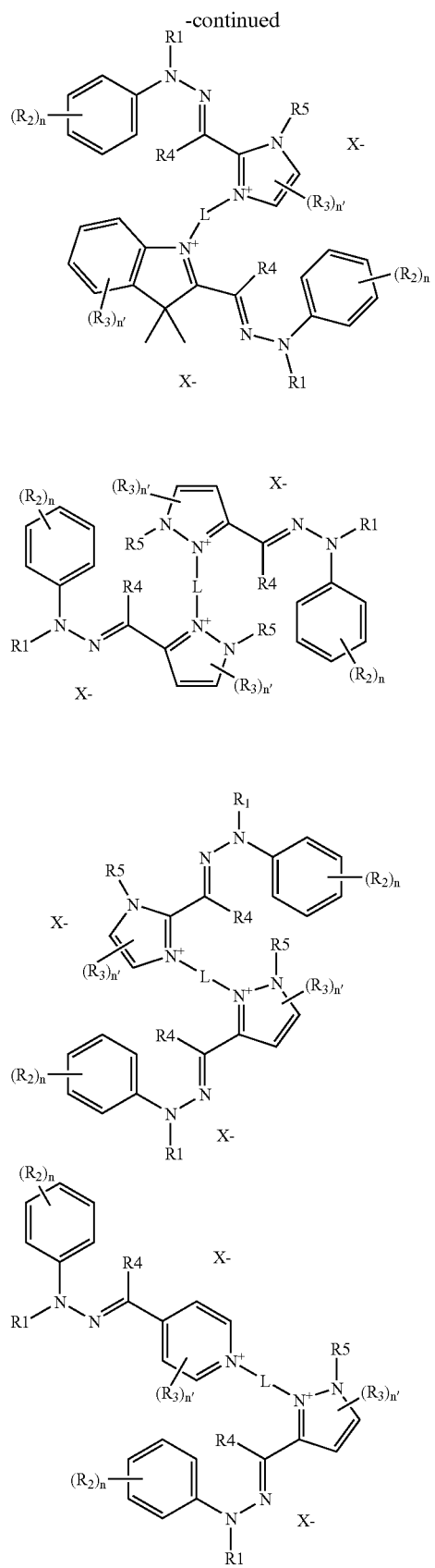
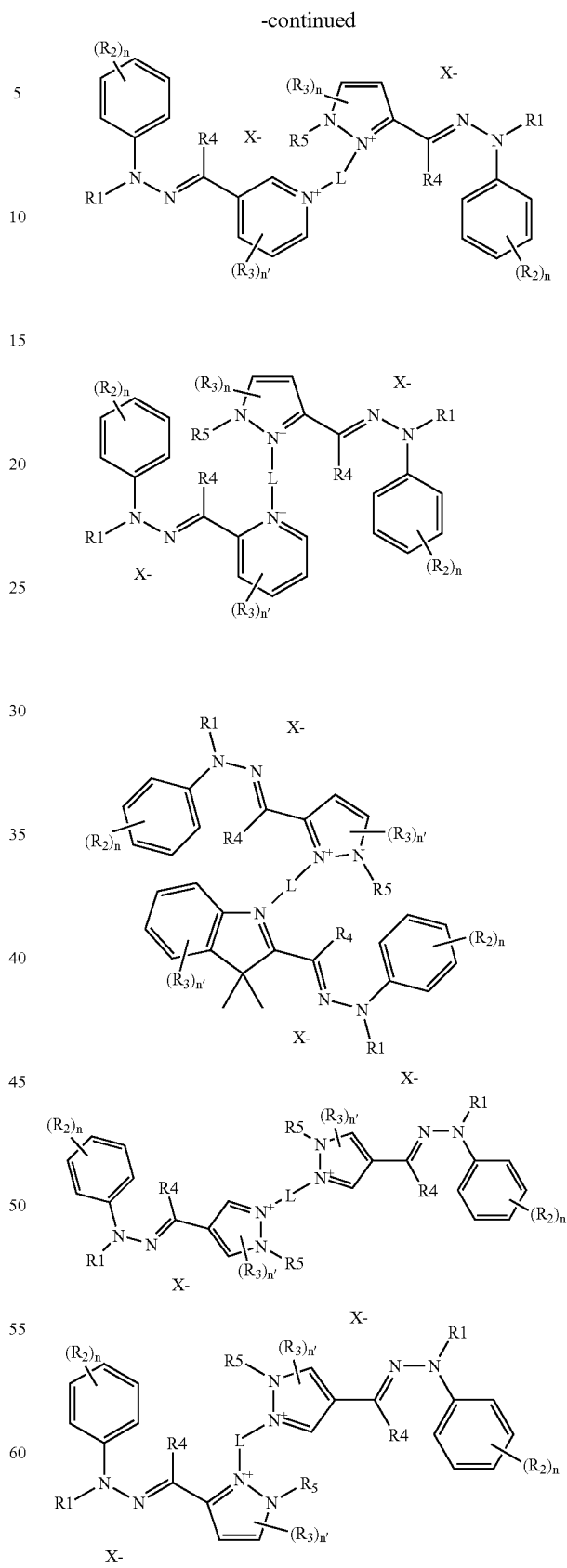

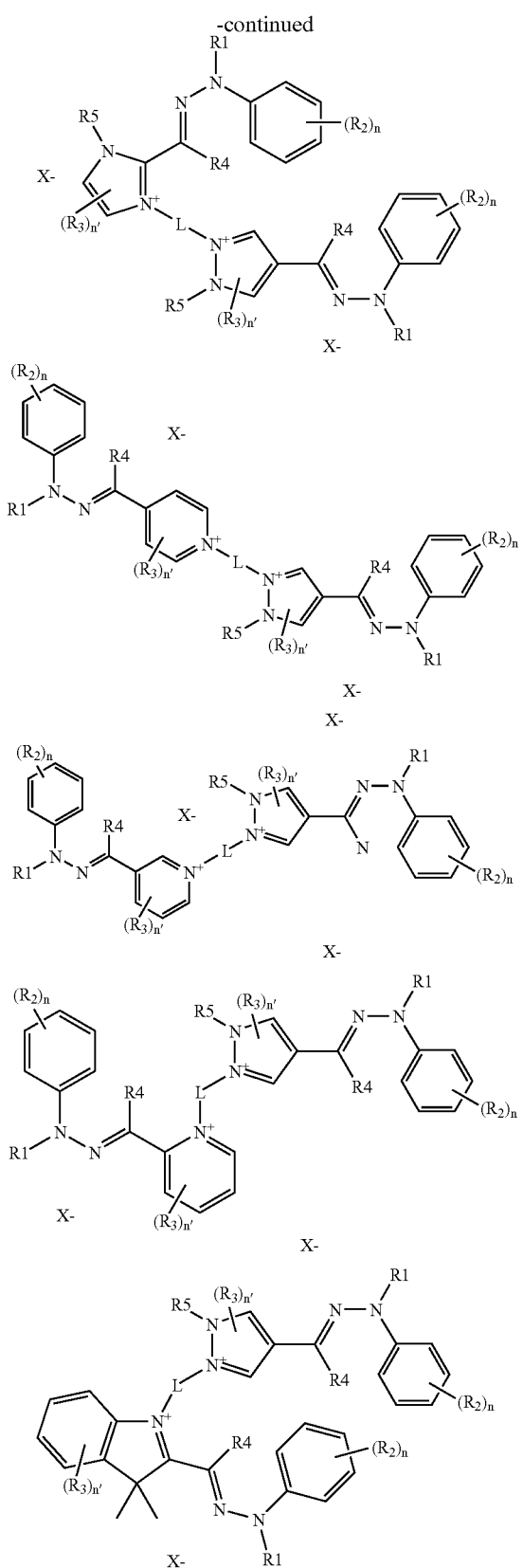

in which the radicals R₁, R₂, R₃, R₄, R₅, X, n, n' and L are as defined in claim 1.

16. A dicationic bis-hydrazone compound according to claim 1, wherein the compound is chosen from the following compounds:

4-{(E)-[methyl(phenyl)hydrazono]methyl}-1-[3-(4-{(E)-[methyl(phenyl)hydrazono]methyl}pyridinium-1-yl)propyl]pyridinium dibromide, 4-{(E)-[methyl(phenyl)hydrazono]methyl}-1-[4-(4-((E)-[methyl(phenyl)hydrazono]methyl}pyridinium-1-yl)butyl]pyridinium dibromide 4-{(E)-[methyl(phenyl)hydrazono]methyl}-1-[5-(4-{(E)-[methyl(phenyl)hydrazono]methyl}pyridinium-1-yl)pentyl]pyridinium dibromide 4-{(E)-[methyl(phenyl)hydrazono]methyl}-1-[6-(4-{(E)-[methyl(phenyl)hydrazono]methyl}pyridinium-1-yl)hexyl]pyridinium dibromide 4-{(E)-[methyl(phenyl)hydrazono]methyl}-1-(6-{[4-({[6-(4-{(E)-[methyl(phenyl)hydrazono]methyl}pyridinium-1-yl)hexyl]amino}carbonyl)benzoyl]amino}hexyl)pyridinium dibromide 4-{(E)-[methyl(phenyl)hydrazono]methyl}-1-[6-(4-{(E)-[methyl(phenyl)hydrazono]methyl}quinolinium-1-yl)hexyl]quinolinium dibromide 4-{(E)-[methyl(phenyl)hydrazono]methyl}-1-[6-(4-{(E)-[methyl(phenyl)hydrazono]methyl}pyridinium-1-yl)hexyl]quinolinium dibromide 1-methyl-3-[5-(1-methyl-2-{(E)-[methyl(phenyl)hydrazono]methyl}-1H-imidazol-3-ium-3-yl)pentyl]-2-{(E)-[methyl(phenyl)hydrazono]methyl}-1H-imidazol-3-ium dibromide 1-methyl-3-[4-(1-methyl-2-{(E)-[methyl(phenyl)hydrazono]methyl}-1H-benzimidazol-3-ium-3-yl)butyl]-2-{(E)-[methyl(phenyl)hydrazono]methyl}-1H-benzimidazol-3-ium dibromide 1-[6-(1-methyl-2-{(E)-[methyl(phenyl)hydrazono]methyl}-1H-imidazol-3-ium-3-yl)hexyl]-4-{(E)-[methyl(phenyl)hydrazono]methyl}quinolinium dibromide 1-[6-(1-methyl-2-{(E)-[methyl(phenyl)hydrazono]methyl}-1H-benzimidazol-3-ium-3-yl)hexyl]-4-{(E)-[methyl(phenyl)hydrazono]methyl}quinolinium dibromide, 1,1'-pentane-1,5-diylbis(4-{(E)-[methyl(phenyl)hydrazono]methyl}quinolinium) dibromide, 1,1'-butane-1,4-diylbis(4-{(E)[methyl(phenyl)hydrazono]methyl}quinolinium) dibromide, 1,1'-propane-1,3-diylbis(4-{(E)-[methyl(phenyl)hydrazono]methyl}quinolinium) dibromide, 2-{(E)-[{4-[(4-methoxyphenyl)(methyl)amino]phenyl}(methyl)hydrazono]methyl}-3,3-dimethyl-1-[6-(4{(E)-[methyl(phenyl)hydrazono]methyl}pyridinium-1-yl)hexyl]-3H-indolium dichloride, 1,1'-hexane-1,6-diylbis(2-{(E)-[{4-[(4-methoxyphenyl)(methyl)amino]phenyl}(methyl)hydrazono]methyl}-3,3-dimethyl-3H-indolium) dichloride.

17. A dye composition for dyeing keratin fibers, comprising, in a suitable dyeing medium, at least one dicationic bis-hydrazone compound of formula (I)

DYE-L-DYE in which each of the chromophores DYE, which may be identical or different, is chosen from chromophores of formulae (Ia), (Ib), (Ic), (Id), (Ie), (If) and (Ig) below:

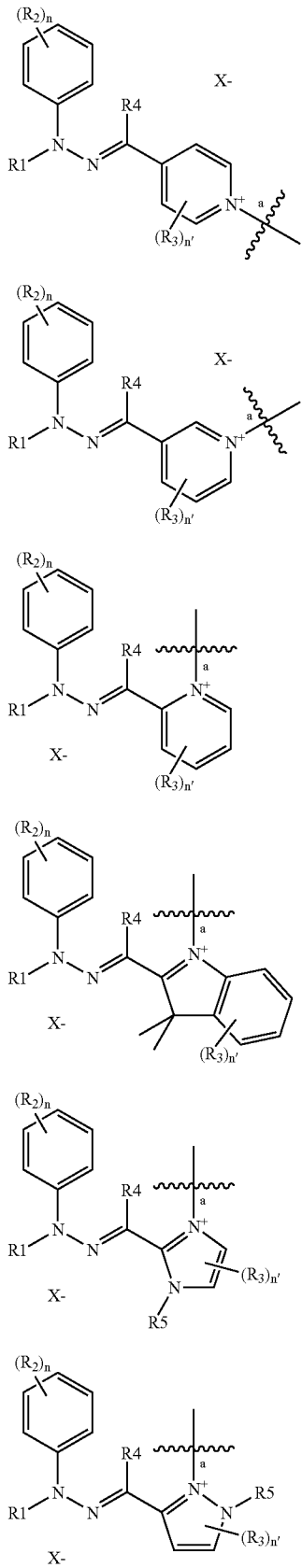
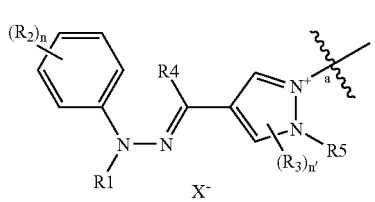

wherein:
the groups $R_1$ and $R_5$, independently of each other, are chosen from linear or branched, saturated or unsaturated $C_1$-$C_{20}$ hydrocarbon-based chains, which can form one or more optionally substituted, optionally aromatic 3- to 7-membered carbon-based rings, the chains being optionally substituted or being optionally interrupted with at least one hetero atom or with at least one group bearing a hetero atom, the groups $R_2$ and $R_3$, independently of each other, are chosen from:

a halogen atom chosen from bromine, chlorine and fluorine;

linear or branched, saturated or unsaturated $C_1$-$C_{16}$ hydrocarbon-based chains, which can form one or more optionally aromatic 3- to 6-membered carbon-based rings, the chain being optionally substituted or being optionally interrupted with at least one hetero atom or with at least one group bearing at least one hetero atom;

a hydroxyl group;

a $C_1$-$C_4$ alkoxy group; a $C_2$-$C_4$ (poly)hydroxyalkoxy group; an alkoxycarbonyl group (RO—CO—) in which R is a $C_1$-$C_4$ alkyl radical; or an alkylcarbonyloxy radical (RCO—O—) in which R is a $C_1$-$C_4$ alkyl radical; an optionally substituted aryloxy group;

an amino group, an amino group substituted with at least one $C_1$-$C_4$ alkyl radical, which may be identical or different, optionally bearing at least one hydroxyl group, the two alkyl radicals possibly forming, with the nitrogen atom to which they are attached, a saturated or unsaturated, optionally substituted 5- or 6-membered heterocycle, optionally bearing another nitrogen or non-nitrogen hetero atom; an alkylcarbonylamino group (RCO—NR—) in which the radicals R, independently of each other, are chosen from $C_1$-$C_4$ alkyl radicals; a carbamoyl group ((R)$_2$N—CO—) in which the radicals R, independently of each other, are chosen from a hydrogen atom and a $C_1$-$C_4$ alkyl radical; a ureido group (N(R)$_2$—CO—NR'—) in which the radicals R and R', independently of each other, are chosen from a hydrogen atom and a $C_1$-$C_4$ alkyl radical; a sulfonamide group ((R)$_2$N—SO$_2$—) in which the radicals R, independently of each other, are chosen from a hydrogen atom and a $C_1$-$C_4$ alkyl radical; an alkylthio group (R—S—) in which the group R is a $C_1$-$C_4$ alkyl radical; an alkylsulfonylamino group (RSO$_2$—NR'—) in which the radicals R and R', independently of each other, are chosen from a hydrogen atom and a $C_1$-$C_4$ alkyl radical;

a nitro group; a cyano group; a halogen atom;

a trifluoromethyl group (CF$_3$);

$R_1$ and $R_2$ may also form, with the nitrogen atom substituted with $R_1$, a saturated or unsaturated, substituted or unsubstituted 5- or 6-membered heterocycle;

two adjacent radicals $R_2$ may form, together with the carbon atoms to which they are attached, a saturated or unsaturated, substituted or unsubstituted 5- or 6-membered aromatic ring or heterocycle;

two adjacent radicals $R_3$ can together form a saturated or unsaturated, substituted or unsubstituted 5- or 6-membered aromatic ring or heterocycle;

the groups $R_4$, independently of each other, are chosen from:

a hydrogen atom;

linear or branched, saturated or unsaturated $C_1$-$C_{16}$ hydrocarbon-based chains, which can form at least one optionally aromatic 3- to 6-membered carbon-based ring, the chains being optionally substituted, optionally interrupted with at least one hetero atom or with at least one group bearing at least one hetero atom;

an amino group, an amino group substituted with at least one $C_1$-$C_4$ alkyl radical, which may be identical or different, optionally bearing at least one hydroxyl group, the two alkyl radicals possibly forming, with the nitrogen atom to which they are attached, a saturated or unsaturated, optionally substituted 5- or 6-membered heterocycle, optionally bearing another nitrogen or non-nitrogen hetero atom; an alkylcarbonylamino group (RCO—NR—) in which the radicals R, independently of each other, are chosen from $C_1$-$C_4$ alkyl radicals; a ureido group (N(R)$_2$—CO—NR'—) in which the radicals R and R', independently of each other, are chosen from a hydrogen atom and a $C_1$-$C_4$ alkyl radical; an alkylsulfonylamino group (RSO$_2$—NR'—) in which the radicals R and R', independently of each other, are chosen from a hydrogen atom and a $C_1$-$C_4$ alkyl radical;

n is an integer from 0 to 5, n' is an integer from 0 to 4, the bond a in formulae (Ia), (Ib), (Ic), (Id), (Ie), (If) and (Ig) links each of the chromophores DYE to the linker L of formula (I), X is an organic or mineral anion or mixture of anions for equilibrating the charge(s) of the compound Ia or Ib;

the group L is a linear or branched $C_1$-$C_{60}$ hydrocarbon-based chain that can form at least one optionally aromatic, optionally substituted 3- to 7-membered carbon-based ring, the chain being optionally substituted, optionally interrupted with at least one hetero atom or with at least one group bearing a hetero atom, L not comprising any peroxide, nitro, diazo or nitroso groups, the linker L being linked to the quaternized nitrogen atom of each of the chromophores DYE via a carbon atom, L not being cationic;

with the proviso that when the two chromophores DYE are identical and correspond to formula (Ia) with n=n'=0, then the group L is not one of the following groups:

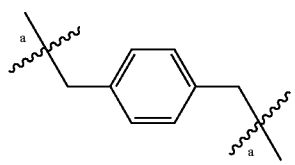

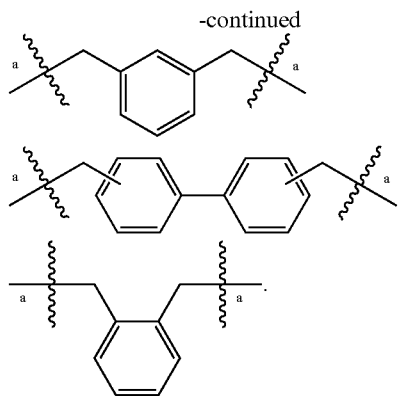

18. A dye composition according to claim 17, wherein said at least one dicationic bis-hydrazone compound is present in an amount ranging from 0.001 to 10% by weight relative to the total weight of the composition.

19. A dye composition according to claim 18, wherein said at least one dicationic bis-hydrazone compound is present in an amount ranging from 0.01 to 10% by weight relative to the total weight of the composition.

20. A dye composition according to claim 17, further comprising at least one additional direct dye.

21. A dye composition according to claim 17, further comprising at least one oxidation dye precursor chosen from oxidation bases and couplers.

22. A dye composition according to claim 21, wherein said at least one oxidation base is chosen from para-phenylenediamines, bis(phenyl)alkylenediamines, para-aminophenols, ortho-aminophenols and heterocyclic bases, and the addition salts thereof.

23. A dye composition according to claim 21, wherein the at least one oxidation base is present in an amount ranging from 0.001% to 20% by weight relative to the total weight of the composition.

24. A dye composition according to claim 23, wherein the at least one oxidation base is present in an amount ranging from 0.005% to 6% by weight relative to the total weight of the composition.

25. A dye composition according to claim 21, further comprising at least one coupler chosen from meta-phenylenediamines, meta-aminophenols, meta-diphenols, naphthalene-based couplers and heterocyclic couplers, and the addition salts thereof.

26. A dye composition according to claim 25, wherein the at least one coupler is present in an amount ranging from 0.001% to 20% relative to the total weight of the composition.

27. A dye composition according to claim 26, wherein the at least one coupler is present in an amount ranging from 0.005% to 6% by weight relative to the total weight of the composition.

28. A dye composition according to claim 17, further comprising at least one hydroxylated solvent.

29. A dye composition according to claim 28, wherein said at least one hydroxylated solvent is chosen from ethanol, propylene glycol, glycerol and polyol monoethers.

30. A dye composition according to claim 17, further comprising at least one adjuvant chosen from anionic, cationic, nonionic, amphoteric and zwitterionic surfactants or mixtures thereof, anionic, cationic, nonionic, amphoteric or zwitterionic polymers or mixtures thereof, mineral or organic thickeners, antioxidants, penetrating agents, sequestering agents, fragrances, buffers, dispersants, conditioning agents, film-forming agents, ceramides, preserving agents and opacifiers.

31. A dye composition according to claim 17, further comprising at least one oxidizing agent chosen from hydrogen peroxide, urea peroxide, alkali metal bromates, persalts, peracids and oxidase enzymes.

32. A process for dyeing keratin fibers, comprising applying a dye composition to keratin fibers and leaving it to act for a period sufficient to obtain a desired coloration, wherein said dye composition comprises, in a suitable dyeing medium, at least one dicationic bis-hydrazone compound of formula (I)

DYE-L-DYE in which each of the chromophores DYE, which may be identical or different, is chosen from chromophores of formulae (Ia), (Ib), (Ic), (Id), (Ie), (If) and (Ig) below:

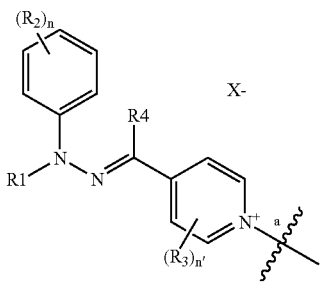
(Ia)

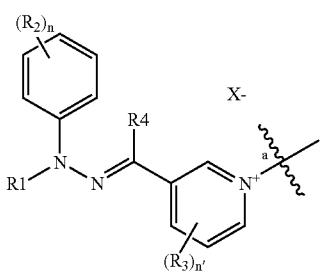
(Ib)

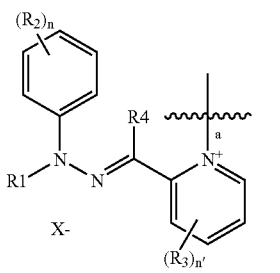
(Ic)

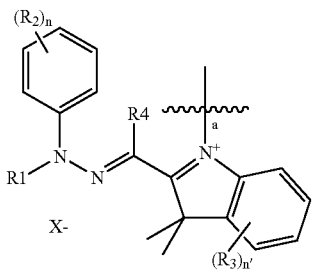
(Id)

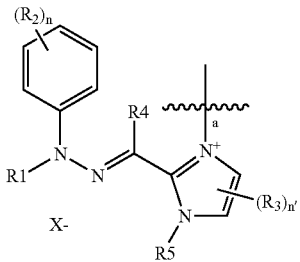
(Ie)

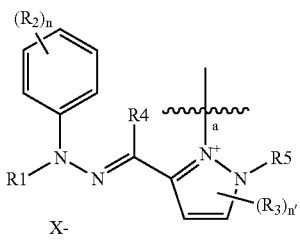
(If)

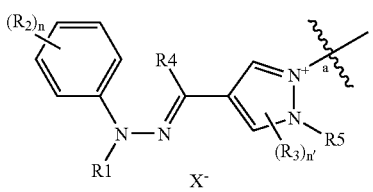
(Ig)

wherein:

the groups $R_1$ and $R_5$, independently of each other, are chosen from linear or branched, saturated or unsaturated $C_1$-$C_{20}$ hydrocarbon-based chains, which can form one or more optionally substituted, optionally aromatic 3- to 7-membered carbon-based rings, the chains being optionally substituted or being optionally interrupted with at least one hetero atom or with at least one group bearing a hetero atom, the groups $R_2$ and $R_3$, independently of each other, are chosen from:

a halogen atom chosen from bromine, chlorine and fluorine;

linear or branched, saturated or unsaturated $C_1$-$C_{16}$ hydrocarbon-based chains, which can form one or more optionally aromatic 3- to 6-membered carbon-based rings, the chain being optionally substituted or being optionally interrupted with at least one hetero atom or with at least one group bearing at least one hetero atom;

a hydroxyl group;

a $C_1$-$C_4$ alkoxy group; a $C_2$-$C_4$ (poly)hydroxyalkoxy group; an alkoxycarbonyl group (RO—CO—) in which R is a $C_1$-$C_4$ alkyl radical; or an alkylcarbonyloxy radical (RCO—O—) in which R is a $C_1$-$C_4$ alkyl radical; an optionally substituted aryloxy group;

an amino group, an amino group substituted with at least one $C_1$-$C_4$ alkyl radical, which may be identical or different, optionally bearing at least one hydroxyl group, the two alkyl radicals possibly forming, with the nitrogen atom to which they are attached, a saturated or unsaturated, optionally substituted 5- or 6-membered heterocycle, optionally bearing another nitrogen or non-nitrogen hetero atom; an alkylcarbonylamino group (RCO—NR—) in which the radicals R, independently of each other, are chosen from $C_1$-$C_4$ alkyl radicals; a carbamoyl group ($(R)_2$N—CO—) in which the radicals R, independently of each other, are chosen from a hydrogen atom and a $C_1$-$C_4$ alkyl radical; a ureido group (N(R)$_2$—CO—NR'—) in which the radicals R and R', independently of each other, are chosen from a hydrogen atom and a $C_1$-$C_4$ alkyl radical; a sulfonamide group ($(R)_2$N—SO$_2$—) in which the radicals R, independently of each other, are chosen from a hydrogen atom and a $C_1$-$C_4$ alkyl radical; an alkylthio group (R—S—) in which the group R is a $C_1$-$C_4$ alkyl radical; an alkylsulfonylamino group (RSO$_2$—NR'—) in which the radicals R and R', independently of each other, are chosen from a hydrogen atom and a $C_1$-$C_4$ alkyl radical;

a nitro group; a cyano group; a halogen atom;

a trifluoromethyl group (CF$_3$);

$R_1$ and $R_2$ may also form, with the nitrogen atom substituted with $R_1$, a saturated or unsaturated, substituted or unsubstituted 5- or 6-membered heterocycle;

two adjacent radicals $R_2$ may form, together with the carbon atoms to which they are attached, a saturated or unsaturated, substituted or unsubstituted 5- or 6-membered aromatic ring or heterocycle;

two adjacent radicals $R_3$ can together form a saturated or unsaturated, substituted or unsubstituted 5- or 6-membered aromatic ring or heterocycle;

the groups $R_4$, independently of each other, are chosen from:

a hydrogen atom;

linear or branched, saturated or unsaturated $C_1$-$C_{16}$ hydrocarbon-based chains, which can form at least one optionally aromatic 3- to 6-membered carbon-based ring, the chains being optionally substituted, optionally interrupted with at least one hetero atom or with at least one group bearing at least one hetero atom;

an amino group, an amino group substituted with at least one $C_1$-$C_4$ alkyl radical, which may be identical or different, optionally bearing at least one hydroxyl group, the two alkyl radicals possibly forming, with the nitrogen atom to which they are attached, a saturated or unsaturated, optionally substituted 5- or 6-membered heterocycle, optionally bearing another nitrogen or non-nitrogen hetero atom; an alkylcarbonylamino group (RCO—NR—) in which the radicals R, independently of each other, are chosen from $C_1$-$C_4$ alkyl radicals; a ureido group (N(R)$_2$—CO—NR'—) in which the radicals R and R', independently of each other, are chosen from a hydrogen atom and a $C_1$-$C_4$ alkyl radical; an alkylsulfonylamino group (RSO$_2$—NR'—) in which the radicals R and R', independently of each other, are chosen from a hydrogen atom and a $C_1$-$C_4$ alkyl radical;

n is an integer from 0 to 5, n' is an integer from 0 to 4, the bond a in formulae (Ia), (Ib), (Ic), (Id), (Ie), (If) and (Ig) links each of the chromophores DYE to the linker L of formula (I), X is an organic or mineral anion or mixture of anions for equilibrating the charge(s) of the compound Ia or Ib;

the group L is a linear or branched $C_1$-$C_{60}$ hydrocarbon-based chain that can form at least one optionally aromatic, optionally substituted 3- to 7-membered carbon-based ring, the chain being optionally substituted, optionally interrupted with at least one hetero atom or with at least one group bearing a hetero atom, L not comprising any peroxide, nitro, diazo or nitroso groups, the linker L being linked to the quaternized nitrogen atom of each of the chromophores DYE via a carbon atom, L not being cationic;

with the proviso that when the two chromophores DYE are identical and correspond to formula (Ia) with n=n'=0, then the group L is not one of the following groups:

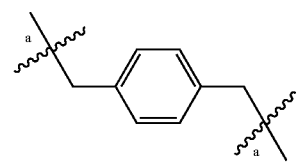

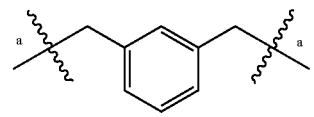

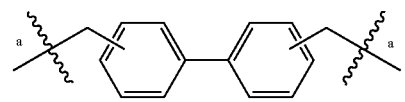

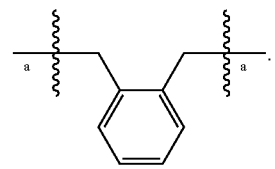

33. A process for obtaining dyeing results on keratin fibers that show good resistance to external agents and to shampoo, said process comprising applying to keratin fibers a dye composition comprising, in a suitable dyeing medium, at least one dicationic bis-hydrazone compound of formula (I)

DYE-L-DYE in which each of the chromophores DYE, which may be identical or different, is chosen from chromophores of formulae (Ia), (Ib), (Ic), (Id), (Ie), (If) and (Ig) below:

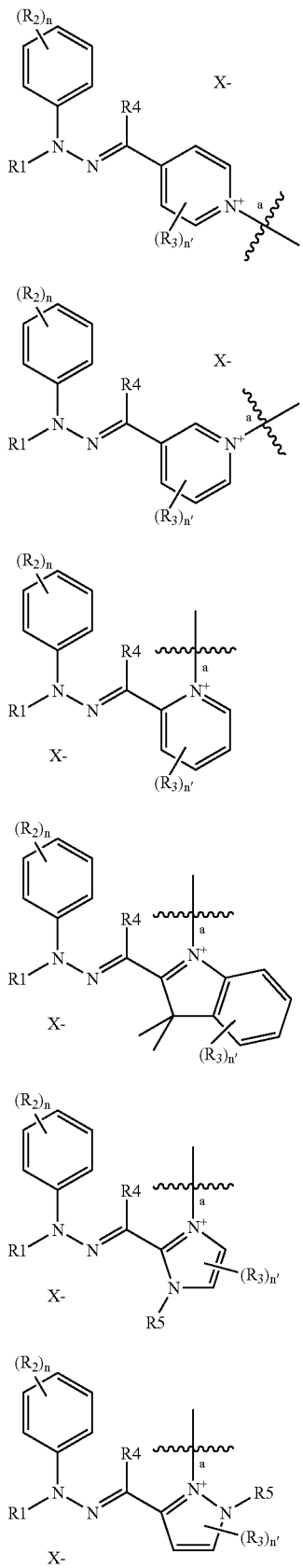

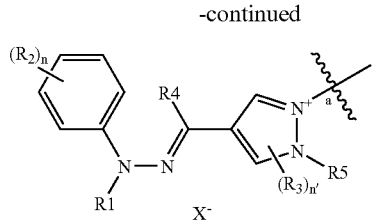

wherein:
the groups $R_1$ and $R_5$, independently of each other, are chosen from linear or branched, saturated or unsaturated $C_1$-$C_{20}$ hydrocarbon-based chains, which can form one or more optionally substituted, optionally aromatic 3- to 7-membered carbon-based rings, the chains being optionally substituted or being optionally interrupted with at least one hetero atom or with at least one group bearing a hetero atom, the groups $R_2$ and $R_3$, independently of each other, are chosen from:

a halogen atom chosen from bromine, chlorine and fluorine;

linear or branched, saturated or unsaturated $C_1$-$C_{16}$ hydrocarbon-based chains, which can form one or more optionally aromatic 3- to 6-membered carbon-based rings, the chain being optionally substituted or being optionally interrupted with at least one hetero atom or with at least one group bearing at least one hetero atom;

a hydroxyl group;

a $C_1$-$C_4$ alkoxy group; a $C_2$-$C_4$ (poly)hydroxyalkoxy group; an alkoxycarbonyl group (RO—CO—) in which R is a $C_1$-$C_4$ alkyl radical; or an alkylcarbonyloxy radical (RCO—O—) in which R is a $C_1$-$C_4$ alkyl radical; an optionally substituted aryloxy group;

an amino group, an amino group substituted with at least one $C_1$-$C_4$ alkyl radical, which may be identical or different, optionally bearing at least one hydroxyl group, the two alkyl radicals possibly forming, with the nitrogen atom to which they are attached, a saturated or unsaturated, optionally substituted 5- or 6-membered heterocycle, optionally bearing another nitrogen or non-nitrogen hetero atom; an alkylcarbonylamino group (RCO—NR—) in which the radicals R, independently of each other, are chosen from $C_1$-$C_4$ alkyl radicals; a carbamoyl group ((R)$_2$N—CO—) in which the radicals R, independently of each other, are chosen from a hydrogen atom and a $C_1$-$C_4$ alkyl radical; a ureido group (N(R)$_2$—CO—NR'—) in which the radicals R and R', independently of each other, are chosen from a hydrogen atom and a $C_1$-$C_4$ alkyl radical; a sulfonamide group ((R)$_2$N—SO$_2$—) in which the radicals R, independently of each other, are chosen from a hydrogen atom and a $C_1$-$C_4$ alkyl radical; an alkylthio group (R—S—) in which the group R is a $C_1$-$C_4$ alkyl radical; an alkylsulfonylamino group (RSO$_2$—NR'—) in which the radicals R and R', independently of each other, are chosen from a hydrogen atom and a $C_1$-$C_4$ alkyl radical;

a nitro group; a cyano group; a halogen atom;

a trifluoromethyl group (CF$_3$);

$R_1$ and $R_2$ may also form, with the nitrogen atom substituted with $R_1$, a saturated or unsaturated, substituted or unsubstituted 5- or 6-membered heterocycle;

two adjacent radicals $R_2$ may form, together with the carbon atoms to which they are attached, a saturated or unsaturated, substituted or unsubstituted 5- or 6-membered aromatic ring or heterocycle;

two adjacent radicals $R_3$ can together form a saturated or unsaturated, substituted or unsubstituted 5- or 6-membered aromatic ring or heterocycle;

the groups $R_4$, independently of each other, are chosen from:
- a hydrogen atom;
- linear or branched, saturated or unsaturated $C_1$-$C_{16}$ hydrocarbon-based chains, which can form at least one optionally aromatic 3- to 6-membered carbon-based ring, the chains being optionally substituted, optionally interrupted with at least one hetero atom or with at least one group bearing at least one hetero atom;
- an amino group, an amino group substituted with at least one $C_1$-$C_4$ alkyl radical, which may be identical or different, optionally bearing at least one hydroxyl group, the two alkyl radicals possibly forming, with the nitrogen atom to which they are attached, a saturated or unsaturated, optionally substituted 5- or 6-membered heterocycle, optionally bearing another nitrogen or non-nitrogen hetero atom; an alkylcarbonylamino group (RCO—NR—) in which the radicals R, independently of each other, are chosen from $C_1$-$C_4$ alkyl radicals; a ureido group (N(R)$_2$—CO—NR'—) in which the radicals R and R', independently of each other, are chosen from a hydrogen atom and a $C_1$-$C_4$ alkyl radical; an alkylsulfonylamino group (RSO$_2$—NR'—) in which the radicals R and R', independently of each other, are chosen from a hydrogen atom and a $C_1$-$C_4$ alkyl radical;

n is an integer from 0 to 5, n' is an integer from 0 to 4, the bond a in formulae (Ia), (Ib), (Ic), (Id), (Ie), (If) and (Ig) links each of the chromophores DYE to the linker L of formula (I), X is an organic or mineral anion or mixture of anions for equilibrating the charge(s) of the compound Ia or Ib;

the group L is a linear or branched $C_1$-$C_{60}$ hydrocarbon-based chain that can form at least one optionally aromatic, optionally substituted 3- to 7-membered carbon-based ring, the chain being optionally substituted, optionally interrupted with at least one hetero atom or with at least one group bearing a hetero atom, L not comprising any peroxide, nitro, diazo or nitroso groups, the linker L being linked to the quaternized nitrogen atom of each of the chromophores DYE via a carbon atom, L not being cationic;

with the proviso that when the two chromophores DYE are identical and correspond to formula (Ia) with n=n'=0, then the group L is not one of the following groups:

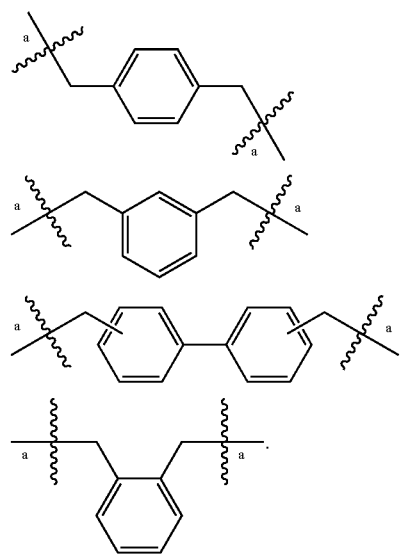

* * * * *

UNITED STATES PATENT AND TRADEMARK OFFICE
CERTIFICATE OF CORRECTION

PATENT NO. : 7,410,506 B2  Page 1 of 3
APPLICATION NO. : 11/249370
DATED : August 12, 2008
INVENTOR(S) : David et al.

It is certified that error appears in the above-identified patent and that said Letters Patent is hereby corrected as shown below:

In claim 4, column 95, line 67, "$C_1$-$C_{20}$ alkyl-(hetero)aryl-$C_1$-$C_{20}$" should read --$C_1$-$C_{20}$ alkyl-(hetero)aryl-$C_1$-$C_{20}$--.

In claim 5, column 96, line 2, "$C_1$-$C_{10}$ alkyl-(hetero)aryl-$C_1$-$C_{10}$" should read --$C_1$-$C_{10}$ alkyl-(hetero)aryl-$C_1$-$C_{10}$--.

In claim 6, column 96, line 3, "according claim" should read --according to claim--.

In claim 15, column 104, lines 2-13,

"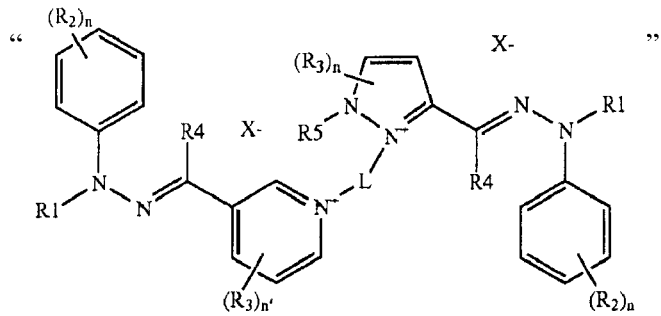"

should read

--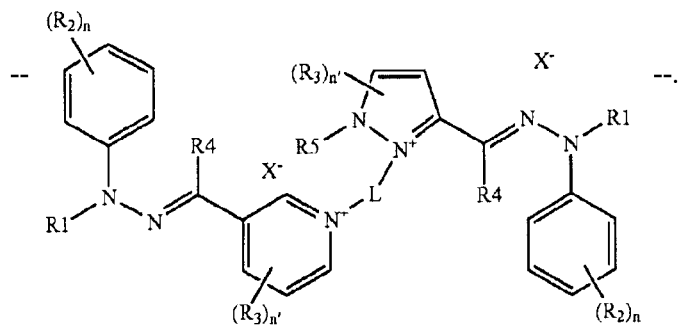--.

UNITED STATES PATENT AND TRADEMARK OFFICE
CERTIFICATE OF CORRECTION

PATENT NO. : 7,410,506 B2
APPLICATION NO. : 11/249370
DATED : August 12, 2008
INVENTOR(S) : David et al.

It is certified that error appears in the above-identified patent and that said Letters Patent is hereby corrected as shown below:

In claim 15, column 104, lines 16-26

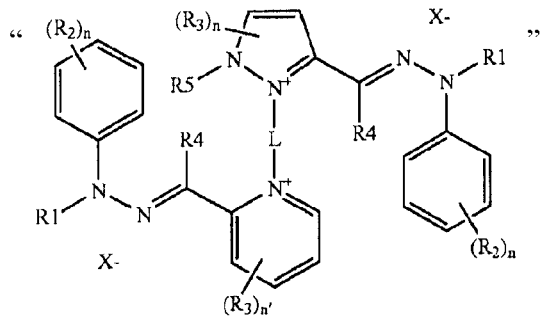

should read

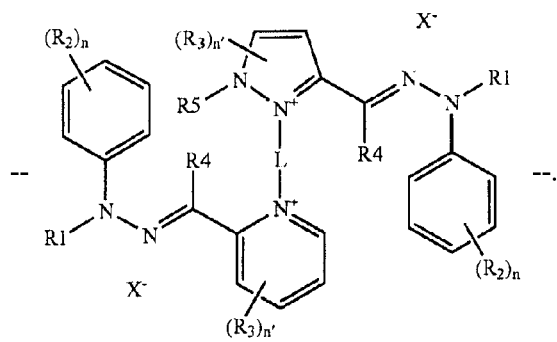

In claim 15, column 105, lines 29-37,

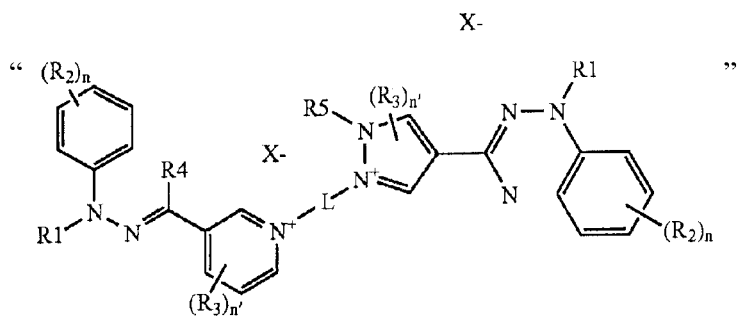

UNITED STATES PATENT AND TRADEMARK OFFICE
CERTIFICATE OF CORRECTION

PATENT NO. : 7,410,506 B2
APPLICATION NO. : 11/249370
DATED : August 12, 2008
INVENTOR(S) : David et al.

It is certified that error appears in the above-identified patent and that said Letters Patent is hereby corrected as shown below:

should read

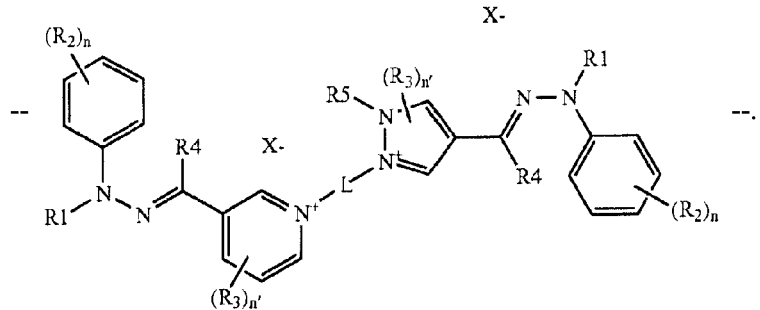

In claim 15, column 105, line 66, "n'and" should read --n' and--.

In claim 16, column 106, lines 7-9, "4-{(E)-[methyl(phenyl)hydrazono]methyl}-1-[4-(4-((E)-[methyl(phenyl)hydrazono]methyl}pyridinium-1-yl)butyl]pyridinium" should read --4-{(E)-[methy(phenyl)hydrazono]methyl}-1-[4-(4-{(E)-[methyl(phenyl)hydrazono]methyl}pyridinium-1-yl)butyl]pyridinium--.

Signed and Sealed this

Thirtieth Day of September, 2008

JON W. DUDAS
*Director of the United States Patent and Trademark Office*